(12) United States Patent
Menzel et al.

(10) Patent No.: US 6,265,174 B1
(45) Date of Patent: Jul. 24, 2001

(54) METHODS AND COMPOSITIONS FOR IDENTIFYING AND MODULATING CTIONPROTEIN-INTERACTIONS

(75) Inventors: Rolf Menzel, Yardley; Weihong Hsing, Wrightstown, both of PA (US); Pamela A. Taggart, Plainsboro, NJ (US)

(73) Assignee: Morphochem, Inc., Monmouth Junction, NJ (US)

(*) Notice: Subject to any disclaimer, the term of this patent is extended or adjusted under 35 U.S.C. 154(b) by 0 days.

(21) Appl. No.: 09/149,922

(22) Filed: Sep. 9, 1998

Related U.S. Application Data

(60) Provisional application No. 60/064,058, filed on Nov. 3, 1997.

(51) Int. Cl.$^7$ .......................... G01N 33/53; C07K 19/00; C12N 15/62
(52) U.S. Cl. .......................... 435/7.2; 435/7.1; 435/69.7; 530/350; 536/23.4
(58) Field of Search .......................... 435/7.1, 7.2, 69.7; 530/350; 536/23.4

(56) References Cited

U.S. PATENT DOCUMENTS

| | | |
|---|---|---|
| 5,482,835 | 1/1996 | King et al. . |
| 5,521,066 | 5/1996 | Menzel et al. . |
| 5,585,277 | 12/1996 | Bowie et al. . |
| 5,679,582 | 10/1997 | Bowie et al. . |
| 5,739,029 | 4/1998 | King et al. . |
| 5,744,341 | 4/1998 | Cunningham, Jr. et al. . |

FOREIGN PATENT DOCUMENTS

| | | |
|---|---|---|
| WO 96/23810 | 8/1996 | (WO) . |

OTHER PUBLICATIONS

Ivey et al. The cadC Gene Product of *Alkaliphilic Bacillus firmus* OF4 Partially Restores Na+ Resistance to an *escherichia coli* Strain Lacking an Na+ /H= Antiporter (NhaA). J. of Bact. 174(15):4878–4884, Aug. 1992.*
Abrahmsen et al., 1986, "Secretion of Heterologous Gene Products to the Culture Medium of *Escherichia coli*", Nucl. Acids. Res. 14:7487–7501.
Agre et al., 1989, "Cognate DNA Binding Specificity Retained after Leucine Zipper Exchange Between GCN4 and C/EBP", Science 246:922–926.
Babe et al., 1992, "Synthetic 'Interface' Peptides Alter Dimeric Assembly of the HIV 1 and 2 Proteases", Prot. Sci. I:1244–1253.
Bachman, 1990, "Linkage Map of *Escherichia coli* K–12, Edition 8", Microbiol. Rev. 54:130–197.
Bairoch and Apweiler, 1998, "The SWISS–PROT Protein Sequence Data Bank and its Supplement TrEMBL in 1998", Nucl. Acids. Res. 26:38–42.
Baloh et al., 1998, "GFRα3 Is an Orphan Member of the GDNF/Neurturin/Persephin Receptor Family", Proc. Natl. Acad. Sci. USA 95:5801–5806.

Beato et al., 1995, "Steroid Hormone Receptors: Many Actors in Search of a Plot", Cell 83:851–857.
Bell et al., 1980, "Sequence of the Human Insulin Gene", Nature 284:26–32.
Boni–Schnetzler et al., "Structural Requirements for the Transmembrane Activation of the Insulin Receptor Kinase", J. Biol. Chem. 261:15281–15287.
Brosig and Langosch, 1998, "The Dimerization Motif of the Glycophorin A Transmembrane Segment in Membranes: Importance of Glycine Residues", Protein Sci. 7:1052–1056.
Campbell, 1997, "Growth–Hormone Signal Transduction", J. Pediatr. 131:S42–S44.
Cantley et al., 1991, "Oncogenes and Signal Transduction", Cell 64:281–302.
Catterall, 1991, "Functonal Subunit Structure of Voltage–Gated Calcium Channels", Science 253:1499–1500.
Chalfie et al., 1994, "Green Fluorescent Protein as a Marker for Gene Expression", Science 263:802–805.
Clements et al., 1980, "Properties of Homogeneous Heat–Labile Enterotoxin from *Escherichia coli*", Infect. Immun. 29:91–97.
Coussens et al., 1985, "Tyrosine Kinase Receptor with Extensive Homology to EGF Receptor Shares Chromosomal Location with Neu Oncogene" Science 230:1132–1139.
Darnell et al., 1994, "Jak–STAT Pathways and Transcriptional Activation in Response to IFNs and other Extracellular Signaling Proteins", Science 264:1415–1421.
Dell et al., 1994, "Altered pH and Lysine Signaling Mutants of cadC, a Gene Encoding a Membrane–Bound Transcriptional Activator of the *Escherichia Coli* cadBA Operon", Mol. Microbiology 14:7–16.
DeWet et al., 1987, "Firefly Luciferase Gene: Structure and Expression in Mammalian Cells", Mol. Cell. Biol. 7:725–737.
Dolle, 1996, "Discovery of Enzyme Inhibitors through Combinatorial Chemistry", Mol. Div. 2:223–236.
Drolet et al., 1995, "Overexpression of Rnase H Partially Complements the Growth Defect of an *Escherichia coli* ΔtopA Mutant: R–Loop Formation Is a Major Problem in the Absence of DNA Topoisomerase I", Proc. Natl. Acad. Sci. USA 92:3526–3530.

(List continued on next page.)

*Primary Examiner*—John Ulm
(74) *Attorney, Agent, or Firm*—Peter F. Corless; Dike, Bronstein, Roberts & Cushman, IP Group

(57) ABSTRACT

The present invention relates to methods and compositions for the identification and modulation of protein-protein interactions. Specifically, the invention relates to methods and compositions for efficient, sensitive, high-throughput CadC-based screens for the identification of peptides involved in protein-protein interactions, including, but not limited to, peptides comprising amino acid sequences involved in receptor dimerization. The invention further relates to methods and compositions for efficient, sensitive, high-throughput CadC-based screens for compounds which modulate protein-protein interactions, such as, for example, modulation of interactions between protein sequences involved in receptor interactions, e.g., dimerization.

51 Claims, 22 Drawing Sheets

OTHER PUBLICATIONS

Ebina et al., 1985, "The Human Insulin Receptor cDNA: The Structural Basis for Hormone–Activated Transmembrane Signalling", Cell 40:747–758.

Eichler and Houghten, 1995, "Generation and Utilization of Synthetic Combinatorial Libraries", Mol. Med. Today 1:174–180.

Eikmanns et al., 1991, "A Family of *Cornybacterium glutamicum/Escerichia coli* Shuttle Vectors for Cloning, Controlled Gene Expression, and Promoter Probing", Gene 102:93–98.

Emorine et al., 1989, "Molecular Characterization of the Human Beta 3–Adrenergic Receptor", Science 245:1118–1121.

Eustice et al, 1991, "A Sensitive Method for the Detection of β–Galactosidse in Transfected Mammalian Cells", BioTechniques 11:739–742.

Evans, 1989, "Molecular Characterization of the Glucocorticoid Receptor", Recent Prog. Horm. Res. 45:1–22.

Friedrich and Soriano, 1991, "Promoter Traps in Embryonic Stem Cells: A Genetic Screen to Identify and Mutate Developmental Genes in Mice", Genes & Dev. 5:1513–1523.

Gray et al., 1990, "Cloning of Human Tumor Necrosis Factor (TNF) Receptor cDNA and Expression of Recombinant Soluble TNF–Binding Protein", Proc. Natl. Acad. Sci. USA 87:7380–7384.

Green et al., 1986, "Human Oestrogen Receptor cDNA: Sequence, Expression and Homology to v–erb–A", Nature 320:134–139.

Guzman et al., 1995, "Tight Regulation, Modulation, and High–Level Expression by Vectors Containing the Arabinose $P_{BAD}$ Promoter", J. Bacteriol. 177:4121–4130.

Hamilton, 1997, "CSF–1 Signal Transduction", J. Leukocyte Biol. 62:145–155.

Hegedus et al., 1998, A Series of Broad Host Range Shuttle vectors for Constitutive and Inducible Expression of heterologous Proteins in Insect Cell Lines, Gene 207:241–249.

Heim et al., 1995, "Improved Green Fluorescence", Nature 373:663–664.

Heldin, 1995, "Dimerization of Cell Surface Receptors in Signal Transduction", Cell 80:213–223.

Herz et al., 1997, "Molecular Approaches to Receptors as Targets for Drug Discovery". J. Recept. Signal Transduct. Res. 17:671–776.

Hobom et al., 1995, "OmpA Fusion Proteins for Presentation of Foreign Antigens on the Bacterial Outer Membrane", Dev. Biol. Stand. 84:255–262.

Hoffman and Wright, 1985, "Fusions of Secreted Proteins to mAlkaline Phosphatase: An Approach for Studying Protein Secretion", Proc. Natl. Acad. Sci. USA 82:5107–5111.

Hu et al., 1990, "Sequence Requirements for Coiled–Coils: Analysis with λ Repressor–GCN4 Leucine Fusions", Science 250:1400–1403.

Huang et al., 1997, "Molecular Cloning of the Dog β1 and β2 Adrenergic Receptors", J. Recept. Signal Transduct. Res. 17:599–607.

Huynh and Snell, 1996, "Histidine Decarboylase of Lactobacillus 30a", J. Biol. Chem. 261:1521–1527.

Johnson et al., 1986, "Expression and Structure of the Human NGF Receptor", Cell 4:545–554.

Johnson et al., 1996, "Refolding, Purification, and Characterization of Human Erythropoietin Binding Protein Produced in *Escherichia coli*", Protein Expression and Purification 7:104–113.

Kadonaga et al., 1984, "The Role of the Beta–lactamase Signal Sequence in the Secretion of Proteins by *Escherichia Coli*" J. Biol. Chem. 259:2149–2154.

Kaiser et al., 1987, "Many Random Sequences Functionally Replace the Secretion Signal Sequence of Yeast Invertase", Science 235:312–317.

Karp, 1989, "Expression of Bacterial Luciferase genes from *Vibrio harveyi* in *Bacillus subtilis* and in *Escherichia coli*", Biochim. Biophys. Acta 1007:84–89.

Koch et al., 1991, "SH2 and SH3 domains: Elements that Control Interactions of Cytoplasmic Signaling Proteins" Science 252:668–674.

Kolmar et al., 1995, "Immunoglobulin Mutant Library Genetically Screened for Folding Stability Exploiting Bacterial Signal Transduction", J. Mol. Biol. 251:471–476.

Kolmar et al., 1995, "Membrane Insertion of the Bacterial Signal Transduction Protein ToxR and Requirements of Transcription Activation Studies by Modular Replacement of Different Protein Substructures", EMBO J. 14:3895–3904.

Lam, 1997, "Application of Combinatorial Library Methods in Cancer Research and Drug Discovery", Anti–Cancer Drug Des. 12:145–167.

Lamb and McKnight, 1991, "Diversity and Specificity in Transcriptional Regulation: The Benefits of Heterotypic Dimerization", Trends Biochem. Sci. 16:417–422.

Langosch et al., 1996, "Dimerization of the Glycolphorin A Transmembrane Segment in Membranes Probed with the ToxR Transcription Activator", J. Mol. Biol. 263:525–530.

Lemmon et al., 1997, "Kit Receptor Dimerization Is Driven by Bivalent Binding of Stem Cell Factor", J. Biol. Chem. 272:6311–6317.

Lerner and Inouye, 1990, "Low Copy Number Plasmids for Regulated Low–Level Expression of Cloned Genes in *Escherichia coli* with Blue/White Insert Screening Capability", Nucl. Acids. Res. 18:4631–.

Leung et al., 1987, "Growth Hormone Receptor and Serum Binding Protein: Purification, Cloning and Expression", Nature 330:537.

Lo et al., 1988, "*Bacillus subtilis* β–1,4,–Endoglucanase Products from Intact and Truncated Genes Are Secreted into the Extracellular Medium by *Escherichia coli*", App. Env. Microbiol. 54:2287–2292.

Loessner et al., 1996, "Construction of Luciferase Reporter Bacteriophage A511::luxAB for Rapid and Sensitive Detection of Viable Listeria Cells", Appl. Env. Microbiol. 62:1133–1140.

MacIntyre et al., 1990, "Export Incompatibility of N–Terminal Basic residues ina Mature Polypeptide of *Escherichia coli* can Be Alleviated by Optimising the Signal Peptide", Mol. Gen. Genet. 221:466–474.

Maloy et al., 1996, *Genetic Analysis of Pathogenic Bacteria* (Cold Spring Harbor Laboratory Press, New York).

Mangelsdorf et al., 1985, "The Nuclear Superfamily: The Second Decade", Cell 83:835–839.

Marmenout et al., 1985, "Molecular Cloning and Expression of Human Necrosis Factor and Comparison with Mouse Tumor Necrosis Factor", Eur. J. Biochem. 152:515–522.

Martinez–Hackert and Stock, 1997, "Structural Relationships in the OmpR Family of Winged–Helix Transcription Factors", J. Mol. Biol. 69:301–312.

Meng and Bennet, 1992, "Nucleotide Sequence of the *Escherichia coli* cad Operon: A System for Neutralization of Low Extracellular pH", J. Bacteriol. 174:2659–2669.

Menzel, 1989, "A Microtiter Plate–Based System for the Semiautomated Growth and Assay of Bacterial Cells for β–Galactosidase Activity", Anal. Biochem. 181:40–50.

Miyajima et al., 1992, "Cytokine Receptors and Signal Transduction", Ann. Rev. Immunol. 10:295–331.

Miyamoto et al., 1987, "Expression of Bioluminescence by Escherichia coli Containing Recombinant Vibrio harveyi DNA", J. Bacateriol. 169:247–253.

Moe et al., 1989, "Transmembrane Signaling by a Chimera of the Escherichia coli Aspartate Receptor and the Human Insulin Receptor", Proc. Natl. Acad. Sci. USA 86:5683–5687.

Morioka–Fujimoto et al., 1991, "Modified Enterotoxin Signal Sequences Increase Secretion Level of the Recombinant Human Epidermal Growth Factor in Escherichia coli", J. Biol. Chem. 266:1728–1732.

Mynarcik et al., 1997, "Identification of Common Ligand Binding Determinants of the Insulin and Insulin–Like Growth Factor 1 Receptors", J. Biol. Chem. 272:18650–18655.

Neely et al., 1994, "Roles of LysP and CadC in Mediating the Lysine Requirement for Acid Induction of the Escherichia Coli Cad Operon", J. Bacteriol. 176:3278–3285.

Noguchi et al., 1991, "Cloning of the Human Erythropoietin Receptor Gene", Blood 78:2548–2556.

Nolan et al., 1988, "Fluorescence–Activated Cell Analysis and Sorting of Viable Mammalian Cells Based on β–D–Galactosidase Activity after Transduction of Esherichia coli lacZ", Proc. Natl. Acad. Sci. USA 85:2603–2607.

Oka et al., 1985, "Synthesis and Secretion of Human Epidermal Growth Factor by Esherichia coli", Proc. Natl. Acad. Sci. USA 82:7212–7216.

Riedel et al., 1989, "Cytoplasmic Domains Determine Signal Specificity, Cellular Routing Characteristics and Influence Ligand Binding of Epidermal Growth Factor and Insulin Receptors", EMBO J. 8:2943–2954.

Roberts et al., 1989, "Expression of the Escherichia coli β–Glucuronidase Gene in Industrial and Phytopathogenic Filamentous Fungi", Curr. Genet. 15:177–180.

Rudd, 1992, in Miller, 1992, Miller, J.H., 1992, A Short Course in Bacterial Genetics, Cold Spring Harbor Laboratory Press, NY, pp. 2.3–2.43.

Samanta et al., 1994, "Ligand and p185c–neu Density Govern Receptor Interactions and Tyrosine Kinase Activation" Proc. Natl. Acad. Sci. USA 91:1711–1715.

Schramm et al., 1993, "The Inhibition of HIV–1 Protease by Interface Peptides", Biochem. Biophys. Res. Comm. 194:595–600.

Schultz and Yarus, 1990, "A Simple and Sensitive In Vivo Liciferase Assay for tRNA–Mediated Nonsense Suppression", J. Bacteriol. 172:595–602.

Sepp–Lorenzino, 1998, "Structure and Function of the Insulin–like Growth Factor I Receptor" Breast Cancer Res. Treat. 47:235–253.

Seto et al., 1992, "Chromosomal Gene Organization of the Human Granulocyte Colony–Stimulating Factor Receptor", J. Immunol. 148:259–266.

Soede–Bobok and Touw, 1997, "Molecular Understanding of Hematopoietin/Cytokine Receptor Signaling Defects in hematopoietic Disorders", J. Mol. Med. 75:470–477.

Sparrow et al., 1997, "The Disulfide Bonds in the C–Terminal Domains of the Human Insulin Receptor Ectodomain", J. Biol. Chem. 272:29460–29467.

Stim and Bennet, 1993, "Nucleotide Sequence of the adi Gene, Which Encodes the Biodegrative Acid–Induced Arginine Decarboxylase of Escherichia coli", J. Bacteriol. 175:1221–1234.

Strader et al., 1994, "Structure and Function of G Protein–Coupled Receptors", Ann. Rev. Biochem. 63:101–132.

Taylor and Rose, 1988, "A Correction in the Nucleotide Sequence of the Tn903 Kanamycin Resistance Determinant in pUC4K", Nucl. Acids. Res. 16:358.

Todt et al., 1992, "Effects of pH on Bacterial Porin Function", 31:10471–10478.

Tsai and O'Malley, 1994, "Molecular Mechanisms of Action of Steroid/Thyroid Receptor Superfamily Members", Ann. Rev. Biochem. 63:451–486.

Turnbough et al., 1983, "Attenuation Control of pyrBI Operon Expression in Escherichia Coli K–12", Proc. Natl. Acad. Sci. USA 80:368–372.

Ullrich et al., 1985, "Human Insulin Receptor and its Relationship to the Tyrosine Kinase Family of Oncogenes", Nature 313:756–761.

Utsumi et al., 1989, "Activation of Bacterial Porin Gene Expression by a Chimeric Transducer in Response to Aspartate", Science 245:1246–1249.

Vigers et al., 1997, "Crystal Structure of the Type–I Interleukin–1 Receptor Complexed with Interleukin–1Beta", Nature 386:190–194.

Watson et al., 1992, "Identification of Elements Involved in Transcriptional Regulation of the Escherichia coli cad Operon by External pH", J. Bacteriol. 174:530–540.

Weiss and Schlessinger, 1998, "Switching Signals On or Off by Receptor Dimerization" Cell 94:277–280.

Woo et al., 1998, "Characterization of the Recombinant Extracellular Domain of the Neurotrophin Receptor TrkA and its Interaction with Nerve Growth factor (NGF)", Protein Sci. 7:1006–1016.

Zhang et al., 1991, "Dissociative Inhibition of Dimeric Enzymes", J. Biol. Chem. 266:15591–15594.

Baumann et al., 1994, "Multiple Regions within the Cytoplasmic Domains of the Leukemia Inhibitory Factor Receptor and gp130 in Signal Transduction in Hepatic and Neuronal Cells", Mol. Cell. Biol. 14:138–146.

Hollenbaugh et al., 1992, "The Human T Cell Antigen gp39, a Member of the TNF Gene Family, Is a Ligand for the CD40 Receptor: Expression of a Soluble Form of gp39 with B Cell Co–Stimulatory Activity", EMBO J. 11:4313–4321.

* cited by examiner

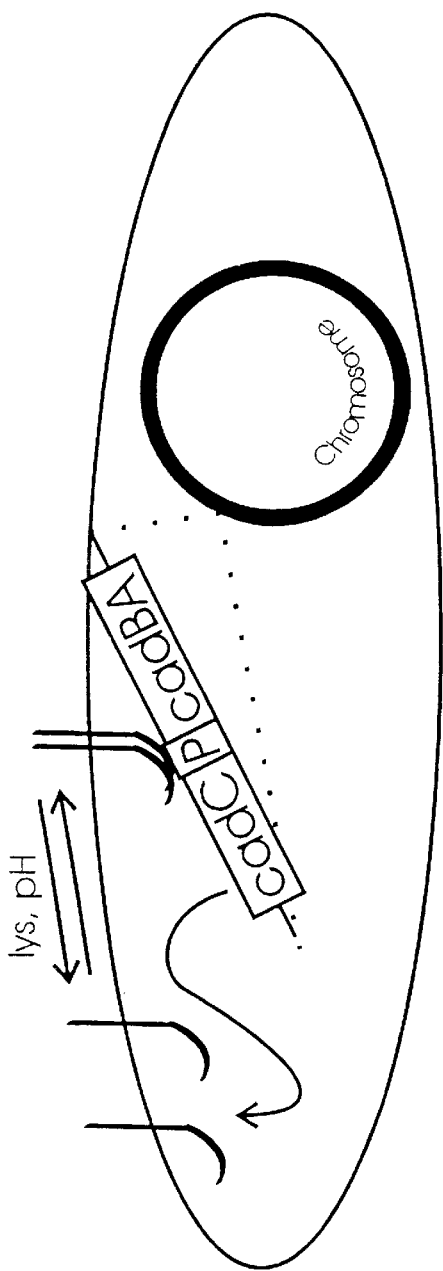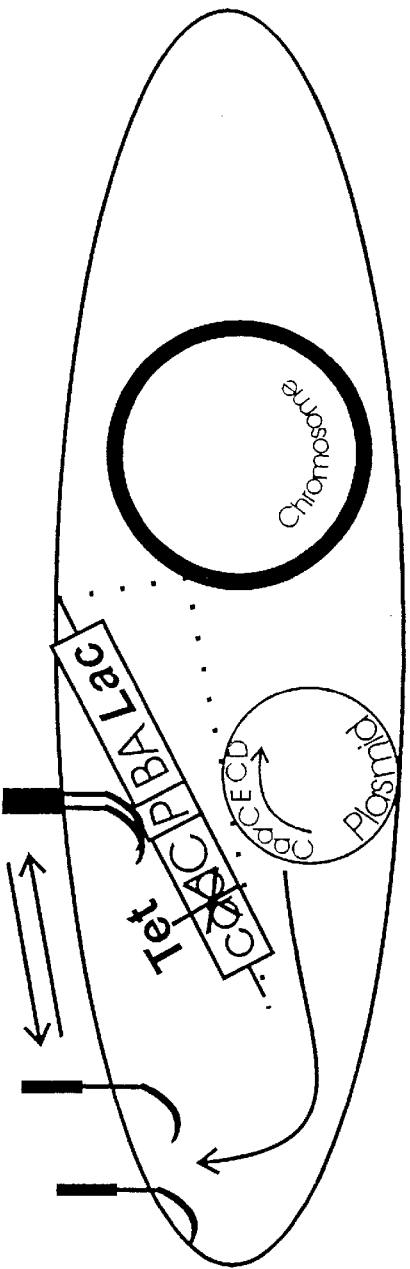
FIG. 1A
FIG. 1B

```
Met Gln Gln Pro Val Val Arg Val Gly Glu Trp Leu Val Thr Pro Ser
1            5                    10                  15
Ile Asn Gln Ile Ser Arg Asn Gly Arg Gln Leu Thr Leu Glu Pro Arg
            20                  25                  30
Leu Ile Asp Leu Leu Val Phe Phe Ala Gln His Ser Gly Glu Val Leu
            35                  40                  45
Ser Arg Asp Glu Leu Ile Asp Asn Val Trp Lys Arg Ser Ile Val Thr
    50              55                  60
Asn His Val Val Thr Gln Ser Ile Ser Glu Leu Arg Lys Ser Leu Lys
65              70                  75                      80
Asp Asn Asp Glu Asp Ser Pro Val Tyr Ile Ala Thr Val Pro Lys Arg
                85                  90                  95
Gly Tyr Lys Leu Met Val Pro Val Ile Trp Tyr Ser Glu Glu Glu Gly
            100                 105                 110
Glu Glu Ile Met Leu Ser Ser Pro Pro Ile Pro Glu Ala Val Pro
            115                 120                 125
Ala Thr Asp Ser Pro Ser His Ser Leu Asn Ile Gln Asn Thr Ala Thr
    130             135                 140
Pro Pro Glu Gln Ser Pro Val Lys Ser Lys Arg Phe Thr Thr Phe Trp
145             150                 155                 160
Val Trp Phe Phe Leu Leu Ser Leu Gly Ile Cys Val Ala Leu Val
            165                 170                 175
Ala Phe Ser Ser Leu Asp Thr Arg Leu Pro Met Ser Lys Ser Arg Ile
            180 Junction 1      185                 190 Junction 5
Leu Leu Asn Pro Arg Asp Ile Asp Ile Asn Met Val Asn Lys Ser Cys
            195                 200                 205
Asn Ser Trp Ser Ser Pro Tyr Gln Leu Ser Tyr Ala Ile Gly Val Gly
            210                 215                 220
Asp Leu Val Ala Thr Ser Leu Asn Thr Phe Ser Thr Phe Met Val His
225                 230                 235                 240
Asp Lys Ile Asn Tyr Asn Ile Asp Glu Pro Ser Ser Ser Gly Lys Thr
        Junction 4 245                 250                 255
Leu Ser Ile Ala Phe Val Asn Gln Arg Gln Tyr Arg Ala Gln Gln Cys
            260                 265                 270
Phe Met Ser Ile Lys Leu Val Asp Asn Ala Asp Gly Ser Thr Met Leu
            275         Junction 2 280                 285
Asp Lys Arg Tyr Val Ile Thr Asn Gly Asn Gln Leu Ala Ile Gln Asn
290                 295                 300
Asp Leu Leu Glu Ser Leu Ser Lys Ala Leu Asn Gln Pro Trp Pro Gln
305                 310                 315                 320
Arg Met Gln Glu Thr Leu Gln Lys Ile Leu Pro His Arg Gly Ala Leu
                325                 330                 335
Leu Thr Asn Phe Tyr Gln Ala His Asp Tyr Leu Leu His Gly Asp Asp
            340                 345                 350
Lys Ser Leu Asn Arg Ala Ser Glu Leu Leu Gly Glu Ile Val Gln Ser
            355                 360                 365
Ser Pro Glu Phe Thr Tyr Ala Arg Ala Glu Lys Ala Leu Val Asp Ile
    370                 375                 380
Val Arg His Ser Gln His Pro Leu Asp Glu Lys Gln Leu Ala Ala Leu
385                 390                 395                 400
Asn Thr Glu Ile Asp Asn Ile Val Thr Leu Pro Glu Leu Asn Asn Leu
                405                 410                 415
Ser Ile Ile Tyr Gln Ile Lys Ala Val Ser Ala Leu Val Lys Gly Lys
            420                 425                 430
Thr Asp Glu Ser Tyr Gln Ala Ile Asn Thr Gly Ile Asp Leu Glu Met
        435                 440                 445
Ser Trp Leu Asn Tyr Val Leu Leu Gly Lys Val Tyr Glu Met Lys Gly
    450                 455                 460
Met Asn Arg Glu Ala Ala Asp Ala Tyr Leu Thr Ala Phe Asn Leu Arg
465                 470                 475                 480
Pro Gly Ala Asn Thr Leu Tyr Trp Ile Glu Asn Gly Ile Phe Gln Thr
                485                 490                 495
Ser Val Pro Tyr Val Val Pro Tyr Leu Asp Lys Phe Leu Ala Ser Glu
            500                 505                 510
```

FIG. 2

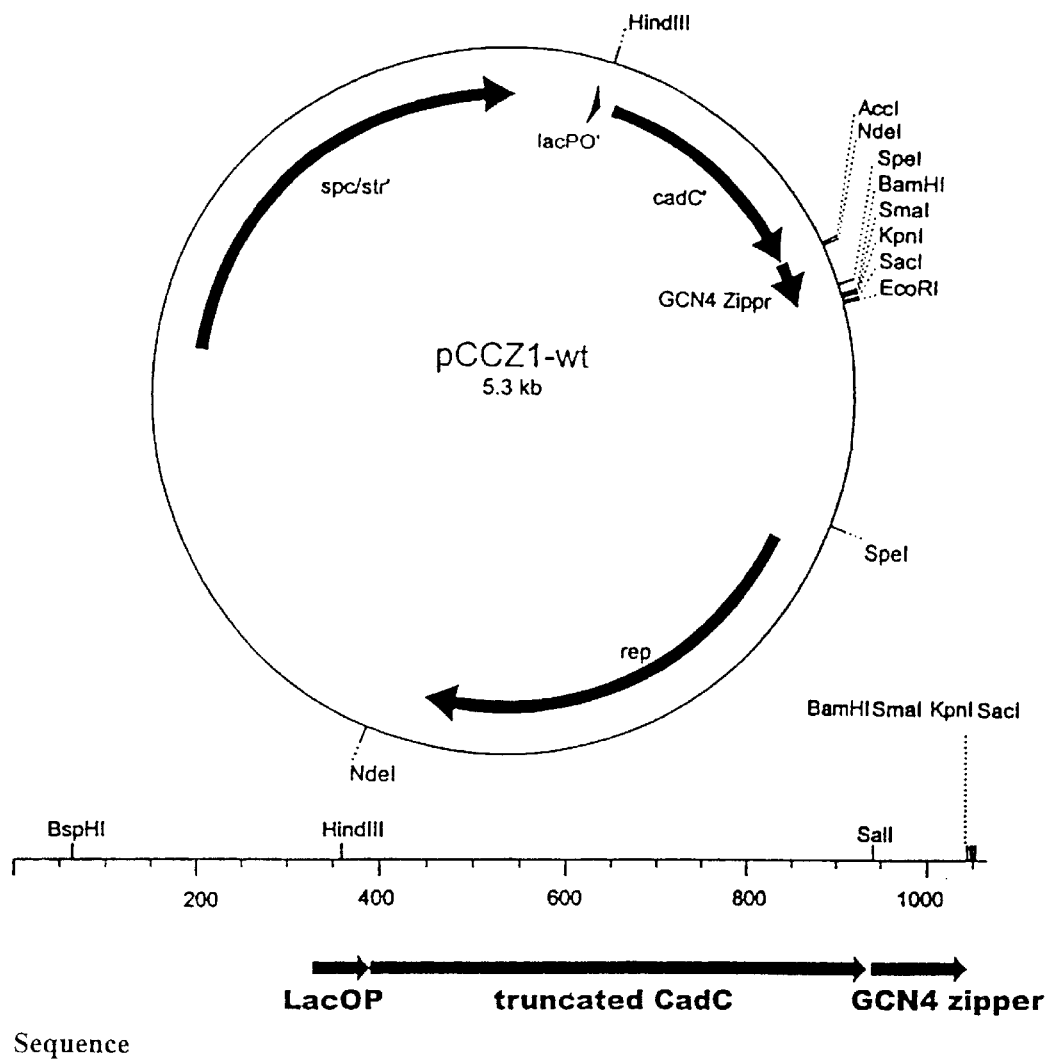

Sequence

```
GTCAAGTCTGCTTTAATTATTTTTAAGCGTGCATAATAAGCCCTACACAAATTGGGANGATATATCATGAA
AGGCTGGCTTTTTCTTGTTATCGCAATAGTTGGNGAAGTAATCGCAACATCCGCATTAAAATCTAGCGAGG
GCTTTACTAAGCTCGCGTTGGCCGATTCATTAATGCAGCTGGCACGACAGGTTTCCCGACTGGAAAGCGGG
CAGTGAGCGCAACGCAATTAATGTGAGTTAGCTCACTCATTAGGCACCCCAGGCTTTACACTTTATGCTTC
CGGCTCGTATGTTGTGTGGAATTGTGAGCGGATAACAATTTCACACAGGAAACAGCTATGACCATGATTAC
GCCAAGCTTCATTCCCTTTTCGAATGAGTTTCTATTATGCAACAACCTGTAGTTCGCGTTGGCGAATGGCT
TGTTACTCCGTCCATAAACCAAATTAGCCGCAATGGGCGTCAACTTACCCTTGAGCCGAGATTAATCGATC
TTCTGGTTTTCTTTGCTCAACACAGTGGCGAAGTACTTAGCAGGGATGAACTTATCGATAATGTCTGGAAG
AGAAGTATTGTCACCAATCACGTTGTGACGCAGAGTATCTCAGAACTACGTAAGTCATTAAAAGATAATGA
TGAAGATAGTCCTGTCTATATCGCTACTGTACCAAAGCGCGGCTATAAATTAATGGTGCCGGTTATCTGGT
ACAGCGAAGAAGAGGGAGGAAATAATGCTATCTTCGCCTCCCCCTATACCAGAGGCGGTTCCTGCCACA
GATTCTCCCTCCCACAGTCTTAACATTCAAAACACCGCAACGCCACCTGAACAATCCCCAGTTAAAAGCAA
ACGATTCACTACCTTTTGGGTATGGTTTTTTTTCCTGTTGTCGTTAGGTATCTGTGTAGCACTGGTAGCGT
TTTCAAGTCTGTCGACACATATGAAACAGCTGGAAGACAAAGTTGAAGAGCCCCTGTCTAAAAACTACCAC
CCCGAGAACGAAGTTGCGCGCCTGAAAAAACTAGTTGGTGAACGTTGAGGATCCCCGGGTACCGAGCTCG
```

FIG. 5

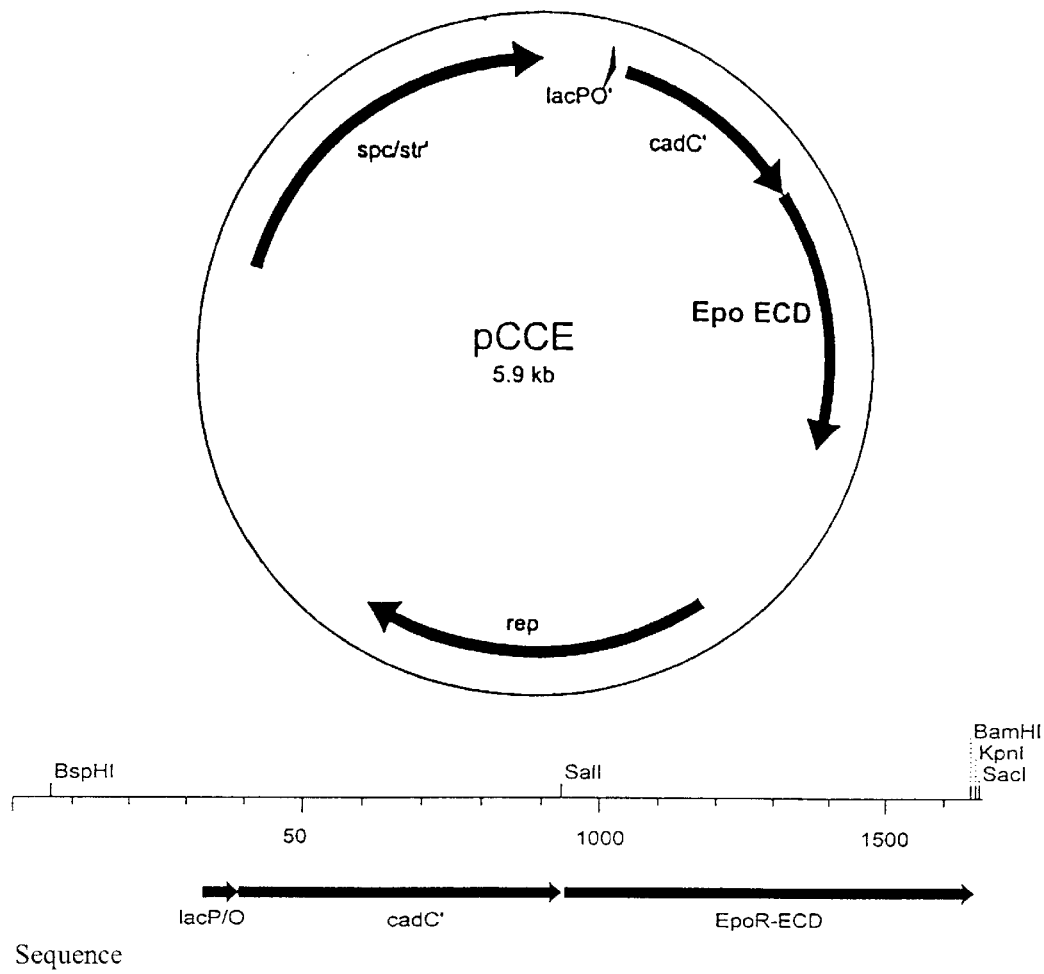

Sequence

```
GTCAAGTCTGCTTTAATTATTTTTAAGCGTGCATAATAAGCCCTACACAAATTGGGANGATATATCATGAA
AGGCTGGCTTTTTCTTGTTATCGCAATAGTTGGNGAAGTAATCGCAACATCCGCATTAAAATCTAGCGAGG
GCTTTACTAAGCTCGCGTTGGCCGATTCATTAATGCAGCTGGCACGACAGGTTTCCCGACTGGAAAGCGGG
CAGTGAGCGCAACGCAATTAATGTGAGTTAGCTCACTCATTAGGCACCCCAGGCTTTACACTTTATGCTTC
CGGCTCGTATGTTGTGTGGAATTGTGAGCGGATAACAATTTCACACAGGAAACAGCTATGACCATGATTAC
GCCAAGCTTCATTCCCTTTTCGAATGAGTTTCTATTATGCAACAACCTGTAGTTCGCGTTGGCGAATGGCT
TGTTACTCCGTCCATAAACCAAATTAGCCGCAATGGGCGTCAACTTACCCTTGAGCCGAGATTAATCGATC
TTCTGGTTTTCTTTGCTCAACACAGTGGCGAAGTACTTAGCAGGGATGAACTTATCGATAATGTCTGGAAG
AGAAGTATTGTCACCAATCACGTTGTGACGCAGAGTATCTCAGAACTACGTAAGTCATTAAAAGATAATGA
TGAAGATAGTCCTGTCTATATCGCTACTGTACCAAAGCGCGGCTATAAATTAATGGTGCCGGTTATCTGGT
ACAGCGAAGAAGAGGGAGAGGAAATAATGCTATCTTCGCCTCCCCCTATACCAGAGGCGGTTCCTGCCACA
GATTCTCCCTCCCACAGTCTTAACATTCAAAACACCGCAACGCCACCTGAACAATCCCCAGTTAAAAGCAA
ACGATTCACTACCTTTTGGGTATGGTTTTTTTTCCTGTTGTCGTTAGGTATCTGTGTAGCACTGGTAGCGT
TTTCAAGTCTGTCGACCATGGACCACCTCGGGGCGTCCCTCTGGCCCCAGGTCGGCTCCCTTTGTCTCCTG
CTCGCTGGGGCCGCCTGGGCGCCCCCGCCTAACCTCCCGGACCCCAAGTTCGAGAGCAAAGCGGCCTTGCT
GGCGGCCCGGGGCCCGAAGAGCTTCTGTGCTTCACCGAGCGGTTGGAGGACTTGGTGTGTTTCTGGGAGG
AAGCGGCGAGCGCTGGGGTGGGCCCGGGCAACTACAGCTTCTCCTACCAGCTCGAGGATGAGCCATGGAAG
CTGTGTCGCCTGCACCAGGCTCCCACGGCTCGTGGTGCGGTGCGCTTCTGGTGTTCGCTGCCTACAGCCGA
CACGTCGAGCTTCGTGCCCCTAGAGTTGCGCGTCACAGCAGCCTCCGGCGCTCCGCGATATCACCGTGTCA
TCCACATCAATGAAGTAGTGCTCCTAGACGCCCCCGTGGGGCTGGTGGCGCGGTTGGCTGACGAGAGCGGC
CACGTAGTGTTGCGCTGGCTCCCGCCGCCTGAGACACCCATGACGTCTCACATCCGCTACGAGGTGGACGT
CTCGGCCGGCAACGGCGCAGGGAGCGTACAGAGGGTGGAGATCCTGGAGGGCCGCACCGAGTGTGTGCTGA
GCAACCTGCGGGGCCGGACGCGCTACACCTTCGCCGTCCGCGCGCGTATGGCTGAGCCGAGCTTCGGCGGC
TTCTGGAGCTAGGATCCCCGGGTACCGAGCTCG
```

FIG. 7A

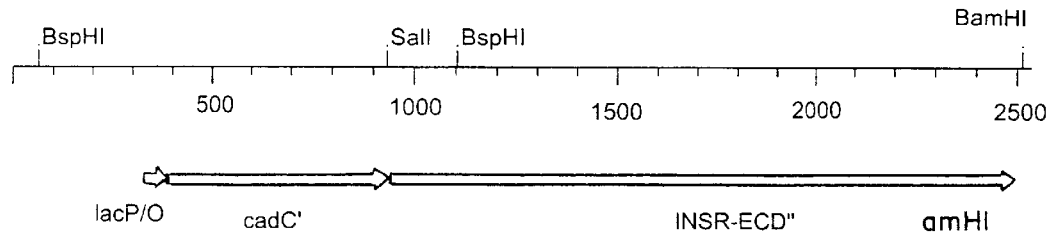

Sequence

```
GTCAAGTCTGCTTTAATTATTTTTAAGCGTGCATAATAAGCCCTACACAAATTGGGANGATATATCATGAA
AGGCTGGCTTTTTCTTGTTATCGCAATAGTTGGNGAAGTAATCGCAACATCCGCATTAAAATCTAGCGAGG
GCTTTACTAAGCTCGCGTTGGCCGATTCATTAATGCAGCTGGCACGACAGGTTTCCCGACTGGAAAGCGGG
CAGTGAGCGCAACGCAATTAATGTGAGTTAGCTCACTCATTAGGCACCCCAGGCTTTACACTTTATGCTTC
CGGCTCGTATGTTGTGTGGAATTGTGAGCGGATAACAATTTCACACAGGAAACAGCTATGACCATGATTAC
GCCAAGCTTCATTCCCTTTTCGAATGAGTTTCTATTATGCAACAACCTGTAGTTCGCGTTGGCGAATGGCT
TGTTACTCCGTCCATAAACCAAATTAGCCGCAATGGGCGTCAACTTACCCTTGAGCCGAGATTAATCGATC
TTCTGGTTTTCTTTGCTCAACACAGTGGCGAAGTACTTAGCAGGGATGAACTTATCGATAATGTCTGGAAG
AGAAGTATTGTCACCAATCACGTTGTGACGCAGAGTATCTCAGAACTACGTAAGTCATTAAAAGATAATGA
TGAAGATAGTCCTGTCTATATCGCTACTGTACCAAAGCGCGGCTATAAATTAATGGTGCCGGTTATCTGGT
ACAGCGAAGAAGAGGGAGAGGAAATAATGCTATCTTCGCCTCCCCTATACCAGAGGCGGTTCCTGCCACA
GATTCTCCCTCCCACAGTCTTAACATTCAAAACACCGCAACGCCACCTGAACAATCCCCAGTTAAAAGCAA
ACGATTCACTACCTTTTGGGTATGGTTTTTTTTCCTGTTGTCGTTAGGTATCTGTGTAGCACTGGTAGCGT
TTTCAAGTCTGTCGACCCACCTGTACCCCGGAGAGGTGTGTCCCGGCATGGATATCCGGAACAACCTCACT
AGGTTGCATGAGCTGGAGAATTGCTCTGTCATCGAAGGACACTTGCAGATACTCTTGATGTTCAAAACGAG
GCCCGAAGATTTCCGAGACCTCAGTTTCCCCAAACTCATCATGATCACTGATTACTTGCTGCTCTTCCGGG
TCTATGGGCTCGAGAGCCTGAAGGACCTGTTCCCCAACCTCACGGTCATCCGGGGATCACGACTGTTCTTT
AACTACGCGCTGGTCATCTTCGAGATGGTTCACCTCAAGGAACTCGGCCTCTACAACCTGATGAACATCAC
CCGGGGTTCTGTCCGCATCGAGAAGAACAATGAGCTCTGTTACTTGGCCACTATCGACTGGTCCCGTATCC
TGGATTCCGTGGAGGATAATCACATCGTGTTGAACAAAGATGACAACGAGGAGTGTGGAGACATCTGTCCG
GGTACCGCGAAGGGCAAGACCAACTGCCCCGCCACCGTCATCAACGGGCAGTTTGTCGAACGATGTTGGAC
TCATAGTCACTGCCAGAAAGTTTGCCCGACCATCTGTAAGTCACACGGCTGCACCGCCGAAGGCCTCTGTT
GCCACAGCGAGTGCCTGGGCAACTGTTCTCAGCCCGACGACCCCACCAAGTGCGTGGCCTGCCGCAACTTC
TACCTGGACGGCAGGTGTGTGGAGACCTGCCCGCCCCGTACTACCACTTCCAGGACTGGCGCTGTGTGAA
CTTCAGCTTCTGCCAGGACCTGCACCACAAATGCAAGAACTCGCGGAGGCAGGGCTGCCACCAATACGTCA
TTCACAACAACAAGTGCATCCCTGAGTGTCCCTCCGGGTACACGATGAATTCCAGCAACTTGCTGTGCACC
CCATGCCTGGGTCCCTGTCCCAAGGTGTGCCACCTCCTAGAAGGCGAGAAGACCATCGACTCGGTGACGTC
TGCCCAGGAGCTCCGAGGATGCACCGTCATCAACGGGAGTCTGATCATCAACATTCGAGGAGGCAACAATC
TGGCAGCTGAGCTAGAAGCCAACCTCGGCCTCATTGAAGAAATTTCAGGGTATCTAAAAATCCGCCGATCC
TACGCTCTGGTGTCACTTTCCTTCTTCCGGAAGTTACGTCTGATTCGAGGAGAGACCTTGGAAATTGGGAA
CTACTCCTTCTATGCCTTGGACAACCAGAACCTAAGGCAGCTCTGGGACTGGAGCAAACACAACCTCACCA
CCACTCAGGGGAAACTCTTCTTCCACTATAACCCCAAACTCTGCTTGTCAGAAATCCACAAGATGGAAGAA
GTTTCAGGAACCAAGGGCGCCAGGAGAGAAACGACATTGCCCTGAAGACCAATGGGACAAGGCATCCTG
TGAAAATGAGTTACTTAAATTTTCTTACATTCGGACATCTTTTGACAAGATCTTGCTGAGATGGGAGCCGT
ACTGGCCCCCGACTTCCGAGACCTCTTGGGGTTCATGCTGTTCTACAAAGAGGCCCCTTATCAGAATGTG
ACGGAGTTCGATGGGCAGGATGCGTAGGATCCCCGGGTACCGAGCTCG
```

FIG. 8A2

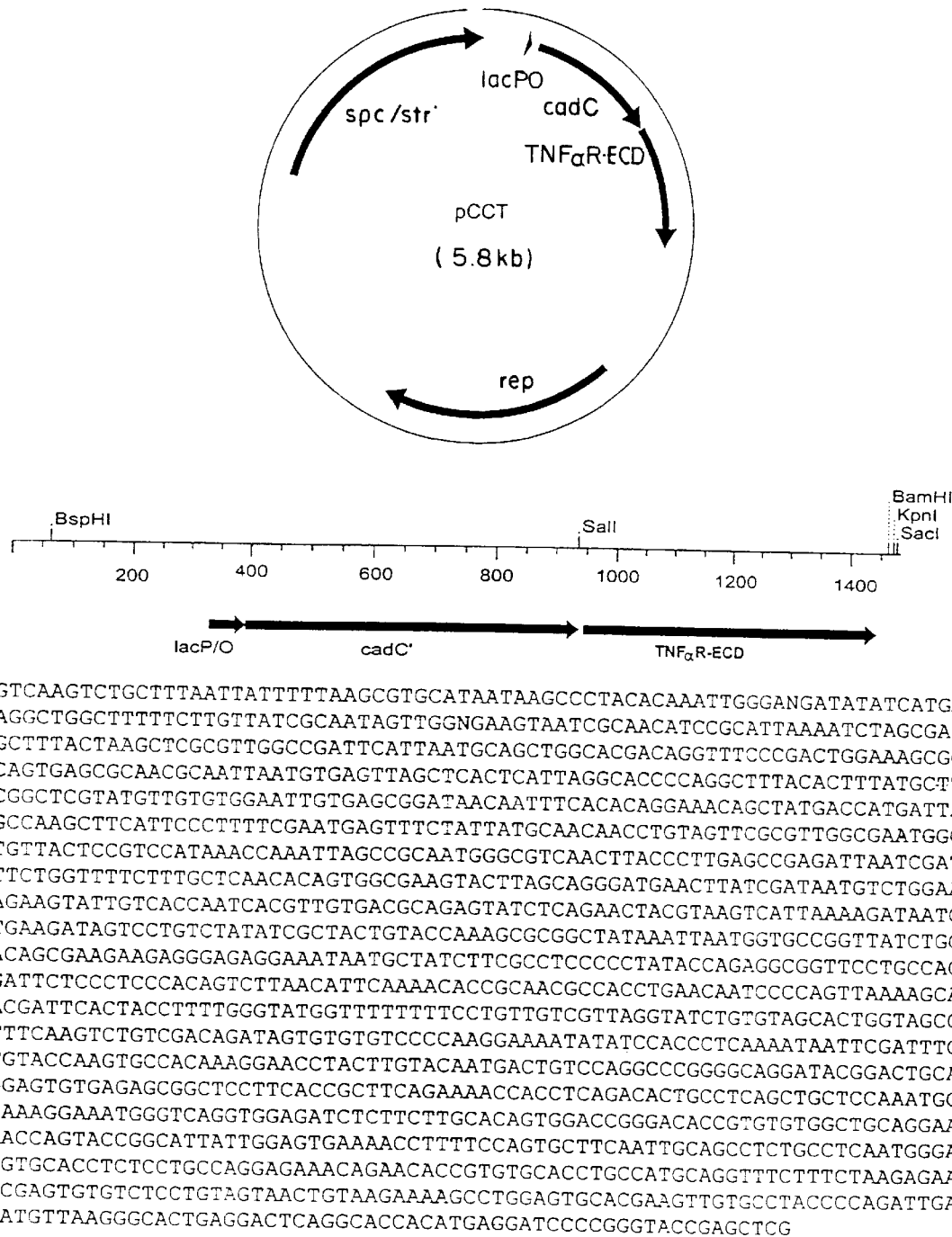

GTCAAGTCTGCTTTAATTATTTTTAAGCGTGCATAATAAGCCCTACACAAATTGGGANGATATATCATGAA
AGGCTGGCTTTTTCTTGTTATCGCAATAGTTGGNGAAGTAATCGCAACATCCGCATTAAAATCTAGCGAGG
GCTTTACTAAGCTCGCGTTGGCCGATTCATTAATGCAGCTGGCACGACAGGTTTCCCGACTGGAAAGCGGG
CAGTGAGCGCAACGCAATTAATGTGAGTTAGCTCACTCATTAGGCACCCCAGGCTTTACACTTTATGCTTC
CGGCTCGTATGTTGTGTGGAATTGTGAGCGGATAACAATTTCACACAGGAAACAGCTATGACCATGATTAC
GCCAAGCTTCATTCCCTTTTCGAATGAGTTTCTATTATGCAACAACCTGTAGTTCGCGTTGGCGAATGGCT
TGTTACTCCGTCCATAAACCAAATTAGCCGCAATGGGCGTCAACTTACCCTTGAGCCGAGATTAATCGATC
TTCTGGTTTTCTTTGCTCAACACAGTGGCGAAGTACTTAGCAGGGATGAACTTATCGATAATGTCTGGAAG
AGAAGTATTGTCACCAATCACGTTGTGACGCAGAGTATCTCAGAACTACGTAAGTCATTAAAAGATAATGA
TGAAGATAGTCCTGTCTATATCGCTACTGTACCAAAGCGCGGCTATAAATTAATGGTGCCGGTTATCTGGT
ACAGCGAAGAAGAGGGAGAGGAAATAATGCTATCTTCGCCTCCCCCTATACCAGAGGCGGTTCCTGCCACA
GATTCTCCCTCCCACAGTCTTAACATTCAAAACACCGCAACGCCACCTGAACAATCCCCAGTTAAAAGCAA
ACGATTCACTACCTTTTGGGTATGGTTTTTTTTCCTGTTGTCGTTAGGTATCTGTGTAGCACTGGTAGCGT
TTTCAAGTCTGTCGACAGATAGTGTGTGTCCCCAAGGAAAATATATCCACCCTCAAAATAATTCGATTTGC
TGTACCAAGTGCCACAAAGGAACCTACTTGTACAATGACTGTCCAGGCCCGGGGCAGGATACGGACTGCAG
GGAGTGTGAGAGCGGCTCCTTCACCGCTTCAGAAAACCACCTCAGACACTGCCTCAGCTGCTCCAAATGCC
GAAAGGAAATGGGTCAGGTGGAGATCTCTTCTTGCACAGTGGACCGGGACACCGTGTGTGGCTGCAGGAAG
AACCAGTACCGGCATTATTGGAGTGAAAACCTTTTCCAGTGCTTCAATTGCAGCCTCTGCCTCAATGGGAC
CGTGCACCTCTCCTGCCAGGAGAAACAGAACACCGTGTGCACCTGCCATGCAGGTTTCTTTCTAAGAGAAA
ACGAGTGTGTCTCCTGTAGTAACTGTAAGAAAGCCTGGAGTGCACGAAGTTGTGCCTACCCCAGATTGAG
AATGTTAAGGGCACTGAGGACTCAGGCACCACATGAGGATCCCCGGGTACCGAGCTCG

FIG. 9A

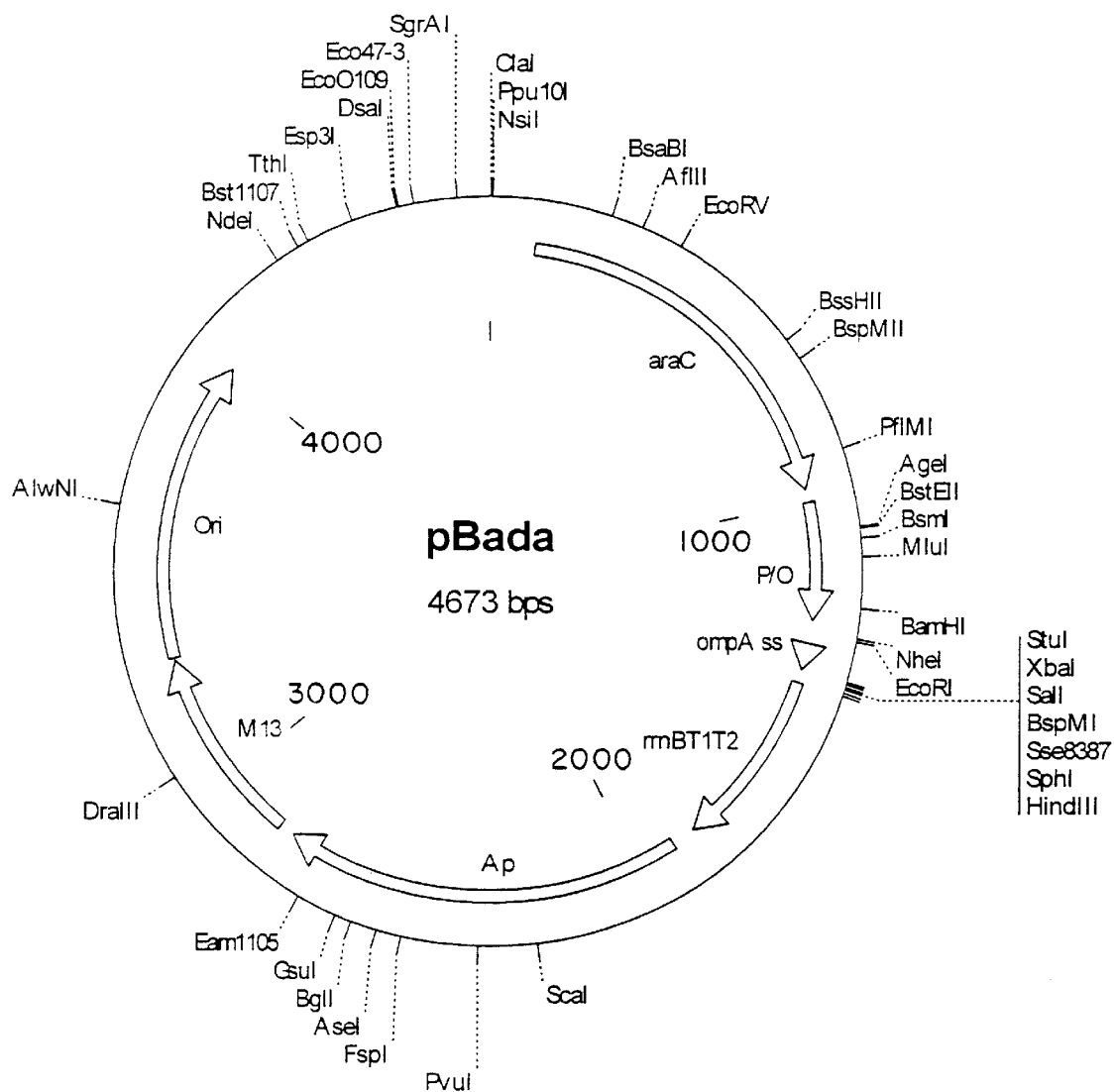
FIG. 10A1

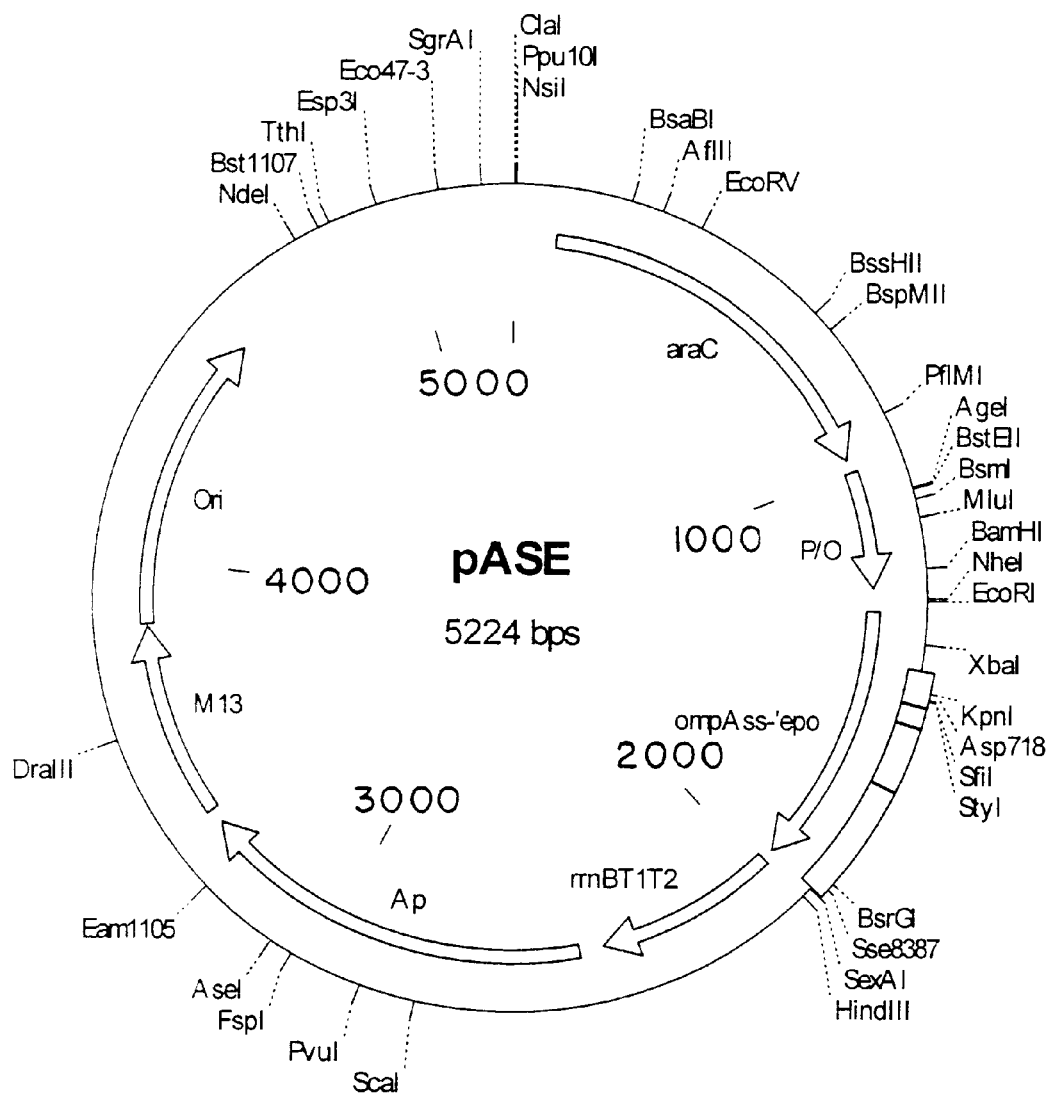
FIG.10A2

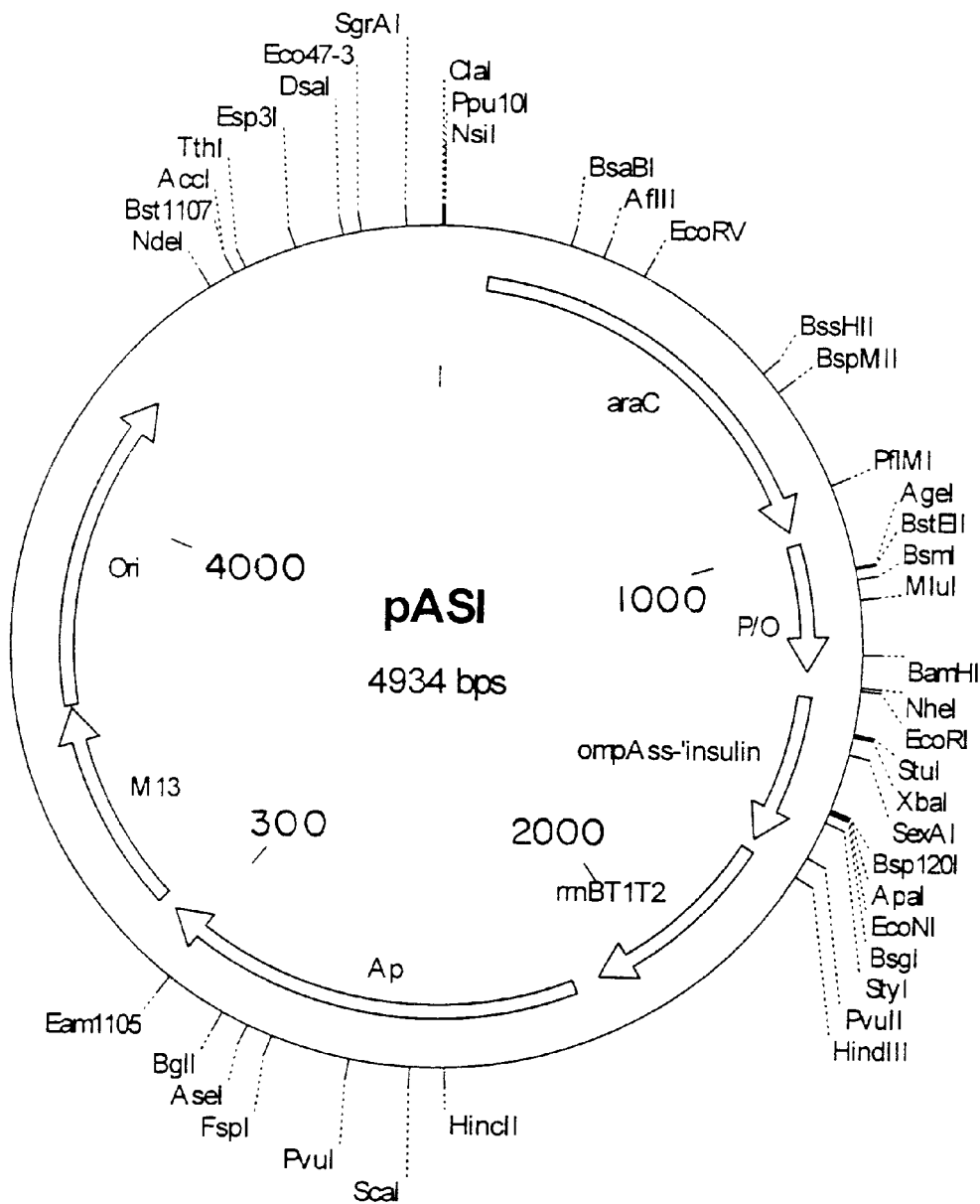
FIG. 10A3

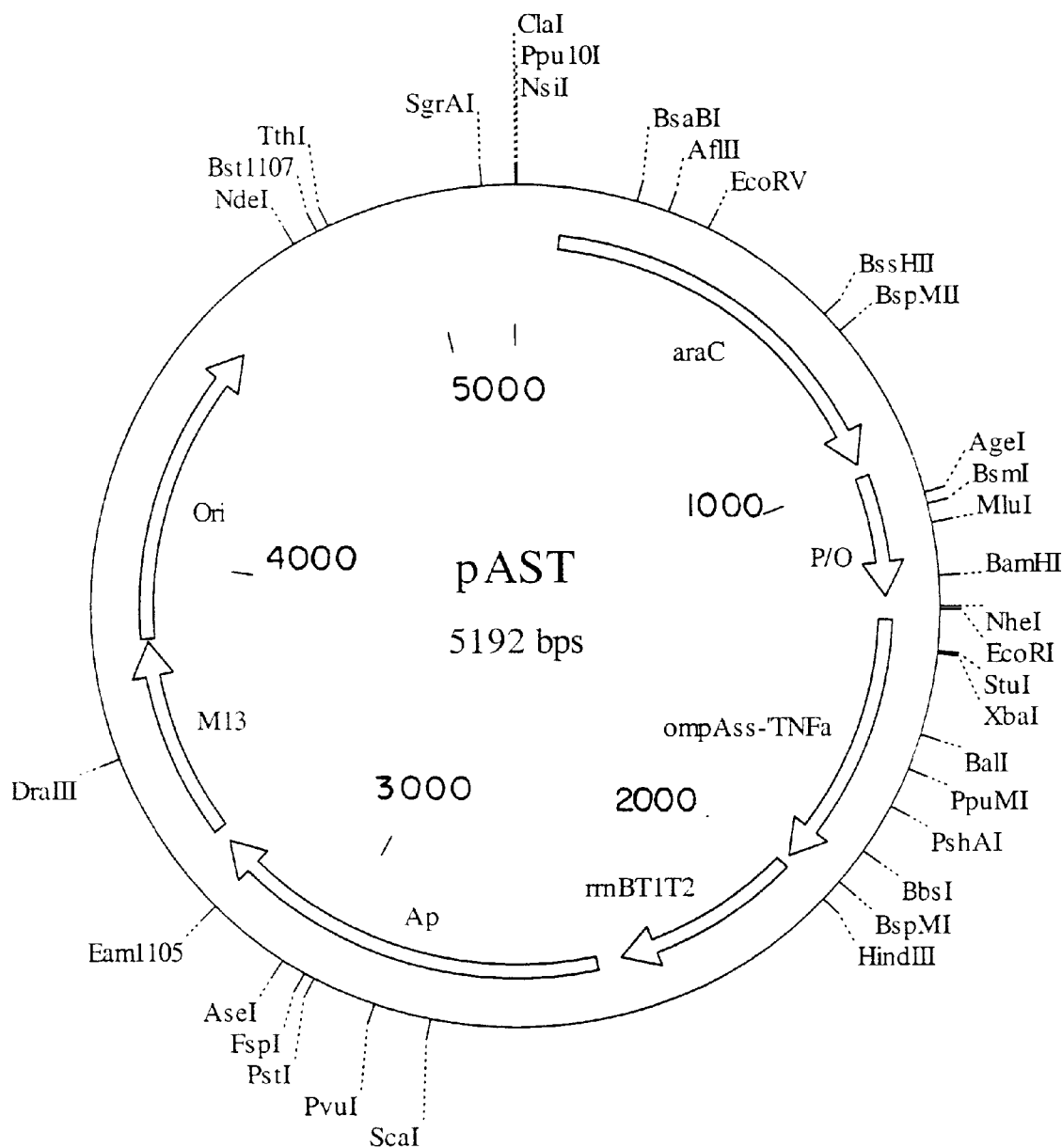
FIG. 10A4

METHODS AND COMPOSITIONS FOR IDENTIFYING AND MODULATING CTIONPROTEIN-INTERACTIONS

This application claims priority under 35 U.S.C. §119(e) to provisional patent application No. 60/064,058, filed Nov. 3, 1997, the entire contents of which is incorporated herein by reference in its entirety.

1. INTRODUCTION

The present invention relates to methods and compositions for the identification and modulation of protein-protein interactions. Specifically, the invention relates to methods and compositions for efficient, sensitive, high-throughput CadC-based screens for the identification of peptides involved in protein-protein interactions, including, but not limited to, peptides comprising amino acid sequences involved in receptor dimerization. The invention further relates to methods and compositions for efficient, sensitive, high-throughput CadC-based screens for compounds which modulate protein-protein interactions, such as, for example, modulation of interactions between protein sequences involved in receptor interactions, e.g., dimerization.

2. BACKGROUND OF THE INVENTION

All living cells possess the means to adapt to their environments. Cells rely, to a great extent, on extracellular molecules as a means by which to receive stimuli from their immediate environment. These extracellular signals are essential for the correct regulation of such diverse cellular processes as differentiation, contractility, secretion, cell growth, cell migration, contact inhibition and apoptosis. The external environmental signals received by the cell are transduced into the cell via activation of membrane-situated receptors. Activation of cell surface receptors is often dependent upon protein-protein interactions, including receptor-ligand binding, and receptor dimerization (homodimerization or heterodimerization) or oligomerization. Aberrant signalling can disrupt any of these cellular processes with detrimental results.

For reviews of signal transduction pathways see, e.g., Campbell, 1997, J. Pediat. 131:542–544; Hamilton, 1997, J. Leukoc. Biol. 62:145–155; Soede-Bobok & Touw, 1997, J. Mol. Med. 75:470–477; Heldin, 1995, Cell 80:213–223; Kishimoto et al. 1994, Cell 76:253–262; Miyajima, et al. 1992, Annu. Rev. Immunol. 10:295–331; and Cantley, et al. 1991, Cell 64:281–302.

Protein-protein interactions also play an important role in processes concerning many other cellular and viral proteins and enzymes, in addition to cell surface receptors. In some instances disruption of protein-protein interactions will lead to the loss of polypeptide function. In certain instances, loss of function of an enzyme may be therapeutically desirable. For example, the protease from HIV is a dimer (McKeever et al. 1989, J. Biol. Chem. 264:1919–1921) and the dimerization of the protein is required for function (Guenet et al. 1989, Eur. J. Pharmacol. 172:443–451, and Babe et al. 1992, Protein Sci. 10:1244–1253). Some candidate molecules (Zhang et al. 1991, J. Biol. Chem. 266:15591–15594 and Schramm et al. 1993, Biochem. Biophys. Res. Commun. 194:595–600) that block HIV protease function do so by disrupting dimerization.

Given the ubiquitous and important nature of protein-protein interactions in signal transduction pathways and in other cellular processes, compounds by which such interactions can be modulated would be very advantageous.

Attempts to identify ways to modulate such events have been reported. See, e.g., chimeric receptor studies reported by Schlessinger, and the chimeric signal transduction systems reported by Menzel et al. (utilizing heterologous Vibrio cholerae toxR in $E.$ $coli$; U.S. Pat. No. 5,521,066), Utsumi (utilizing a chimeric $E.$ $coli$ Tar protein; Utsumi et al. 1989, Science 245:1246–1249), Riedel (utilizing different eukaryotic hormone receptors in tissue culture; Riedel et al. 1989, EMBO J. 8:2943–2954) and Moe (utilizing a bacterial aspartate binding domain and the insulin receptor (Moe et al. 1989, Proc. Natl. Acad. Sci. USA 5 86:5683–5687). See also King et al. (U.S. Pat. Nos. 5,482,835 and 5,739,029; methods for screening for agonists and antagonists for G-protein coupled receptors). Each of these methods, however, exhibits significant limitations in either specificity, broad versatility and/or sensitivity.

Despite such reports, therefore, as yet, no efficient, sensitive, versatile high throughput procaryote-based system has yet been described for identifying protein-protein interactions or for identifying compositions for modulating such interactions.

3. SUMMARY OF THE INVENTION

The present invention relates to methods and compositions for the identification and modulation of protein-protein interactions.

Specifically, the invention relates, first, to methods and compositions for efficient, sensitive, high-throughput CadC-based screens for the identification of polypeptides involved in protein-protein interactions, such as, for example, dimerizing peptides, which include, but are not limited to, peptides comprising amino acid sequences involved in receptor dimerization. Such methods can also be utilized to identify peptide ligands which enhance a protein-protein interaction of interest. Such methods can, for example, be utilized in identifying ligands for orphan receptors.

The invention further relates to methods and compositions for efficient, sensitive, high-throughput CadC-based screens for compounds which modulate protein-protein interactions, such as, for example, modulation of interactions between protein sequences involved in receptor dimerization. Compounds identified via such methods can, for example, act as agonists or antagonists of a protein-protein interaction of interest, and/or can act as mimetics of natural ligands involved in the protein-protein interaction of interest.

The compositions of the present invention include, first, CadC-fusion polypeptides, which comprise, from carboxy-terminus to amino terminus, a periplasmic domain, a transmembrane domain and a CadC transcriptional regulatory domain. Interaction of CadC-fusion polypeptides results in CadC fusion polypeptides which activate RNA polymerase-dependent transcription from a cadBA regulatory region. While not wishing to be bound by any particular mechanism, it is believed that such interaction involves dimerization or multimerization of the CadC-fusion polypeptides, such interaction being dependent upon dimerization or multimerization of the CadC-fusion polypeptide periplasmic domains, and transcriptional activation involves binding of the dimerized or multimerized CadC-fusion polypeptides to the cadBA regulatory region.

It is to be understood that while the term "dimerization" is periodically used throughout the application for purposes of clarity and ease of description, interactions between the peptides of the invention can also be involved in the formation of trimers, tetramers and higher level oligomeric or multimeric polypeptide configurations.

"CadC," as used herein, can refer to *Escherichia coli* CadC nucleotide or amino acid sequences. Alternatively, "CadC" can refer to an Enterobacteriaceae family, e.g., *salmonella typhimurium*, homolog of *E. coli* CadC nucleotide or amino acid sequences.

Likewise, "cadBA," as used herein can refer to *E. coli* cadBA sequences. Alternatively, "cadBA" can refer to an Enterobacteriaceae family homologue of *E. coli* cadBA sequences.

It is also contemplated that CadC, cadBA and cells of the inventions can be derived from any procaryotic cell, other than *Vibrio cholerae*, exhibiting an inner membrane and periplasmic space.

A CadC-fusion polypeptide periplasmic domain can comprise a protein-protein interaction domain or a test domain.

A protein-protein interaction domain comprises an amino acid sequence which, under standard conditions utilized for cell (e.g., *E. coli*) culture, interacts with, that is, binds to, a peptide or polypeptide "partner." A test domain can comprise any amino acid sequence to be tested for an ability to exhibit such interaction.

Such interaction between two (or more) polypeptide domains is defined, identified and measured by the resultant activation of the CadC transcriptional regulatory domain and its activation of expression of cadBA-linked sequences. Such interactions can be homotypic or heterotypic interactions.

The protein-protein interaction domains of the invention can form dimers, trimers, or other oligomeric or multimeric (i.e., other higher-order aggregates) with one or more polypeptide partners. In instances in which the protein-protein interaction domain forms a dimer, the protein-protein interaction domain can be referred to as a "dimerization domain." Using the same convention, appropriate protein-interaction domains can, likewise, be referred to as trimerization domains, tetramerization domains, and so forth. For ease of discussion, and not by way of limitation, the term "dimerization domain" will, periodically, be utilized herein.

A CadC-fusion polypeptide transmembrane domain comprises any hydrophobic peptide domain which can act to anchor a CadC-fusion polypeptide to a procaryote, e.g., *E. coli*, inner membrane in such a manner that the CadC-fusion polypeptide periplasmic domain is present in the cell's periplasmic region and the transcriptional regulatory domain is inserted into the cell's cytoplasm.

A CadC-fusion polypeptide transcriptional regulatory domain (TRD) comprises a CadC amino acid sequence which, when part of an activated, e.g., dimerized, CadC-fusion polypeptide, can bind to and activate, i.e., stimulate RNA polymerase-driven transcription from, a cadBA regulatory region, e.g., a cadBA regulatory region within a native cadBA operon or within a cadBA reporter construct.

The present invention further relates to nucleic acid molecules encoding the CadC-fusion polypeptides of the invention. In one embodiment, such nucleic acid molecules are present as part of a plurality of nucleic acid molecules encoding CadC-fusion polypeptides representing a CadC-fusion polypeptide library.

Also included as part of the present invention are cells (e.g., *E. coli* or Enterobacteriaceae cells) comprising such CadC-fusion polypeptides and/or nucleic acid molecules encoding and capable of expressing such polypeptides. Preferably, the nucleic acid molecules can express variable levels of CadC-fusion polypeptides, including high-level expression sufficient to drive ligand-independent interaction (e.g., dimerization) of the CadC-fusion polypeptides. In instances in which interaction between a CadC-fusion polypeptide of interest can be enhanced by the presence of an additional peptide component (e.g., a peptide ligand) the cells of the invention can further comprise a nucleic acid sequence encoding the ligand or a candidate ligand test peptide operatively linked to a regulatory sequence that drives expression of the ligand or candidate ligand test peptide in the cell.

The present invention still further relates to CadC-based systems, said systems comprising a CadC-fusion polypeptide and/or nucleic acid molecule encoding the CadC-fusion polypeptide and a cadBA reporter construct. Such systems can, for example, comprise Enterobacterlaceae cells (e.g., *E. coli* or *S. typhimurium* cells) containing a CadC-fusion polypeptide and/or a nucleic acid molecule encoding a CadC-fusion polypeptide capable of being expressed in the cell and a cadBA reporter construct. In instances in which interaction between a CadC-fusion polypeptide of interest can be enhanced by the presence of an additional peptide component (e.g., a peptide ligand) the cells of the invention can further comprise a nucleic acid sequence encoding the ligand or a candidate ligand test peptide operatively linked to a regulatory sequence that drives expression of the ligand or candidate ligand in the cell. In one embodiment, CadC-based cell systems are present as a plurality of cells, wherein different individual cells express different CadC-fusion polypeptides and wherein such cells represent a CadC-fusion polypeptide library.

A cadBA reporter construct comprises a cadBA regulatory region operatively linked to a reporter gene sequence. A cadBA regulatory region comprises a cadBA nucleic acid sequence which is recognized by and binds to an activated CadC polypeptide transcriptional regulatory domain. Binding thereby activates RNA polymerase-driven transcription of the linked reporter gene sequence. A reporter gene sequence comprises a sequence which encodes a detectable gene product. In a preferred embodiment, the cadBA reporter construct is present within a cell at the native cadBA (or cadBA homolog) chromosomal location.

The CadC-based systems of the invention can represent completely native systems in which both the CadC amino acid sequences utilized as part of the CadC-fusion polypeptides and the cadBA regulatory sequences utilized as part of the cadBA reporter constructs are endogenous to the cell in which they are used.

In a preferred embodiment, one such CadC-fusion polypeptide system comprises an *E. coli* (e.g., *E. coli* K12) cell comprising a CadC-fusion polypeptide comprising *E. coli* CadC amino acid sequences and/or nucleic acid encoding such a CadC-fusion polypeptide, and a cadBA reporter construct comprising *E. coli* cadBA regulatory sequences.

In another preferred embodiment, one such CadC-fusion polypeptide system comprises a *Salmonella typhimurium* cell comprising a CadC-fusion polypeptide comprising *S. typhimurium* CadC homolog amino acid sequences and/or nucleic acid encoding such a CadC-fusion polypeptide, and a cadBA reporter construct comprising *S. typhimurium* cadBA homolog regulatory sequences.

The CadC-fusion polypeptide systems of the invention can also, for example, represent completely homologous ones in which CadC amino acid sequences utilized as part of the CadC-fusion polypeptides and the cadBA regulatory sequences utilized as part of the cadBA reporter constructs are derived from procaryotic cells of the family Enterobacteriaceae, as is the cell in which they can be found, but in which at least one component of the system (that is, CadC sequence, cadBA sequence or cell) is derived from a different cellular source than the rest.

In a preferred embodiment, such a CadC-fusion polypeptide system comprises an *E. coli* cell comprising a CadC-fusion polypeptide comprising *S. typhimurium* CadC amino acid sequences and/or nucleic acid encoding such a CadC-fusion polypeptide, and a cadBA reporter construct comprising either *E. coli* or *S. typhimurium* cadBA regulatory sequences.

In another preferred embodiment, such a CadC-fusion polypeptide system comprises a *S. typhimurium* cell comprising a CadC-fusion polypeptide comprising *E. coli* CadC amino acid sequences and/or nucleic acid encoding such a CadC-fusion polypeptide, and a cadBA reporter construct comprising either *E. coli* or *S. typhimurium* cadBA regulatory sequences.

The methods of the invention comprise, first, methods for the identification of protein-protein interactions, that is, methods for the identification of peptides which are involved in such interactions. These methods can be utilized for the identification of peptides involved in protein-protein interactions which represent homotypic or a heterotypic interactions. In instances wherein the protein-protein interaction of interest normally occurs in the presence of one or more ligands, such methods can successfully be performed either in the presence or absence of such ligands.

In one embodiment of such methods, the CadC-based systems of the invention can be utilized to identify a peptide partner involved in protein-protein interactions with a known peptide partner, that is, to identify peptide partners involved in heterotypic protein-protein interactions. In another embodiment of such methods, the CadC-based methods of the invention can be used to identify peptide sequences which undergo homotypic protein-protein interactions. In yet another embodiment, such methods can be utilized to identify peptide partners involved in heterotypic interactions in instances wherein none of the peptide partners involved in the protein-protein interaction are known.

The methods of the invention also include methods for the identification of ligands which enhance a protein-protein interaction of interest.

The methods of the invention further include methods for the identification of compounds which modulate protein-protein interactions. Such compounds can represent either agonists or antagonists of the protein-protein interaction of interest. In instances wherein the protein-protein interaction of interest normally occurs in the presence of one or more ligands, these methods can successfully be performed either in the presence or absence of such ligands.

In one embodiment, the methods of the invention can identify a ligand which enhances interaction (e.g., dimerization) between peptides of interest. Such a ligand can, for example, represent the naturally occurring ligand for a protein-protein interaction of interest (e.g., the natural ligand for an "orphan" receptor) or, alternatively, can represent a peptide or non-peptide ligand mimetic.

CadC is a dual functional single transmembrane receptor protein in *Escherichia coli* whose function is to sense environmental signals of pH and lysine and respond by modulating transcription from the cadBA operon. CadC is composed of three functional domains: a periplasmic sensing domain (PSD), a transmembrane domain (TMD) and a cytoplasmic transcriptional regulator domain (TRD). Results presented in the Example in Section 9.2, below, demonstrate for the first time that cadBA transcriptional activation requires interaction i.e., dimerization, between CadC periplasmic domains. This discovery has contributed to the development of the compositions and highly sensitive methods of the invention. The invention is further based, in part, on the discovery that a CadC-fusion polypeptide, as described above, can also successfully activate cadBA transcription in instances wherein the CadC-fusion polypeptide is a protein-protein interaction domain.

The CadC-based compositions and methods of the invention offer several advantages for the discovery of protein-protein interactions and compounds which modulate protein-protein interactions. First, for example, the systems of the invention are extremely sensitive in that background is surprisingly low and the magnitude of signal background is quite robust, such that even minor modulations in protein-protein interactions are readily detectable. Second, each of the components of the CadC-based systems of the invention are native or homologous to the cell in which the system is situated, as discussed above. Unlike heterologous systems (e.g., the ToxR system of Menzel & Taylor, supra) the systems of the invention circumvent problems which can be associated with, for example, improper folding and variable activation of heterologous transcriptional activation components, all thereby leading to inaccurate and insensitive results. Further, the native or homologous systems of the invention, unlike heterologous systems, reduce or eliminate the possibility that additional, auxiliary components necessary for a robust signal may be missing. Third, the native or homologous nature of the systems of the invention minimize the number of components which need to be cloned into the system, thereby providing maximum flexibility for manipulation of such systems.

4. BRIEF DESCRIPTION OF THE FIGURES

FIG. 1A. Diagram depicting *E. coli* wild-type cadBA transcription controlled by the *E. coli* wild-type cadC gene. As depicted in the diagram, interaction between copies of native CadC protein is influenced by such factors as lysine concentration and pH.

FIG. 1B. Diagram depicting the CadC-based protein-protein interaction detection system. In this embodiment of the system, an *E. coli* cell is depicted in which cadBA expression (monitored by Lac activity) responds to factors modulating the state of a CadC-fusion polypeptide. As depicted in the diagram, the cadBA reporter construct is present within the *E. coli* chromosome at the site of the wild-type cadBA operon. In addition, the cell depicted has had the native CadC gene inactivated so as to lower cadBA background expression.

FIG. 2. Diagram of the *E. coli* CadC amino acid sequence (SEQ ID NO:2). The transmembrane domain is boxed. The periplasmic domain is carboxy to the transmembrane domain, while the intracellular domain, which includes the transcriptional regulatory domain, is amino to the transmembrane region. Junctions 1, 2, 4 and 5 are as shown. See Section 9.1, e.g., for details regarding junctions.

FIG. 3. Diagram illustrating level-dependent interaction between CadC-fusion polypeptides. In this particular illustration, a CadC-fusion polypeptide is expressed in an inducible (lac) dependent manner, such that as higher levels of the lac inducer IPTG are introduced, the higher the level of CadC-fusion polypeptide is produced. Interaction in this example is a homotypic dimerization interaction between the CadC-fusion polypeptides, and is measured via the level of cadBA reporter signal detected. As shown in the diagram, an increase in the level of CadC-fusion polypeptides drives interaction between the polypeptides. Thus, even in instances wherein such interaction might normally be ligand-dependent, a high concentration of CadC-fusion polypeptide results in ligand-independent interaction.

FIG. 4A. Diagram illustrating effect of agonist and antagonist compounds on CadC-fusion polypeptide interactions. In this particular illustration, a CadC-fusion polypeptide is expressed in an inducible (lac) dependent manner, such that as higher levels of the lac inducer IPTG are introduced, a higher the level of CadC-fusion polypeptide is produced. Interaction in this example is a homotypic dimerization interaction between the CadC-fusion polypeptides, and is measured via the level of cadBA reporter signal detected.

FIG. 4B. Diagram illustrating the effects an agonist and an antagonist have on levels of cadBA reporter sequence expression.

FIG. 5. Depicts the pCCZ1 plasmid, a plasmid encoding a CadC-fusion polypeptide comprising a periplasmic domain containing a wild type GCN4 leucine zipper dimerization domain, and an *E. coli* CadC transmembrane domain and transcriptional regulatory domains. Relevant portions of the plasmid and coding sequences are schematically diagrammed. The figure also depicts the nucleotide sequence (SEQ ID NO:3) of the CadC-fusion polypeptide coding region extending from the lacOP sequence, thereby confirming the integrity of the plasmid construction.

FIG. 6. CadBA activity of CadC-fusion polypeptides generated with either junction 1 (pCCZ1-wt and pCCZ1-lp19) or junction 2 (pCCZ4-wt and pCCZ4-pl19). "wt" plasmids comprise sequences which encode wild type GCN4 leucine zipper domains, while "lp" plasmids comprise mutant, dimerization-defective GCN4 leucine zipper domains.

FIG. 7A. Depicts the plasmid pCCE, a plasmid encoding a CadC-fusion polypeptide comprising a periplasmic domain containing the extracellular domain of EpoR, and an *E. coli* CadC transmembrane domain and transcriptional regulatory domains. Relevant portions of the plasmid and coding sequences are schematically diagrammed. The figure also depicts the nucleotide sequence (SEQ ID NO:4) of the CadC-fusion polypeptide coding region extending from the lacOP sequence, thereby confirming the integrity of the plasmid construction.

FIG. 7B. The EpoR-containing CadC-fusion polypeptide supports robust cadBA transcription. pCCE expression is compared to that of pCCZ1-wt and inactive PCCZ-1-lp19 controls. Expression is depicted as a measure of cadBA transcriptional activity.

FIG. 7C. Depicts the plasmid PCCE-I, containing the lacI$^Q$ gene and encoding the EpoR-CadC-fusion polypeptide transcribed by the lac promoter, as shown in 5A.

FIG. 7D. IPTG-regulated expression of the EpoR-containing CadC-fusion polypeptide on PCCE-I. Expression is depicted as a measure of cadBA transcriptional activity.

FIG. 7E. Depicts the strategy for choosing an inducer (in this example, IPTG) concentration which is optimal for performing a screen to identify agonists (e.g., EPO functional mimetics) of the EPO/EPOR protein-protein interaction which utilizes the CadC-based cell system comprising pCCE-I.

FIG. 8A1. Depicts the plasmid PCCI, a plasmid encoding a CadC-fusion polypeptide comprising a periplasmic domain containing the extracellular domain of the insulin receptor, and an *E. coli* CadC transmembrane domain and transcriptional regulatory domains.

FIG. 8A2. Relevant portions of the plasmid and coding sequences are schematically diagrammed. The figure also depicts the nucleotide sequence (SEQ ID NO: 5) of the CadC-fusion polypeptide coding region extending from the lacOP sequence, thereby confirming the integrity of the plasmid construction.

FIG. 8B. The insulin receptor-containing CadC-fusion polypeptide supports robust CadBA transcription. pCCI expression is compared to that of pCCZ1-wt and inactive pCCZ-1-lp19 controls. Expression is depicted as a measure of cadBA transcriptional activity.

FIG. 8C. Depicts the plasmid pCCI-I, containing the lacI$^Q$ gene and encoding the insulin receptor-CadC-fusion polypeptide transcribed by the lac promoter, as shown in 6A.

FIG. 8D. IPTG-regulated expression of the insulin receptor-containing CadC-fusion polypeptide on pCCI-I. Expression is depicted as a measure of cadBA transcriptional activity.

FIG. 8E. Depicts the strategy for choosing an inducer (in this example, IPTG) concentration which is optimal for performing a screen to identify agonists (e.g., insulin functional mimetics) of the insulin/insulin receptor protein-protein interaction which utilizes the CadC-based cell system comprising PCCI-I.

FIG. 9A. Depicts the plasmid pCCT, a plasmid encoding a CadC-fusion polypeptide comprising a periplasmic domain containing the extracellular domain of the receptor for TNFα (TNFαR), and an *E. coli* CadC transmembrane domain and transcriptional regulatory domains. Relevant portions of the plasmid and coding sequences are schematically diagrammed. The figure also depicts the nucleotide sequence (SEQ ID NO:6) of the CadC-fusion polypeptide coding region extending from the lacOP sequence, thereby confirming the integrity of the plasmid construction.

FIG. 9B. The TNFαR-containing CadC-fusion polypeptide supports robust CadBA transcription. PCCT expression is compared to that of pCCZ1-wt and inactive PCCZ-1-lp19 controls. Expression is depicted as a measure of cadBA transcriptional activity.

FIG. 9C. Depicts the plasmid PCCT-I, containing the lacI$^Q$ gene and encoding the TNFαR-CadC-fusion polypeptide transcribed by the lac promoter, as shown in 7A.

FIG. 9D. IPTG-regulated expression of the TNFαR-containing CadC-fusion polypeptide on pCCT-I. Expression is depicted as a measure of cadBA transcriptional activity.

FIG. 9E. Depicts the strategy for choosing an inducer (in this example, IPTG) concentration which is optimal for performing a screen to identify antagonists of the TNFα/TNFα receptor protein-protein interaction which utilizes the CadC-based cell system comprising pCCT-I.

FIGS. 10A1–4. Depicts the Ligand/ CadC-fusion chimera co-expression system, in particular, the figure depicts plasmid vectors used to express ligands targeted to the periplasmic space.

Figure 3:
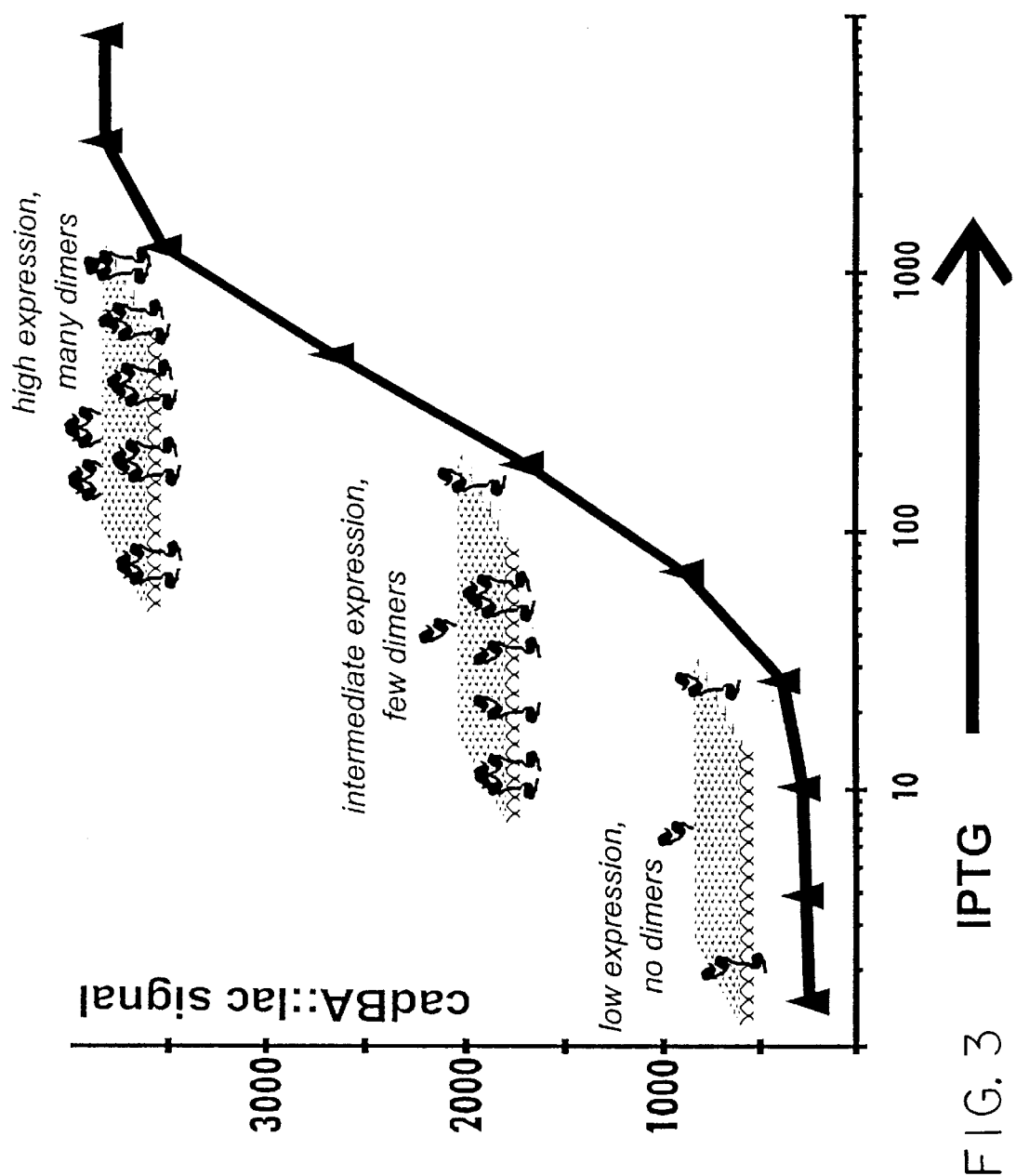

TNF-α specifically induces expression of this fusion when low level endogenous expression of the ligands is employed (10D), but specificity is lessened when higher level expression of the co-expression is induced (10E).

5. DETAILED DESCRIPTION OF THE INVENTION

CadC is a dual functional single transmembrane receptor protein in *Escherichia coli* whose function is to sense environmental signals of pH and lysine and respond by modulating transcription from the cadBA operon (Meng et al., 1999, J. Bacteriol. 174:2670–78; Neely et al., 1994, J. Bacteriol. 176:3278–85; Watson et al., 1992, J. Bacteriol. 174: 530–540; Dell et al., 1994, Microbiology 14:7–16). CadC is composed of three functional domains: a periplasmic sensing domain (PSD), a transmembrane domain (TMD) and a cytoplasmic transcriptional regulator domain (TRD). Results presented in the Example in Section 9.2, below, demonstrate for the first time that cadBA transcriptional activation requires interaction i.e., dimerization, between CadC periplasmic domains. This discovery has contributed to the development of the compositions and highly sensitive methods of the invention. The invention is further based, in part, on the discovery that a CadC-fusion polypeptide , as described above, can also successfully activate cadBA transcription in instances wherein the CadC-fusion polypeptide is a protein-protein interaction domain.

The CadC-based systems of the present invention comprise CadC-fusion polypeptides and a cadBA reporter construct. Upon interaction of the protein-protein interaction domain of the CadC-fusion polypeptide with a partner, the CadC-fusion polypeptide becomes activated such that it activates RNA polymerase-dependent transcription from a cadBA regulatory region within the cadBA reporter construct, thereby driving linked reporter gene expression. In this manner, reporter expression can be measured to determine the level of functional CadC-fusion protein interaction, e.g., dimerization.

Described below, are compositions and methods relating to such CadC-based systems. In particular, Sections 5.1, 5.2, and 5.3 describe CadC compositions of the invention, including cadBA reporter constructs, CadC-fusion polypeptides, nucleic acid molecules encoding such compositions, cells comprising such compositions, and libraries comprising such compositions. Sections 5.4 and 5.5, below, describe CadC-based methods of the invention, including methods for the identification of protein-protein interactions and methods or the identification of compounds which modulate protein-protein interactions.

5.1. cadBA REPORTER CONSTRUCTS

The CadC-based systems of the invention comprise a cadBA reporter construct whose expression is dependent upon its interaction with (e.g., binding of) an activated CadC transcriptional regulatory domain. In particular, a CadC-reporter construct comprises a cadBA regulatory region operatively linked to a reporter gene sequence such that activation of transcription from the cadBA regulatory region results in expression of the reporter gene sequence. In cells, the CadC reporter construct is preferably present in a single-copy form which is integrated into the chromosome at the position of the endogenous cadBA sequence.

The cadBA regulatory region comprises a cadBA nucleic acid sequence which is recognized by and interacts with (binds to) an activated CadC transcriptional regulatory domain. Binding then activates RNA polymerase-driven transcription of the linked reporter gene sequence. In general, the cadBA regulatory region can comprise any cadBA operon nucleotide sequence to which activated CadC transcriptional regulatory domains can bind and activate RNA polymerase-driven transcription.

Identification of a cadBA operon nucleotide sequence which can be utilized as a cadBA transcriptional regulatory domain can routinely be accomplished. For example, a nucleotide sequence encoding a detectable gene product (e.g., a reporter gene sequence) can be operatively linked, via standard recombinant genetic techniques, downstream of at least a portion of the cadBA operon. Activated CadC-dependent expression of the detectable gene product can then be assayed. Expression of the detectable gene product in a CadC-dependent fashion indicates that the cadBA operon sequences upstream of the nucleotide sequence encoding the detectable gene product can act as a cadBA regulatory region.

"cadBA," as used herein can refer to *Escherichia coli* (for example *E. coli* K12), cadBA sequences. In *E. coli*, the sequence of the cadBA operon is well known (Meng & Bennet, 1992, J. Bact. 174:2659–69, which is' incorporated herein by reference in its entirety). *E. coli* cadBA sequences utilized herein can also comprise nucleotide sequences of allelic variants of the cadBA sequences described above.

Such allelic variants should be functional variants, at least to the extent that they can be activated by activated CadC and can drive RNA-polymerase-dependent transcription. Allelic variants can routinely be identified and obtained using standard recombinant DNA techniques (see e.g., Methods in Enzymology, 1987, volume 154, Academic Press; Sambrook et al., 1989, Molecular Cloning—A Laboratory Manual, 2nd Edition, Cold Spring Harbor Press, New York; and Ausubel et al., Current Protocols in Molecular Biology, Greene Publishing Associates and Wiley Interscience, New York).

In general, nucleic acids comprising such allelic variants should be able to hybridize to the nucleotide sequence, or the complement thereof, of the cadBA sequences described above under moderately stringent hybridization conditions (using, for e.g., standard Southern blotting hybridization conditions, with the final wash in 0.2×SSC/0.1% SDS at 42° C.; Ausubel et al., eds., 1989, Current Protocols in Molecular Biology, Vol. I, Green Publishing Associates, Inc., and John Wiley & sons, Inc., New York, at p. 2.10.3), or highly stringent hybridization conditions (using, e.g., standard Southern blotting hybridization conditions, with the final wash in 0.1×SSC/0.1%SDS at 68° C.; Ausubel et al., supra). Further, such allelic variants should map to the same locus as the *E. coli* cadBA sequences described above.

In *E. coli*, approximately 400 base pairs lie between the end of the cadC gene and the start of the cadB coding region. In one embodiment, the cadBA regulatory region comprises this approximately 400 base pair region. In another embodiment, the cadBA regulatory region can further comprise the nucleotide sequence upstream of the cadA coding region, e.g., the sequence between the cadB and the cadA coding regions. An exemplary cadBA regulatory region is described and utilized in the working example presented in Section 6, below.

Alternatively, "cadBA" can refer to an Enterobactriaceae family homologue of *E. coli* cadBA sequences, wherein such sequences can interact with and activate CadC polypeptides and drive RNA polymerase-dependent transcription. Members of the family Enterobacteriaceae include, but are not limited to, species of Escherichia, Salmonella, Citrobacter, Klebsiellae, and Proteus. Such a cadBA homolog is, generally, a sequence present in a chromosomal segment homologous to the sector of the *E. coli* chromosomal region containing the cadBA operon, and which, upon interacting with (e.g., binding to) an activated CadC transcriptional regulatory domain drives RNA polymerase-dependent transcription. In general, such homologs can hybridize under moderately or highly stringent hybridization conditions as described above, to the nucleotide sequence of an *E. coli* cadBA operon regulatory region.

A CadC-responsive "reporter gene" sequence can comprise any gene sequence which expresses or encodes a detectable gene product (RNA or protein). Such a gene product is detectable either by its presence, or by its activity that results in the generation of a detectable signal. A reporter gene is used in the invention to monitor the ability of a test compound to activate the CadC transcriptional regulatory domain.

A variety of reporter gene sequences well known to those of skill in the art can be utilized. For convenience, enzymatic reporters and light-emitting reporters analyzed by colorometric or fluorometric assays are preferred for the screening assays of the invention. Such reporter genes include, but are not limited to β-galactosidase (Nolan et al. 1988, Proc. Natl. Acad. Sci. USA 85:2603–07), β-glucuronidase (Roberts et al. 1989, Curr. Genet. 15:177–180), luciferase (Miyamoto et al., 1987, J. Bacteriol. 169:247–253), or β-lactamase.

In one embodiment, the reporter gene sequence comprises a nucleotide sequence which encodes a LacZ gene product, β-galactosidase. The enzyme is very stable and has a broad specificity so as to allow the use of different histochemical, chromogenic or fluorogenic substrates, such as, but not limited to, 5-bromo-4-chloro-3-indoyl-β-D-galactoside (X-gal), lactose 2,3,5-triphenyl-2H-tetrazolium (lactose-tetrazolium), and fluorescein galactopyranoside (see Nolan et al., 1988, supra). An example of the construction of the cadB'-lacZ$^+$ reporter strain is described in the example presented in Section 8, below, while the Examples presented in Sections 9.2, 10, 11, and 12 demonstrate the successful measurement of such reporter gene sequences to assay CadC-fusion polypeptide interactions.

In another embodiment, the product of the *E. coli* β-glucuronidase gene (GUS) can be used as a reporter gene (Roberts et al. 1989, Curr. Genet. 15:177–180). GUS activity can be detected by various histochemical and fluorogenic substrates, such as X-glucuronide (Xgluc), and 4-methylumbelliferyl glucuronide.

A variety of bioluminescent, chemiluminescent and fluorescent proteins can also be used as light-emitting reporters in the invention. One type of such reporter, enzymes that require cofactor(s) to emit light, include but are not limited to, the bacterial luciferase (LUX, 1989, Biochim. Biophys. Acta 1007:84–90), and the firefly luciferase from Photinus pyralis (De Wet et al., 1987, Mol. Cell. Biol. 7:725–737), which can be assayed by light production (Miyamoto et al., 1987, J. Bacteriol. 169:247–253; Loessner et al. 1996, Environ. Microbiol. 62:1133–1140; and Schultz & Yarus, 1990, J. Bacteriol. 172:595–602).

Other types of light-emitting reporter, which does not require substrates or cofactors, include but are not limited to the wild-type green fluorescent protein (GFP) of Victoria aequoria (Chalfie et al. 1994, Science 263:802–805), and modified GFPs (Heim et al. 1995, Nature 373:663–4; PCT publication WO 96/23810). Transcription and translation of this type of reporter gene leads to the accumulation of the fluorescent protein in test cells, which can be measured by a fluorimeter, or a flow cytometer, for example, by methods that are well known in the art (see, e.g., Lackowicz, 1983, Principles of Fluorescence Spectroscopy, Plenum Press, New York).

In addition to reporter gene sequences such as those described above, which provide convenient calorimetric responses, other reporter gene sequences, such as, for example, selectable reporter gene sequences, can routinely be employed. For example, the coding sequence for chloramphenicol transacetylase (CAT) can be utilized, leading to CadC-fusion polypeptide-dependant expression of chloramphenicol resistant growth on agar surfaces. The use of CAT and the advantages of a selectable reporter gene are well known to those skilled in the art (Eikmanns et al. 1991, Gene 102:93–98). Other selectable reporter gene sequences can also be utilized and include, but are not limited to gene sequences encoding polypeptides which confer zeocin (Hegedus et al. 1998, Gene 207:241–249) or kanamycin resistance (Friedrich & Soriano, 1991, Genes. Dev. 5:1513–1523).

cadBA reporter constructs can be constructed according to standard recombinant DNA techniques (see e.g., Methods in Enzymology, 1987, volume 154, Academic Press; Sambrook et al. 1989, Molecular Cloning—A Laboratory Manual, 2nd Edition, Cold Spring Harbor Press, New York; and Ausubel et al. Current Protocols in Molecular Biology, Greene Publishing Associates and Wiley Interscience, New York, each of which is incorporated herein by reference in its entirety).

Standard procaryotic homologous recombination techniques well known to those of skill in the art can be utilized for integration of the cadBA reporter constructs into the bacterial chromosome at the site of the endogenous cadBA operon. Such insertions can be constructed using general gene transfer techniques including transformation, conjugation, or transduction. In particular, such techniques can, for example, include, but are not limited to, P1 transduction, λ lysogeny, and Mu transposition and conjugation (see Miller, J. H., 1992, A Short Course in Bacterial Genetics, Cold Spring Harbor Laboratory Press, NY; Neidhardt, F. C., ed., 1987, *Escherichia coli* and *Salmonella typhimurium*, American Society for Microbiology, Washington, D.C.; Yarmolinsky, M. B. & Sternberg, N., 1988, pp. 291–438, in Vol. 1 of *The Bacteriophages*, R. Calendar, ed., Plenum Press, New York, each of which is incorporated herein by reference in its entirety).

The Example presented in Sections 6 and 8, below, describes the construction of cadBA reporter constructs and their use in the generation of cadBA reporter-containing strains.

Depending on the reporter gene sequence utilized as part of the cadBA reporter construct, the cells of the invention comprising such cadBA reporter constructs may also require a loss-of-function allele of the reporter gene. For example, in instances in which a lacZ reporter gene sequence is utilized, cells of a lacZ$^-$ strain should be used. Such strains are well known and available in the art, for example from private laboratories, such as the *E. coli* and Salmonella genetic stock center or other public collections (*E. coli* stock center (CGSC), Yale University, New Haven, Conn.; Salmonella Genetic Stock Center, University of Calgary, Calgary, Alberta, Canada; American Type Culture Collection (ATCC), Manassas, Va.; or Northern Regional Research Laboratory (NRRL), Peoria, Ill.), or from commercial suppliers. For example, an *E. coli* strain with an integrated cadBA-lac reporter and cadC::Tn10 can be utilized when lacZ reporter gene sequences are to be utilized. Among the preferred *E. coli* strains are RFM443 (Drolet et al., 1995, Proc. Natl. Acad. Sci USA 92:3526–3530) and JM109 (Promega; Madison, Wis.) derivatives, in that such strains exhibit sizable IPTG induction values (See, e.g., the example presented in Section 10, below).

5.2. CadC-FUSION POLYPEPTIDES

Described herein are the CadC-fusion polypeptides of the invention. Such CadC-fusion polypeptides comprise, from carboxy-terminus to amino-terminus, a periplasmic domain, a transmembrane domain, and a CadC transcriptional regulatory domain.

The CadC-fusion polypeptides of the invention comprise CadC amino acid sequences, as described herein. In particular, the CadC-fusion polypeptides of the invention comprise a portion (that is, at least the CadC DNA binding domain), but do not consist of an entire, native CadC protein.

"CadC," as used herein, can refer, first, to *E. coli*, e.g., *E. coli* K12, CadC. The *E. coli* CadC amino acid and nucleotide sequences are well known. See, e.g., the amino acid sequence of a wild type *E. coli* CadC presented in FIG. 2. *E. coli* CadC amino acid sequences utilized in the CadC-fusion polypeptides of the invention can also comprise amino acid sequences encoded by any allelic variants of the CadC polypeptide shown in FIG. 2. Such allelic variants should be functional variants, at least to the extent that they exhibit CadC DNA binding activity. Allelic variants can routinely be identified and obtained using standard recombinant DNA techniques (see e.g., Methods in Enzymology, 1987, volume 154, Academic Press; Sambrook et al., 1989, Molecular Cloning—A Laboratory Manual, 2nd Edition, Cold Spring Harbor Press, New York; and Ausubel et al., Current Protocols in Molecular Biology, Greene Publishing Associates and Wiley Interscience, New York).

In general, nucleic acid encoding such allelic variants should be able to hybridize to the complement of the coding sequence of CadC under moderately stringent conditions (using, e.g., standard Southern blotting hybridization conditions, with the final wash in 0.2×SSC/0.1% SDS at 42° C.; Ausubel et al., eds., 1989, Current Protocols in Molecular Biology, Vol. I, Green Publishing Associates, Inc., and John Wiley & sons, Inc., New York, at p. 2.10.3), or highly stringent hybridization conditions (using, e.g., standard Southern blotting hybridization conditions with the final wash in 0.1×SSC/0.1%SDS at 68° C.; Ausubel et al., supra.). Further, such allelic variants should map to the same locus as the *E. coli* cadC gene depicted in FIG. 2. Finally, the alleles should encode a gene product functionally equivalent to a cadC gene product. That is, the gene product should be able to activate RNA polymerase-dependent transcription from cadBa regulatory sequences.

"CadC," as used herein can also include a CadC homolog derived from procaryotic cells of the family Enterobacteriaceae. Members of the family Enterobacteriaceae include, but are not limited to species of Escherichia, Salmonella, Citrobacter, Klebsiellae, and Proteus. Such a CadC homolog is, generally, one which is encoded by a gene present in a chromosomal segment homologous to the sector of the *E. coli* chromosomal region containing the cadC gene, and which encodes a protein exhibiting interaction-dependent (e.g., dimerization-dependent) DNA binding activity. Further, nucleic acid molecules encoding such cadC homologues should be able to hybridize under moderately stringent or highly stringent (see supra) conditions to the nucleotide sequence of an *E. coli* cadC gene, and/or encode a polypeptide greater than about 50% identity to the *E. coli* cadC polypeptide across the entire sequence and/or greater than about 80% identity across the DNA binding portions of the polypeptide homolog (that is, the portion of the polypeptide sharing homology with the OmpR class transcriptional activators (e.g., PhoB) of bacteria (see, e.g., Martinez-Hackert & Stock, 1997, J. Mol. Biol. 69:301–312). Methods and/or algorithms for routinely identifying such sequences are well known to those of skill in the art.

CadC homologs can routinely be identified and obtained using standard procaryotic genetic and recombinant DNA techniques (see e.g., Sambrook et al., supra., and Ausubel et al., supra). Recombinant DNA may be obtained from a cloned genomic or cDNA library, or by PCR amplification. For example, a genomic library may be produced by standard molecular biological techniques, or obtained from commercial or non-commercial sources. The genomic or cDNA library may then be screened by nucleic acid hybridization to a labelled *E. coli* cadC probe (Grunstein & Hogness, 1975, Proc. Natl. Acad. Sci. U.S.A. 72:3961) and positive clones can be isolated and sequenced.

In a specific example, a CadC homolog can routinely be identified in *Salmonella typhimurium*. The cadC gene is well characterized in *E. coli*, its sequence (GenBank entry ECOCADAB(93.984) and SWISS-PROT EG10133/ P23890) and locus on the *E. coli* genome (93.8 centisomes) are known (Bachmann, 1990, Microbiol. Rev. 54:130–197; Rudd, 1992, in Miller, 1992, supra, pp. 2.3–2.43). This region is tightly conserved between the *E. coli* and *S. typhimurium* chromosomes; genetic loci on either side of the cadC region are conserved—melA (encoding melibiose) is located at 93.4 centisomes of *E. coli* and at 93 of *S. typhimurium* and mutL (MutatorL) and purA (purine metabolism) are located at position 95 of *E. coli* and 96 of *S. typhimurium*.

Clones containing genomic DNA from this region (for example, clones containing the neighboring mutL gene) can be obtained from, e.g., cosmid and/or phage libraries of *S. typhimurium*. Alternatively, a complete *S. typhimurium* genomic cosmid or λ library may be used. The *S. typhimurium* library may then be screened by hybridization with an *E. coli* CadC probe utilizing hybridization conditions such as those described above. For example, since the two genes are expected to be highly homologous, standard moderately stringent hybridization conditions are preferred.

In one embodiment, such conditions can include the following: Filters containing DNA can be pretreated for 6 h at 55° C. in a solution containing 6×SSC, 5×Denhart's solution, 0.5% SDS and 100 μg/ml denatured salmon sperm DNA. Hybridizations can be carried out in the same solution and 5–20×10⁶ cpm ³²P-labeled probe is used. Filters can be incubated in hybridization mixture for 18–20 hours at 55° C., and then washed twice for 30 minutes at 60° C. in a solution containing 1×SSC and 0.1% SDS. Filters are then blotted dry and exposed to X-ray film for autoradiography. Other conditions of moderate stringency which may be used are well-known in the art. Washing of filters is done at 37° C. for 1 hour in a solution containing 2×SSC, 0.1% SDS. Subsequent isolation, purification and characterization of clones containing the *S. typhimurium* can be performed by procedures well known in the art (see Ausubel et al., supra). Such sequences can be used to construct the *S. typhimurium* CadC-fusion polypeptides of the invention.

Alternatively, the *S. typhimurium* gene can be isolated from *S. typhimurium* mRNA. mRNA can be isolated from cells which express the CadC protein, such as cells that have been exposed to lysine or high pH, for example. A cDNA library may be produced by reverse transcription of mRNA, and screened by methods known in the art, such as those described above for screening a genomic library (see Ausubel et al., supra). Alternatively, CadC cDNA can be identified by PCR techniques, such as RACE (Rapid Amplification of cDNA Ends; Ausubel et al., supra), using two primers designed from the *E. coli* cadC sequence: a "forward" primer having the same sequence as the 5' end of the *E. coli* CadC mRNA, and a "reverse" primer complementary to its 3' end. The PCR product can be verified by sequencing, subcloned, and used to construct the CadC-fusion polypeptides of the invention. Such cDNA sequences can also be used to isolate *S. typhimurium* genomic cadC sequences, using methods well known in the art (Sambrook et al., 1989, supra; Ausubel et al., supra).

Nucleic acid molecules encoding the CadC-fusion polypeptides of the invention can, further, be synthesized and/or constructed according to recombinant and synthetic means well known to those of skill in the art (See e.g., Sambrook, supra and Ausubel et al., supra.). Methods and techniques for manipulations of *Salmonella typhimurium* are also well known in the art. Basic bacterial and molecular biology techniques can be utilized to clone and transfer genes in *S. typhimurium* (see Sambrook et al., 1989, supra; Ausubel et al., supra; Silhavy et al., supra; Miller et al., 1992, supra). The genome is well characterized, P1 transduction is possible, and many HFR strains are available (Sanderson & MacLauchlan in "*Escherichia coli* and *Salmonella typhimurium*", 1987, supra, p.1143; Miller et al., supra; see also Casadesis et al., 1994, Microbiologia, 4:357–70).

As discussed below, the ability to control the expression of the sequences such that expression can be regulatable (e.g. inducible) and such that a wide range of expression levels can be achieved is beneficial to the performance of the methods of the invention.

The nucleic acid molecules can, for example, be expressed extrachromosomally, e.g., on a plasmid, cosmid or a bacteriophage. Alternatively, the nucleic acid molecules can be integrated into the chromosome, e.g., *E. coli* chromosome, utilizing, for example, phage transduction or transposition.

Thus, the CadC-fusion polypeptide coding sequences can be engineered by standard techniques to be present in high copy, low copy, or single copy within each cell. A variety of different regulatory sequences can be also utilized for driving expression of the CadC-fusion polypeptides. Each of these aspects of expression/strain construction can be manipulated to yield cells exhibiting a wide range of CadC-fusion polypeptide expression levels. It is to be noted that single copy chromosomal version of the CadC-fusion polypeptide coding sequences are additionally advantageous in that such a configuration facilitates construction of strains.

For example, when a high level of expression is desired, nucleic acid molecules can be designed to reside on a high-copy plasmid such as a plasmid containing a ColE1-derived origin of replication, examples of which are well known in the art (see Sambrook et al., 1989, supra; see also Miller, 1992, A Short Course in Bacterial Genetics, Cold Spring Harbor Laboratory Press, NY, and references therein), such as pUC19 and its derivatives (Yanisch-Perron et al., 1985, Gene 33:103–119). pUC vectors exist at levels of 500–15 700 copies per cell and have convenient cloning sites for insertion of foreign genes. For very high expression, λ vectors, such as λgt11 (Huynh et al., 1984, in "DNA Cloning Techniques:, Vol I: A Practical Approach", D. Glover, ed., pp 49–78, IRL Press, Oxford), or the T7 or SP6 phage promoters in cells containing T7 and Sp6 polymerase expression systems (Studier et al., 1990, Methods Enzymol., 185:60–89).

When a lower level of expression is desired nucleic acid molecules can be designed to reside on a medium or a low-copy plasmid. Medium-copy plasmids are well known in the art, such as pBR322, which has a ColE1 derived origin of replication and 15–20 copies per cell (Bolivar et al., 1977, Gene 2:95–113; see Sambrook et al., 1989, supra), or pACYC184, one of the pACYC100 series of plasmids, which have a p15A origin of replication and exist at 10–12 copies per cell (Chang & Cohen, 1978, J. Bacteriol. 134:1141–56; see also Miller, 1992, p10.4–10.11). Low-copy plasmids are also well known in the art, for example, pSCO101, which has a pSC101 origin, and approximately 5 copies per cell. Both pACYC and pSC101 plasmid vectors have convenient cloning sites and can co-exist in the same cell as pBR and pUC plasmids, since they have compatible origins of replication and unique selective antibiotic markers.

When even less expression is desired, the nucleic acids can be inserted into the bacterial chromosome at a single copy level using gene transfer techniques well known in the art (see Miller, 1992, supra). Such insertions can be constructed using gene transfer techniques including transformation, conjugation, or transduction. Useful techniques to insert genes into bacterial chromosomes include, but are not limited to, P1 transduction, Mu transposition, λ lysogeny and conjugation (see Miller, 1992, supra; Neidhardt, F. C., ed., 1987, *Esherichla coli* and *Salmonella typhimurium*, American Society for Microbiology, Washington, D.C.; Yarmolinsky, M. B. & Sternberg, N., 1988, pp. 291–438, in Vol. 1 of *The Bacteriophages*, R. Calendar, ed., Plenum Press, New York).

With respect to regulatory controls which allow expression (either regulated or constitutive) at a range of different expression levels, a variety of such regulatory sequences are well known to those of skill in the art. The ability to generate a wide range of expression is advantageous for utilizing the methods of the invention, as described below. Such expression can be achieved in a constitutive as well as in a regulated, or inducible, fashion.

Inducible expression yielding a wide range of expression can be obtained by utilizing a variety of inducible regulatory sequences. In one embodiment, for example, the lacI gene and its gratuitous inducer IPTG can be utilized to yield inducible, high levels of expression of CadC-fusion polypeptides when sequences encoding such polypeptides are transcribed via the lacOP regulatory sequences.

A variety of other inducible promoter systems are well known to those of skill in the art which can also be utilized. Other regulated expression systems that can be utilized include but are not limited to, the TET system (Geissendorfer M. & Hillen W., 1990, Appl. Microbiol. Biotechnol. 33:657–663), the $P_L$ promoter of phage λ temperature and the inducible lambda repressor $CI_{857}$ (Petrenko et al., 1989, Gene 78:85–91) and the trp repressor (Wame et al., 1986, Gene 46:103–112), lpp (Nokamura et al., et al., 1982, J. Mol. Appl. Gen. 1:289–299) and the arac promoter which is inducible by arabinose (AraC; see, e.g. FIG. 9). Other inducible bacterial promoters that can be used, include but are not limited to, the T7 gene-10 promoter, phoA (alkaline phosphatase), recA (Horii et al. 1980), and the tac promoter, a trp-lac fusion promoter, which is inducible by tryptophan (Amann et al., 1983, Gene 25:167–78).

Levels of expression from CadC constructs can also be varied by using promoters of different strengths. $\lambda P_L$ (Pirrotta, 1975, Nature 254: 114–117) the trp promoter (Bennett et al., 1976, Proc. Natl. Acad. Sci USA 73:2351–55), and the lacUV5 promoter (Gilbert & Maxam, 1973, Proc. Natl. Acad. Sci. USA 70:1559–63), for example, are all commonly used strong promoters, resulting in an accumulated level of about 1 to 10% of total cellular protein for a protein whose level is controlled by each promoter. If a stronger promoter is desired, the tac promoter is approximately tenfold stronger than lacUV5, but will result in high baseline levels of expression, and should be used only when overexpression is required. If a weaker promoter is required, other bacterial promoters are well known in the art, for example, maltose, galactose, or other desirable promoter (sequences of such promoters are available from Genebank (Burks et al. 1991, Nucl. Acids Res. 19:2227–2230).

The present invention further relates to nucleic acid molecules encoding the CadC-fusion polypeptides of the invention. In one embodiment, such nucleic acid molecules are present as part of a plurality of nucleic acid molecules encoding CadC-fusion polypeptides representing a CadC-fusion polypeptide library.

5.2.1. CadC-Fusion Polypeptide Transcriptional Regulatory Domains

A CadC-fusion polypeptide transcriptional regulatory domain (TRD) comprises a CadC amino acid sequence which, when part of an activated (e.g., dimerized) CadC-fusion polypeptide, can interact with and bind to a cadBA regulatory region and drive RNA polymerase-dependent transcription, e.g., stimulate RNA polymerase to initiate RNA transcription of the cadBA operon.

In one embodiment, a CadC TRD comprises the amino acid sequence of an entire CadC N-terminal cytoplasmic domain. An exemplary *E. coli* N-terminal cytoplasmic domain is depicted and schematically diagrammed in FIG. 2.

In another embodiment the CadC TRD comprises a portion of a CadC N-terminal domain, wherein said portion can bind to the cadBA regulatory region and activate RNA transcription. For example, such a portion of a CadC cytoplasmic domain can comprise a portion of a CadC cytoplasmic domain, such as, for example, the CadC cytoplasmic domain depicted in FIG. 2, that can bind to cadBA and activate transcription therefrom. A candidate CadC TRD can, for example, be tested for its ability to activate transcription by linking the potential TRD to a functional CadC carboxy-portion comprising CadC transmembrane and periplasmic domains and assaying for the ability of the test protein to activate cadBA-reporter gene expression.

5.2.2. CadC-Fusion Polypeptide Transmembrane Domains

A CadC-fusion polypeptide transmembrane domain (TMD), in general, comprises any hydrophobic peptide domain which can act to anchor a CadC-fusion polypeptide to a procaryotic, e.g., *E. coli*, inner plasma membrane in a manner such that the CadC-fusion polypeptide periplasmic domain becomes inserted into the procaryotic periplasmic region and the TRD is inserted into the cytoplasm. The amino portion of the transmembrane domain is operatively attached to the carboxy portion of the TRD, while the carboxy portion of the transmembrane domain is operatively attached (i.e., linked) to the amino portion of the periplasmic domain.

In one embodiment, a TMD comprises an *E. coli* CadC transmembrane domain such as that depicted in FIG. 2. In a preferred embodiment, the CadC-fusion polypeptide TRD comprises a CadC cytoplasmic domain and the TMD comprises a CadC transmembrane domain.

In another embodiment, the TMD can comprise a Type II receptor protein transmembrane domain, or any peptide domain that anchors the CadC-fusion polypeptide to the bacterial inner plasma membrane. Such a TMD embodiment may, for example, be derived from any Type II receptor protein sequence.

In yet another embodiment, a TMD can comprise a synthetic peptide sequence or natural peptide domain containing a hydrophobic stretch of amino acids sufficient to anchor the CadC-fusion polypeptide to a bacterial inner plasma membrane in an orientation as described above.

Routine assays can be utilized to determine whether a candidate TMD becomes localized to the inner membrane in the above-described desired fashion. In one such assay, for example, a nucleic acid construct is generated which encodes a fusion polypeptide comprising an amino-terminal portion comprising a TRD and the candidate TMD, and a carboxy portion comprising an alkaline phosphatase reporter gene, and which expresses the sequence in a bacterial host cell, e.g., *E. coli*, exhibiting a periplasmic space and inner membrane. In instances in which the candidate TMD functions to localize to the inner membrane, transformation of the bacterial cell with the construct leads to the expression of the alkaline phosphatase fusion protein and the insertion of alkaline phosphatase domain into the periplasmic space of the bacterial cell. Alkaline phosphatase activity in the periplasmic space can then be detected by routine assays well known in the art (see, for e.g., McGovern et al. 1991, EMBO J. 10:2773–2782).

A candidate TMD can also be tested for its ability to function as part of a CadC-fusion polypeptide by, for example, linking, from amino to carboxy terminus, a TRD, candidate TMD and a functional periplasmic domain, and assaying for the ability of the CadC-fusion polypeptide to exhibit protein-protein interactions sufficient to activate transcription from a cadBA regulatory sequence, e.g., transcription of a reporter gene sequence. It is to be noted that in certain embodiments, CadC-fusion polypeptide protein-protein interaction-dependent (e.g., dimerization-dependent) transcriptional activation, per se, does not require actual insertion into the bacterial inner plasma membrane. In such instances, this assay can identify a functional TMD independent of the domain's anchoring potential.

5.2.3 CadC-Fusion Polypeptide Periplasmic Domains

A CadC-fusion polypeptide periplasmic domain can comprise a protein-protein interaction domain or a test domain.

A protein-protein interaction domain comprises an amino acid sequence which, under standard conditions utilized for cell (e.g., *E. coli*) culture, interacts with, that is, binds to, a peptide or polypeptide "partner." Such interaction between two (or more) polypeptide domains is defined by the resultant activation of the CadC TRD and its activation of expression of cadBA-linked sequences (see, e.g., Section 5.2.1, above).

Such an interaction can be a homotypic or a heterotypic interaction. A homotypic interaction refers to an interaction in which the polypeptide partner is the same as the interacting portion of the protein-protein interaction domain. A heterotypic interaction refers to an interaction in which the polypeptide partner differs from the interacting portion of the protein-protein interaction domain.

The protein-protein interaction domains of the invention can form dimers, trimers, tetramers, pentamers, hexamers or other oligomers or multimers (i.e., other higher-order aggregates) with one or more polypeptide partners. As discussed above, such interactions can be homotypic or heterotypic. Therefore, the protein-protein interaction domains can form homodimers, homotrimers, homotetramers, homopentamers, homohexamers, homooligomers or homomultimers, as well as heterodimers, heterotrimers, heterotetramers, heteropentamers, heterohexamers, heterooligomers or heteromultimers. In instances in which the protein-protein interaction domain forms a dimer, the protein-protein interaction domain can be referred to as a "dimerization domain." Using the same convention, appropriate protein-interaction domains can, likewise, be referred to as trimerization domains, tetamerization domains, and so forth. For ease of discussion, and not by way of limitation, the term "dimerization domain" will, in general, be utilized herein.

In one embodiment, the protein-protein interaction domain comprises an amino acid sequence derived from the extracellular domain of a cell surface (transmembrane or membrane-associated) receptor. For example, the protein-protein interaction domain can comprise the full-length extracellular domain of such a receptor. In instances in which interaction between the protein-protein interaction domain and its partner or partners is to be ligand-dependent, the ligand-binding portion of the extracellular domain should also be included as part of the protein-protein interaction domain.

Preferred protein-protein interaction domains comprising amino acid sequences derived from extracellular domains of cell surface receptors include, but are not limited to, protein-protein interaction domains comprising amino acid sequences which contribute to dimerization of erythropoietin receptor (Epo-R; Noguchi et al., 1991, Blood 78(10): 2548–2556), the insulin receptor (InsR; Ebina et al., 1985, Cell 40:747–758; and Ullrich, 1985, Nature 313:756–761), and the tumor necrosis factor alpha receptor (TNFαR; Gray et al., 1990, Proc. Natl. Acad. Sci. USA 87:7380–7384). CadC-fusion polypeptides comprising these protein-protein interaction domains are described in detail in the Examples presented in Sections 10, 11, and 12, respectively.

Other protein-protein interaction domains can include, but are not limited to, protein-protein interaction domains comprising amino acid sequences which contribute to dimerization of other members of the single transmembrane tyrosine receptor kinase (TRK)-like class of receptors (Ullrich & Schlessinger, 1990, Cell 61:203–12; Hunter & Cooper, 1985, Ann. Rev. Biochem. 54:897–930). This class includes: epidermal growth factor receptor family, including epidermal growth factor (EGF; Ullrich et al., Nature, 1984, 309:418–25; Schector et al., Nature 278:835–38), vaccinia growth factor (Brown et al., 1985, Nature 313:491–92), amphiregulin/schwannoma-derived growth factor (AR or SDGF; Schoyab, et al., 1989, Science 243:1074–1076), heparin-binding EGF-like factor (HB-EGF; Higashiyama et al., 1991, Science 251:936–939), the neu differentiation factor (NDF; Wen et al. 1992, Cell, 69:559–72), and the heregulins (Holmes et al., 1992, Science 256:1205–10) such as Her2 (Coussens et al., 1985, Science 230:1132–39; and Santanta et al. 1994, Proc. Natl. Acad. Sci. USA 91:1711–1715); the insulin receptor family, including INSR, as above, and IRR; the platelet-derived growth factor (PDGF) receptor family, including α-PDGFR (Potts & Carrington, 1993, Dev. Dyn. 198: 14–21), β-PDGFR (Chi et al., 1997, Oncogene 15:1051–58), CSF1-R (e.g., Waterfield et al., 1983, Nature 304: 35–39), c-Kit stem cell factor receptor (Lemmon et al. 1997, J. Biol. Chem. 272:6311–6317); the fibroblast growth factor receptor (FGFR), including CEK2 (Pasquale, 1990, Proc. Natl. Acad. Sci. U.S.A. 87:5812–16); the TRK receptor family, including TRK and TRK-B; and the EPH/ECK receptor family including Elf-1 and Eck (Cheng & Flanagan, 1994, Cell 79:157–68; Lindberg & Hunter, 1990, Mol. Cell Biol. 10:6316–24); nerve growth factor receptor (Woo et al. 1998, Protein Sci. 7:1006–1016; Johnson et al., 1986, Cell 47:545–54); and insulin-like growth factor receptor (Ullrich et al., 1986, EMBO J. 5:2503–12; and Sepp-Lorenzino, 1998, Breast Cancer Res. Treat. 47:235–253). Other members of the TK-like family of receptors can also be utilized. See, e.g., van der Greer et al., 1997, Ann. Rev. Cell Biol. 10:251–337; and Herz et al. 1997, J. Recept. Signal Transduct. Res. 17:671–776, each of which is incorporated herein by reference in its entirety, and references therein.

In another embodiment, the protein-protein interaction domain can comprise amino acid residues derived from polypeptides of members of the 7-transmembrane class of receptors (e.g., the G-protein coupled class of receptor (GPCR), including the β3 adrenergic receptor (Emorine et al., 1989, Science 245: 1118–21; see Huang et al., 1997, J. Recept. Signal Transduct. Res. 17:599–607), dopamine receptor, e.g., dopamine D2 receptor (Wilkie et al., 1993, Genomics 18:175–184; Bunzow et al., 1988, Nature 336: 783–7) and the muscarinic acetylcholine receptor (see Strader et al., 1994, Ann. Rev. Biochem. 63:101–32, which are incorporated herein by reference in their entirety, and references cited therein). CadC-fusion polypeptides having a protein-protein interaction domain comprising amino acid residues derived from the mature GPCR may form an eight transmembrane protein. Furthermore, any CadC-fusion polypeptide which renders signaling responsive to known β-adrenergic agonists or antagonists will be of interest regardless of the structure of the chimera or location of the fusion junction.

In another embodiment, CadC-fusion polypeptides can comprise protein-protein interaction domains derived from ion channels. Association between subunits of an ion channel provides a mechanism for the modulation of channel function (Ludewig et al., 1998, Nature 383:340–343; Fahike et al., 1997, J. Gen. Physiol. 109(1):93–104; Unwin, 1989, Neuron 3:665–76). The amino acid sequences of such protein-protein interaction domains are well known to those of skill in the art, and can include, but are not limited to, the Kv1.3 potassium channel (Kath et al., 1997, in Annual Reports in Med. Chem., Hagmann, ed., 32:181–89) and the NHEI and NHE2 $Na^+/H^+$ exchangers (Fafournoux & Pouysseyur, 1994, J. Biol. Chem. 269:2589–96). Also provided are the voltage-gated ion channel family of receptors, such as the $K^+$ sensitive channels and the $Ca^{2+}$ sensitive channels (see, Hille, B. in "Ionic Channels of Excitable Membranes," 1992, Sinauer Associates, Sunderland, Mass.; Catterall, W. A., 1991, Science 253:1499–1500, which are incorporated herein by reference in their entirety, and references cited therein).

In another embodiment, the protein-protein interaction domain can comprise amino acid residues derived from polypeptides of members of the receptor protein-tyrosine phosphatase family, or R-PTPs. This class of receptors includes, for example, CD45 (or leukocyte-common antigen, LCA), R-PTPs α, β, γ, κ and others (see, e.g., Denu et al., 1996, Cell 87:361–64; Fashena and Zinn, 1995, Curr. Biol. 5:1367–69, each of which is incorporated herein by reference in its entirety. Members of the PTP family are particularly interesting candidates for the CadC-based systems of the invention because dimerization may inhibit their activity, in contrast to the activating role that dimerization plays for many other receptors (see, e.g., Weiss & Schlessinger, 1998, Cell 94:277–80). Furthermore, physiologic ligands for most members of this family of receptors are not known, making RPTPs particularly well suited foruse as part of the methods for identification of ligands, as described, below, in Section 5.4 and 5.5.

In another embodiment, the protein-protein interaction domain can comprise amino acid residues derived from polypeptides of members of the cytokine receptor family: the IL-1 cytokine receptor family (IL-1α and IL-1β; see, e.g., Vigers et al. 1997, Nature 386:190–194); the class I cytokine family, particularly the growth hormone receptor subfamily of hematopoietic cytokine receptors, characterized by highly conserved cysteines involved in homodimerization (Watowich et al. Proc. Nat. Acad. Sci., 89:2140–44). This family includes not only EPO receptor (Noguchi et al., 1991, supra), but also growth hormone receptor (Cunningham, et al., 1989, Science 243:1330), the prolactin receptor (Boutin et al., 1988, Cell 53:69), CSF, the granulocyte-colony stimulating factor receptor (Seto et al., 1992, J. Immunol. 148(1):259–266), somatotropin receptor (Leung et al., 1987, Nature 330:537), glial-derived neurotrophic factor (GDNF) receptors, such as GFRα3 (Baloh et al. Proc. Natl. Acad. Sci. 95:5801–06), and many others (see Herz et al. 1997, supra); and the class II cytokine receptor (interferon) family members, in which ligand-binding may induce dimerization and activation through JAK kinases (Aguet et al., 1988, Cell 55:273–80; and Uze et al., 1990, Cell 60:225–234).

In another embodiment, the protein-protein interaction domain can comprise amino acid residues derived from polypeptides of members of the nuclear hormone receptor superfamily (see, e.g., Mangelsdorf et al., 1995, Cell 83:835–39, which is incorporated herein in its entirety, and references cited therein) including the steroid receptors (see Beato et al., 1995, Cell 83:851–57, which is incorporated here in its entirety, and references cited therein): glucocorticoid (Hollenberg et al., 1985, Nature, 318:635–41; see also Evans, 1989, Recent Prog. Horm. Res. 45:1–22, and references within, which are incorporated in their entirety), androgen (Tilley et al. Proc. Nat. Acad. Sci. U.S.A., 1989, 86:327–31), aldosterone, progesterone, and estrogen receptors (Greene et al, 1986, Nature 320:134–39; see also Tsai & O'Malley, 1994, Ann. Rev. Biochem. 63:451–86, which are incorporated herein their entirety, and references cited therein); and the heterodimeric receptors, including thyroxin, vitamin D, vitamin A, retinoid (RAR, RXR), prostinoid receptors (see Mangelsdorf & Evans, 1995, Cell 83:841–50 which is incorporated herein by reference in its entirety, and references cited therein) such as the hepatic nuclear factor HNF4 (Sladek et al., 1990, Genes Dev. 4:2353–65). Orphan receptors within these classes represent particularly interesting sequences which can be utilized as part of the methods of the invention for identifying ligands in that they represent a family of heterodimeric and homodimeric receptors whose putative ligands are not known.

In another embodiment of the invention, the CadC-fusion domain can comprise a protein-protein interaction domain of an intracellular, extracellular or viral protein. For example, protein-protein interaction domains are important for many steps within signal transduction pathways from the cell surface receptor to transcriptional activation in the nucleus, and the CadC system of the invention can be used to detect such interactions, as well as to identify compounds which mediate such interactions.

Many cellular proteins, for example, are known to have domains and motifs, such as SH2, SH3, PH, PTB, WW, and WD40 domains, leucine-rich repeats, and F-box motifs, that are involved in cellular protein-protein interactions (see Sudol et al., 1996, Trends Biochem. 21:1–3, and Koch et al, 1991, Science 252:668–74, which are incorporated herein by reference in their entirety). Amino acid residues comprising such domains can comprise protein-protein interaction domains of the CadC-fusion polypeptides of the invention.

In one such embodiment, the CadC fusion polypeptide protein-protein interaction domain can comprise amino acids involved in protein interactions required for heterotrimeric G-protein interaction (Neer, 1995, Cell 80:249–257; Clapham & Neer, 1993, Nature 365:403–406). In another embodiment, the protein-protein interaction domain of the CadC-fusion polypeptides can comprise protein-protein interaction domains from the non-receptor protein kinases, such as the src family or the Janus family of protein tyrosine kinases (see, e.g., Darnell et al., 1994, Science, 264:1415–21,; Cantley et al., 1991, Cell 64:281–302, which are incorporated herein by reference in their entirety, and references cited therein), Further, in another embodiment, the CadC-fusion polypeptide protein-protein interacion domain can comprise a protein-protein interaction domain of a nuclear transcription factor protein. Many transcription factors are activated by homotypic and heterotypic dimerization (see, e.g., Lamb & McKnight, 1991, Trends Biochem. Sci. 16:417–22, which is incorporated herein by reference in its entirety, and references cited therein). Thus, protein-protein interaction domains can include, for example, sequences derived from transcription factors, such as transcription factors containing leucine zipper dimerization domains, including, but not limited to Fos/Jun (Bohmann et al., Science 238:1386–92; and Angel et al., 1988, Nature 332:166–71), C/EBP (Landshultz et al., 1988, Science, 240:1759–64), GCN4 (see, e.g., Agre et al., 1989, Science 246:922–926; see, also, the Example presented, below, Section 9); helix loop helix (HLH) domain proteins, for example Myc (Murre et al, 1989, Cell 56:777–783) and MyoD and other myogenic HLH proteins which require heterooligimerization with E12/E47-like proteins in vivo (Lasser et al., 1991, Cell 66:305–15), as well as other dimerizing transcription factors well known in the art.

The CadC based system can be used to detect dimerization and protein-protein interactions in proteins having extracellular functions. For example, cell adhesion proteins such as integrins, may require association with partner disintegrin proteins (Blobel, 1997, Cell 90:589–92). In this specific embodiment, CadC fusion polypeptides can comprise a protein-protein interaction domain from such an integrin protein to identify a putative disintegrin partner. Finally, in the present embodiment, the CadC fusion polypeptide can also comprise a protein-protein interaction domain of a viral protein such as, for example, amino acids that contribute to the dimerization of HIV protease (McKeever et al., 1989, J. Biol. Chem. 264:1919–1921).

As discussed above, a protein-protein interaction domain can also comprise any peptide domain that forms complexes larger than dimer size, e.g., trimers, tetramers, pentamers, etc. in a multimeric complex. Examples of such multimer-forming protein-protein interaction domains are well known to those skilled in the art and include, but are not limited to, polypeptides which form trimers, such as the receptors of the TNF family (Smith et al., 1990, Science 248:1019–23), including CD30 (Durkop et al., 1992, Cell, 68:421–27), CD40, NGF receptor (Johnson et al., 1986, Cell 47:545–54), and others. Also provided are polypeptides that form tetramers, including the voltage-gated $K^+$ ion channel family of receptors, which consist of oligomeric tetramers that may contain homologous or heterologous subunits (Ruppersberg et al., 1990, Nature 345:535–37; Li et al., 1992, Science 257:1225–30). In addition, pentameric receptors are also well known, including members of the ligand-gated ion channel family of receptors (LGPRs) which exist as pentameric homooligomers or heterooligomers. Examples include, but are not limited to, the nicotinic acetylcholine receptor (see, e.g., Nef et al., 1988, EMBO J., 7:595–601), the serotonin 5-HT$_3$ (Yakel, in "Central and Peripheral 5-HT$_3$ Receptors," 1992, Academic Press, pp. 103–28), GABA$_A$ (MacDonald & Olsen, 1994, Ann. Rev. Neurosci. 17:569–602), glycine (Betz, 1990, Biochem. 29:3591–99), purinergic P$_{2x}$ (Valera et al., 1994, Nature 371:516–18), and the ionotropic glutamate receptors (Wisden & Seeburg, L. Neurosci. 13:3582–98).

In addition to the proteins mentioned herein, a CadC fusion polypeptide can comprise amino acid residues derived from any dimeric or multimeric polypeptide listed in public databases, such as, for example, the Swiss Protein Data Base (SWISS-PROT; see Bairoch & Apweiler, 1998, Nucl. Acids Res. 26:38–42; see also http://www.expasy.ch/ and http://www.ncbi.nlm.nih.gov).

As also discussed above, a protein-protein interaction domain can comprise a peptide domain that can interact with, or form multimeric complexes with, a heterologous protein. Such multimeric proteins, such as heterodimers, heterotetramers, or other heteromultimers are well known to those skilled in the art. In such an embodiment of the invention, a first CadC-fusion polypeptide of interest can be co-expressed with a second (or subsequent) CadC-fusion polypeptide in the same cell. Methods for coexpression are well known to those of skill in the art.

Further, a protein-protein interaction can also comprise a peptide identified via the methods described herein (see, e.g., Section 5.4, below). it is noted that a protein-protein interaction domain should not comprise alkaline phosphase sequences.

In another embodiment of the invention, the periplasmic domain of the CadC-fusion polypeptide can comprise a test domain. A test domain comprises an amino acid sequence which is to be tested for an ability to act as a protein-protein interaction domain. That is, a test domain comprises an amino acid sequence which is to be tested for an ability to interact with a peptide or polypeptide partner, under standard conditions utilized for cell (e.g., *E. coli*) culture. Such amino acid sequences can be selected, e.g., from among any amino acid sequence listed in public databases such as those listed above. CadC-fusion polypeptides comprising test domains can be utilized, for example, as part of the methods described in Sections 5.4 and 5.5, below.

5.2.4. CadC-Fusion Polypeptide Junctions

In one embodiment, the amino acid sequence of all but the carboxy-terminal portion of the protein-protein interaction domain of the CadC-fusion polypeptide comprises CadC amino acid sequence. In such an embodiment, the position or junction at which the CadC amino acid sequence is linked to the non-CadC-derived portion of the protein-protein interaction domain can be as described herein.

In general, a CadC-fusion junction can be any junction within the CadC periplasmic domain, transmembrane domain or cytoplasmic domain that, when utilized as a CadC-fusion polypeptide junction, supports interaction between (e.g., dimerization of) CadC-fusion polypeptides that results in transcriptional activation of a cadBA regulatory region. Appropriate junctions can routinely be identified. For example, a CadC-fusion polypeptide having a non-CadC amino acid sequence containing a known dimerizing sequence linked to the CadC amino acid sequence portion of the CadC-fusion polypeptide at a candidate junction site can be tested for an ability to drive cadBA transcription via, for example, assaying cadBA-linked reporter gene expression. Such a method was successfully used with the leucine zipper protein-protein interaction domain of the yeast transcriptional activator GCN4 (Agre et al., 1989, Science 246, 922–926) to routinely identify two CadC junctions (termed herein "junction 1" and "junction 2"; see, e.g. FIG. 2), which can successfully be utilized in construction of CadC-fusion polypeptides, as described in the example presented in Section 9, below. In one embodiment, for example, the CadC-fusion junction is junction 1, as shown in FIG. 2. In another embodiment, for example, the CadC-fusion junction is junction 2, as shown in FIG. 2. It is generally not preferable to utilize junction 5, as shown in FIG. 2, as a CadC-fusion junction.

As discussed above, and in the Example presented below in Section 9, CadC-fusion polypeptides generated utilizing junctions 1 and 2 were able to successfully activate high-level dimerization-dependent expression of cadBA reporter constructs. As discussed in Section 9, junctions 1 and 2 were routinely generated via amplification using primers that generate CadC truncations. In addition to junctions 1 and 2, other junction points along the CadC sequence can routinely be generated and tested. In particular, for example, candidate CadC truncations at various junction points can easily be produced by utilizing a primer pair that will generate any CadC truncation of interest. For example, primer 1, as discussed in Section 9, below, can be utilized with any primer 2 to generate the CadC truncation of interest. Upon generation of a truncated CadC sequence, a CadC-fusion polypeptide can then routinely be produced and tested for an ability to drive CadC-fusion polypeptide interaction-dependent expression from cadBA regulatory sequences.

5.3. CadC-Based Cell Systems of the Invention

Described herein are CadC-based systems, said systems comprising a CadC-fusion polypeptide and/or nucleic acid molecule encoding the CadC-fusion polypeptide and a cadBA reporter construct. Such systems can, for example, comprise Enterobacteriaceae cells (e.g., *E. coli* or *S. typhimurium* cells) containing a CadC-fusion polypeptide and/or a nucleic acid molecule encoding a CadC-fusion polypeptide capable of being expressed in the cell and a cadBA reporter construct. In instances in which interaction between a CadC-fusion polypeptide of interest can be enhanced by the presence of an additional peptide component (e.g., a peptide ligand) the cells of the invention can further comprise a nucleic acid sequence encoding the ligand or a candidate ligand test peptide operatively linked to a regulatory sequence that drives expression of the ligand or candidate ligand in the cell. In one embodiment, CadC-based cell systems are present as a plurality of cells, wherein different individual cells express different CadC-fusion polypeptides and wherein such cells represent a CadC-fusion polypeptide library.

Preferably, the nucleic acid molecules can express variable levels of CadC-fusion polypeptides, including high-level expression sufficient to drive ligand-independent interaction (e.g., dimerization) of the CadC-fusion polypeptides. In instances in which interaction between a CadC-fusion polypeptide of interest can be enhanced by the presence of an additional peptide component (e.g., a peptide ligand) the cells of the invention can further comprise a nucleic acid sequence encoding the ligand or a candidate ligand test peptide operatively linked to a regulatory sequence that drives expression of the ligand or candidate ligand test peptide in the cell.

The CadC-based systems of the invention can represent completely native systems in which both the CadC amino acid sequences utilized as part of the CadC-fusion polypeptides and the cadBA regulatory sequences utilized as part of the cadBA reporter constructs are endogenous to the cell in which they are used.

In a preferred embodiment, one such CadC-fusion polypeptide system comprises an *E. coli* (e.g., *E. coli* K12)

cell comprising a CadC-fusion polypeptide comprising *E. coli* CadC amino acid sequences and/or nucleic acid encoding such a CadC-fusion polypeptide, and a cadBA reporter construct comprising *E. coli* cadBA regulatory sequences.

In another preferred embodiment, one such CadC-fusion polypeptide system comprises a *Salmonella typhimurium* cell comprising a CadC-fusion polypeptide comprising *S. typhimurium* CadC homolog amino acid sequences and/or nucleic acid encoding such a CadC-fusion polypeptide, and a cadBA reporter construct comprising *S. typhimurium* cadBA homolog regulatory sequences.

The CadC-fusion polypeptide systems of the invention can also, for example, represent completeley homologous ones in which CadC amino acid sequences utilized as part of the CadC-fusion polypeptides and the cadBA regulatory sequences utilized as part of the cadBA reporter constructs are derived from procaryotic cells of the family Enterobacteriaceae, as is the cell in which they can be found, but in which at least one component of the system (that is, CadC sequence, cadBA sequence or cell) is derived from a different cellular source than the rest.

In a preferred embodiment, such a CadC-fusion polypeptide system comprises an *E. coli* cell comprising a CadC-fusion polypeptide comprising *S. typhimurium* CadC amino acid sequences and/or nucleic acid encoding such a CadC-fusion polypeptide, and a cadBA reporter construct comprising either *E. coli* or *S. typhimurium* cadBA regulatory sequences.

In another preferred embodiment, such a CadC-fusion polypeptide system comprises a *S. typhimurium* cell comprising a CadC-fusion polypeptide comprising *E. coli* CadC amino acid sequences and/or nucleic acid encoding such a CadC-fusion polypeptide, and a cadBA reporter construct comprising either *E. coli* or *S. typhimurium* cadBA regulatory sequences.

The cells, e.g., the *E. coli* cells, of the invention should carry a loss of function allele of the endogenous cadC gene, thereby eliminating interference of functional endogenous cadC with the CadC-fusion polypeptides within the cell. Several such strains are well known in the art. See, e.g., Watson et al., 1992, J. Bacteriol. 174:530–540; Meng et al., 1992, J. Bacteriol 174: 2670–78; and Neely et al., 1994, J. Bacteriol. 176(22):3278–85, each of which is incorporated herein by reference in its entirety.

Among the cadC$^-$ strains which can be utilized is, for example, *E. coli* strain E2088 (F$^-$ araD139 Δ (ara-leu)7697 Δ (proAB-argF-lacIPOZYA)XIII rpsL Nal$^r$ exa-1::mudI1734 (kan) cadC1::Tn10; Watson et al., 1994, J. Bacteriol. 176(22):7017–7023). This strain contains a lac reporter sequence regulated by cadBA regulatory sequences and, therefore, contains a cadBA reporter construct. This construct is present within the *E. coli* chromosome at the position of the cadBA operon. In addition, construction of a cadC$^-$ *E. coli* strain is discussed, below, in the Example presented in Section 7.

5.4. METHODS FOR THE IDENTIFICATION OF PROTEIN-PROTEIN INTERACTIONS

The methods of the invention comprise, first, methods for the identification of protein-protein interactions, that is, methods for the identification of peptides which are involved in such interactions.

These methods can be utilized for the identification of peptides involved in protein-protein interactions which represent homotypic or a heterotypic interactions. A homotypic interaction refers to a self-interaction in which the polypeptide partner is the same as the interacting portion of the protein-protein interaction domain. A heterotypic interaction refers to an interaction comprising at least two different protein partners in which at least one of the polypeptide partner differs from another, e.g., differs from the interacting portion of the protein-protein interaction domain.

The peptides identified via such methods can undergo protein-protein interactions which result in the formation of dimers, trimers, tetramers, pentamers, hexamers or other oligomers or multimers (i.e., other higher-order aggregates) with one or more polypeptide partners. As discussed above, such interactions can be homotypic or heterotypic.

In one embodiment, such methods of the invention can be performed in instances wherein at least one of the peptide "partners" involved in a protein-protein interaction of interest is known at the outset. In another embodiment, such methods can be performed in instances in which, at the outset, none of the peptides involved in a protein-protein interaction are known. Each of these embodiments can be performed in instances wherein the protein-protein interactions of interest normally depend upon or are enhanced by the presence of an appropriate ligand, and can successfully be utilized either in the presence or absence of the ligand.

For methods in which at least one of the peptide "partners" involved in a heterotypic protein-protein interaction of interest is known at the outset, a CadC-based cell system can be utilized which comprises a nucleic acid encoding a first CadC-fusion polypeptide, said first CadC-fusion polypeptide comprising a protein-protein interaction domain containing a known peptide partner involved in the protein-protein interaction of interest, and a nucleic acid molecule encoding a second CadC-fusion polypeptide, wherein the periplasmic domain of the second CadC-fusion polypeptide is a test domain comprising a candidate peptide partner.

The cell is incubated under conditions whereby the first and the second CadC-fusion polypeptides are expressed (either constitutively or in a regulated, e.g., inducible, manner), and the level of reporter gene product expressed by the cell's cadBA reporter construct is assayed such that if the cell produces a higher level of cadBA reporter construct expression in the presence of the second CadC-fusion polypeptide than in its absence, the test domain is identified as a candidate peptide partner involved in the protein-protein interaction of interest.

It is noted that for ease of illustration and discussion, and not by way of limitation, the above method is described for an embodiment wherein the heterotypic protein-protein interaction is a heterodimeric one. Such a method can also be utilized for embodiments in which the heterotypic protein-protein interaction of interest is of a higher order (that is, involves a heterotrimeric, heterotetrameric, etc. interaction) by introducing a third, fourth, etc. CadC-fusion polypeptide as needed.

One of skill in the art would readily be aware of coexpression requirements necessary for expressing multiple CadC-fusion polypeptides. Methods for coexpression of two or more constructs in procaryotic cells are well known to those of skill in the art. For example, cells containing multiple separate expression constructs can routinely be selected for and maintained by utilizing vectors comprising appropriately compatible origins of replication and independent selection systems.

Utilizing a method as above, it is possible that the candidate peptide partner activates cadBA reporter construct expression via, e.g., self-dimerization or by some non-specific route unrelated to the protein-protein interaction of interest. To eliminate such a possibility, the second CadC-fusion polypeptide can be expressed in the cell (either constitutively or in a regulated, e.g., inducible, manner) in the absence of the first CadC-fusion polypeptide and cadBA reporter construct expression can be assayed. For such expression, the cell can, for example, comprise the same cell utilized in the first assay, except this cell has not been transformed with, that is, does not contain, nucleic acid sequences encoding the first CadC-fusion polypeptide. Alternatively, in instances in which expression of the CadC-fusion polypeptides is inducible, if the first CadC-fusion polypeptide is induced via a different mechanism than the second (e.g., ara vs. lac inducibility), expression of only the second CadC-fusion polypeptide can be accomplished via induction of only the nucleic acid sequence encoding the second CadC-fusion polypeptide. In instances in which cadBA reporter construct expression in such a cell is lower than that observed in cells expressing both the first and the second CadC-fusion polypeptide, the specificity of the test domain peptide for the heterotypic protein-protein interaction of interest is supported.

To further corroborate the specificity of the test domain for the protein-protein interaction of interest, the CadC-fusion polypeptide comprising the test domain can, for example, be expressed in the CadC-based cell system in the presence of a control CadC-fusion polypeptide, rather than in the presence of the first CadC-fusion polypeptide. For specificity to be corroborated, cadBA expression, as assayed by reporter gene expression, in such a cell should be lower than that exhibited in the presence of both the first and second interacting CadC-fusion polypeptides.

A "control CadC-fusion polypeptide," as used herein, refers to a CadC-fusion polypeptide comprising a periplasmic domain containing a protein-protein interaction domain that is not related to the sequences comprising the periplasmic domain of the first CadC-fusion polypeptide. That is, e.g., the periplasmic domain of the CadC-fusion polypeptide is not involved in the same protein-protein interaction as that of the first CadC-fusion polypeptide, and is, in general, neither structurally nor functionally related to that of the first CadC-fusion polypeptide. For example, a CadC-fusion polypeptide comprising a GCN4 leucine zipper protein-protein interaction domain can be utilized as a control CadC-fusion polypeptide in instances in which the protein-protein interaction of interest does not involve such a GCN4 leucine zipper protein-protein interaction domain, or a homolog thereof. The level of cadBA reporter gene expression elicited by the control CadC-fusion polypeptide, per se, should be lower than than level observed in the presence of the first and second CadC-fusion polypeptides.

It is noted that in instances in which the expression of either the first or the second CadC-fusion polypeptide alone results in cadBA reporter construct expression above background levels, while the test domains may not be involved in the heterotypic protein-protein interaction of interest, the test domains may represent protein-protein interaction domains involved in a homotypic protein-protein interaction, which can be verified utilizing the specificity assays discussed above for methods designed to identify homotypic protein-protein interactions.

For methods in which a peptide involved in a homotypic protein-protein interaction (e.g., homodimerization) is not known at the outset, a CadC-based cell system can be utilized to identify such a peptide. In this method, the CadC-based cell system comprises a nucleic acid encoding a CadC-fusion polypeptide, wherein the periplasmic domain of the CadC-fusion polypeptide is a test domain comprising a candidate peptide to be tested for an ability to undergo a homotypic protein-protein interaction.

The cell is incubated under conditions whereby the CadC-fusion polypeptide is expressed (either constitutively or in a regulated, e.g., inducible, manner), and the level of reporter gene product expressed by the cell's cadBA reporter construct is assayed such that if the cell produces a higher level of cadBA reporter construct expression in the presence of the test domain-containing CadC-fusion polypeptide than in its absence, the test domain is identified as a candidate peptide which undergoes a homotypic protein-protein interaction.

Utilizing such a method, it is possible that the candidate peptide activates cadBA reporter construct expression via some non-specific route unrelated to homotypic protein-protein interaction. To eliminate such a possibility, the CadC-fusion polypeptide can, for example, be coexpressed in the cell along with an expression construct that expresses the test domain of the CadC-fusion polypeptide alone (that is, independent of the remainder of the CadC-fusion polypeptide) via protein expresssion methods well known to those of skill in the art, and cadBA reporter construct expression can be assayed. A level of cadBA reporter construct expression in such a cell which is lower than that observed in cells expressing only the CadC-fusion polypeptide indicates that the independently expressed test domain is competing with the test domain within the CadC-fusion polypeptide and, therefore, supports the test domain's role in a homotypic protein-protein interaction.

For methods in which none of the peptide "partners" involved in a heterotypic protein-protein interaction of interest is known at the outset, a CadC-based cell system can be utilized which is designed to identify heterotypic interactions and which comprises a nucleic acid encoding a first CadC-fusion polypeptide, wherein the periplasmic domain of the first CadC-fusion polypeptide is a first test domain comprising a first candidate peptide partner, and a nucleic acid molecule encoding a second CadC-fusion polypeptide, wherein the periplasmic domain of the second CadC-fusion polypeptide is a test domain comprising a second candidate peptide partner.

The cell is incubated under conditions whereby the first and the second CadC-fusion polypeptides are expressed (either constitutively or in a regulated, e.g., inducible, manner), and the level of reporter gene product expressed by the cell's cadBA reporter construct is assayed such that if the cell produces a higher level of cadBA reporter construct expression in the presence of the first and second CadC-fusion polypeptides than in the absence of either the first or the second CadC-fusion polypeptides, the test domains are identified as candidate peptide partners involved in a heterotypic protein-protein interaction.

It is noted that for ease of illustration and discussion, and not by way of limitation, the above method is described for an embodiment wherein the heterotypic protein-protein interaction is a heterodimeric one. Such a method can also be utilized for embodiments in which the heterotypic protein-protein interaction of interest is of a higher order (that is, involves a heterotrimeric, heterotetrameric, etc. interaction) by introducing a third, fourth, etc. CadC-fusion polypeptide as needed.

One of skill in the art would readily be aware of coexpression requirements necessary for expressing multiple CadC-fusion polypeptides.Methods for coexpression of two or more constructs in procaryotic cells are well known to those of skill in the art. For example, cells containing multiple separate expression constructs can routinely be selected for and maintained by utilizing vectors comprising appropriately compatible origins of replication and independent selection systems.

Utilizing such a method, it is possible that the candidate peptide partners activate cadBA reporter construct expression via, e.g., self-dimerization or by some non-specific route unrelated to the heterotypic protein-protein interaction of interest. To eliminate such a possibility, the first and the second CadC-fusion polypeptides can be expressed (either constitutively or in a regulated, e.g., inducible, manner) in the cell in the absence of the other, and cadBA reporter construct expression can be assayed. For such expression, the cell can, for example, comprise the same cell utilized in the first assay, except this cell has not been transformed with, that is, does not contain, nucleic acid sequences encoding either the first or the second CadC-fusion polypeptide. Alternatively, in instances in which expression of the CadC-fusion polypeptides is inducible, if the first CadC-fusion polypeptide is induced via a different mechanism than the second (e.g., ara vs. lac inducibility), expression of only the first or the second CadC-fusion polypeptide can be accomplished via induction of only the nucleic acid sequence encoding the desired CadC-fusion polypeptide. In instances in which cadBA reporter construct expression in a cell expressing only the first or only the second CadC-fusion polypeptide is lower than that observed in cells expressing both the first and the second CadC-fusion polypeptide, the specificity of the test domain peptides for the heterotypic protein-protein interaction is supported.

To further corroborate that the test domains act with specificity, that is, interact in a specific manner as part of the same protein-protein interaction of interest, the first or the second CadC-fusion polypeptides can, for example, be expressed in the CadC-based cell system in the presence of a control CadC-fusion polypeptide, rather than in the presence of the other (i.e., either the first or the second) CadC-fusion polypeptide. For specificity to be corroborated, cadBA expression, as assayed by reporter gene expression, in such a cell should be lower than that exhibited in the presence of the first and second CadC-fusion polypeptides together. The control CadC-fusion polypeptide is as discussed above.

In certain instances, the protein-protein interaction of interest normally takes place in the presence of an additional, e.g., peptide, component, referred to herein as a "ligand." The protein-protein interaction of interest may be dependent upon or may be enhanced by the ligand. If such a ligand is known and available or expressible it is possible to perform the screen in the presence of the ligand. In such an embodiment, the two CadC-fusion polypeptide constructs and the ligand-expressing construct are coexpressed and cadBA reporter construct expression is measured.

The ligand can, for example, be introduced exogenously into the cell culture at a concentration necessary to facilitate protein-protein interaction. Such a procedure can generally only be followed in instances wherein the ligand is from about 800 to about 1000 daltons in size (Todt et al., 1992, Biochem. 31:10471–10478).

Alternatively, in instances in which the ligand is a peptide whose sequence is known, a nucleic acid sequence encoding the ligand can be co-expressed along with the nucleic acid encoding the CadC-fusion polypeptide, thereby creating an autologous system, sometimes referred to herein as an autologous ligand system, wherein the procaryotic cell expresses both the ligand and the peptide (e.g., receptor) sequence the ligand interacts with. It is contemplated that the compositions of the invention also include such autologous cell systems wherein the peptide which interacts with the coexpressed ligand is not necessarily present as part of a CadC-fusion polypeptide.

The ligand should be expressed in such a manner as to be targeted to the periplasmic region or space of the cell. Techniques for such targeting are well known to those of skill in the art. Leader sequences, associated with proteins naturally destined for the periplasm, are, for example, known to direct the secretion of foreign proteins to the periplasm (MacIntyre et al., 1990, Mol. Gen. Genet. 221:466–474) and test peptides can be engineered, utilizing standard techniques well known to those of skill in the art to be expressed containing these leader sequences. The preferred leader sequence for targeting the test peptides of the invention is the OmpA protein leader sequence (Hobom et al., 1995, Dev. Biol. Stand. 84:255–262). Other signal leader sequences are also possible, including, but not limited to, the leaders from *E. coli* Pho A (Oka et al., 1985, Proc. Natl. Acad. Sci 82:7212–16), OmpT (Johnson et al., 1996, Protein Expression 7:104–113), LamB and OmpF (Hoffman & Wright, 1985, Proc. Natl. Acad. Sci. USA 82:5107–5111), β-lactamase (Kadonaga et al., 1984, J. Biol. Chem. 259:2149–54), enterotoxins (Morioka-Fujimoto et al., 1991, J. Biol. Chem. 266:1728–32), protein A from Staphylococcus aureus (Abrahmsen et al., 1986, Nucleic Acids Res. 14:7487–7500), endoglucanase from *B. subtilis* (Lo et al., Appl. Environ. Microbiol. 54:2287–2292), as well as artificial and synthetic signal sequences (MacIntyre et al., 1990, Mol. Gen. Genet. 221:466–74; Kaiser et al., 1987, Science, 235:312–317). The nucleic acid molecule is, preferably, inducible in a manner independent of expression of the CadC-fusion polypeptide (e.g., expression of one construct is lac-inducible and the other is ara-inducible).

Methods for coexpression of two or more constructs in procaryotic cells are well known to those of skill in the art. For example, cells containing two separate expression constructs can routinely be selected for and maintained by utilizing vectors comprising appropriately compatible origins of replication and independent selection systems.

It is also contemplated that both the CadC-fusion polypeptide and the ligand coding regions can, for example, be expressed as part of a bicistronic message.

Whether or not a ligand is known, however, it is also possible to identify protein-protein interactions in the absence of ligand even if the protein-protein interaction of interest is normally ligand-dependent or ligand-enhanced. Many proteins that undergo ligand-dependent protein-protein interactions can exist in both monomeric and interactive (e.g., dimeric) states even in the absence of ligand. The equilibrium between the monomeric and interactive (e.g., dimeric) states is affected by the total concentration of the interactive protein. That is, the higher the level of expression of an interactive protein, the larger the percentage in an interactive state will be. Thus, overexpression of a CadC-fusion polypeptide comprising a protein-protein interaction domain will drive interaction of the domain even if such interaction is normally ligand-dependent. A diagramatic representation of this is given FIG. 3. Methods for such overexpression are well known to those of skill in the art, see, e.g., Section 5.2, above.

Successful ligand-independent interaction of normally ligand-dependent or ligand-enhanced protein-protein interaction domains via such high level, e.g., inducible, expression of CadC-fusion polypeptides is demonstrated in the Examples presented below in Sections 10, 11, and 12. These, Examples demonstrate ligand-independent protein-protein interactions for Epo-, insulin- and TNFα-receptors. Wherein, as is well known to those of skill in the art, such interactions are normally ligand-dependent. As also shown in these examples, cadBA reporter consruct activation is a function of the CadC-fusion polypeptide level of expression. That is, increasing levels of CadC-fusion polypeptide expression lead to cadBA reporter construct expression and further increases in CadC-fusion polypeptide levels lead to enhanced signaling.

The methods of the invention also comprise methods for the identification of ligands which normally enhance a protein-protein interaction of interest. For example, it is well known that many receptors, e.g., receptor protein tyrosine kinase receptors, undergo dimerization and activation upon binding of the receptors by their extracellular ligand partners. The natural ligands for many such receptors, however, are not currently known. Such methods can be utilized, for example, to successfully identify ligands which elicit interaction between (e.g., dimerization) and activation of such "orphan" receptors. It is to be noted that such a methods can also fornally be considered a methods for identifying a compound which modulates protein-protein interactions, as described below, in Section 5.5.

In one embodiment, such methods utilize a CadC-based cell system of the invention comprising a nucleic acid molecule encoding a CadC-fusion polypeptide, said CadC-fusion polypeptide comprising a protein-protein interaction domain that contains the peptide that undergoes the protein-protein interaction of interest. The CadC-fusion polypeptide coding sequence is expressed in a manner which results in a low, yet detectable level of cadBA report construct expression (that is, preferably less than about 50% of maximal expression and most preferably less than about 10% of maximal expression) as measured by reporter gene sequence expression/activity. For example, in instances wherein the expression of the CadC-fusion polypeptide is under inducible regulation, induction conditions can routinely be determined which will result in the desired level of cadBA reporter construct expression. Successful examples of routine determination of conditions under which desired induction levels can be attained are demonstrated in the Examples presented, below, in Sections 9.2, 10, 11, and 12.

The CadC-based cell system utilized in such methods further comprises a nucleic acid molecule which encodes a test peptide to be tested for an ability to act as the ligand of interest. Such a CadC-based cell system can also be referred to as an autologous system or an autologous ligand system in thatthe cell comprises potential modulators of the protein-protein interaction of interest along with the CadC-fusion polypeptide. The test peptide should be such that its location is targeted to the periplasmic region or space of the cell. Techniques for such targeting are well known to those of skill in the art. Leader sequences, associated with proteins naturally destined for the periplasm, are, for example, known to direct the secretion of foreign proteins to the periplasm (MacIntyre et al., 1990, Mol. Gen. Genet. 221:466–474) and test peptides can be engineered, utilizing standard techniques well known to those of skill in the art to be expressed containing these leader sequences. The preferred leader sequence for targeting the test peptides of the invention is the OmpA protein leader sequence (Hobom et al., 1995, Dev. Biol. Stand. 84:255–262). Other signal leader sequences are also possible, including, but not limited to, the leaders from *E. coli* Pho A (Oka et al., 1985, Proc. Natl. Acad. Sci 82:7212–16), OmpT (Johnson et al., 1996, Protein Expression 7:104–113), LamB and OmpF (Hoffman & Wright, 1985, Proc. Natl. Acad. Sci. USA 82:5107–5111), β-lactamase (Kadonaga et al., 1984, J. Biol. Chem. 259:2149–54), enterotoxins (Morioka-Fujimoto et al., 1991, J. Biol. Chem. 266:1728–32), protein A from Staphylococcus aureus (Abrahmsen et al., 1986, Nucleic Acids Res. 14:7487–7500), endoglucanase from *B. subtilis* (Lo et al., Appl. Environ. Microbiol. 54:2287–2292), as well as artificial and synthetic signal sequences (MacIntyre et al., 1990, Mol. Gen. Genet. 221:466–74; Kaiser et al., 1987, Science, 235:312–317). The nucleic acid molecule is, preferably, inducible in a manner independent of expression of the CadC-fusion polypeptide (e.g., expression of one construct is lac-inducible and the other is ara-inducible).

One of skill in the art would readily be aware of coexpression requirements necessary for expressing multiple CadC-fusion polypeptides. Methods for coexpression of greater than two constructs in procaryotic cells are well known to those of skill in the art. For example, cells containing multiple separate expression constructs can routinely be selected for and maintained by utilizing vectors comprising appropriately compatible origins of replication and independent selection systems.

Such methods comprise incubating the cell under conditions whereby the CadC-fusion polypeptide is expressed at a low level, as discussed above, the test peptide is coexpressed, and cadBA reporter construct expression is measured. If, for a given low level of CadC-fusion polypeptide expresion, a higher level of cadBA reporter construct gene expression is observed in the presence of test peptide than in its absence, a candidate ligand is identified.

In order to substantiate the specificity of the candidate ligand's effect on cadBA reporter gene expression, the nucleic acid encoding the test peptide can be expressed in the presence of a second, control CadC-fusion polypeptide, rather than in the presence of the CadC-fusion polypeptide comprising the known protein-protein interaction domain of interest, and cadBA reporter expression can be assayed. Here, in instances wherein the level of reporter expression is not altered in a statistically significant manner in the presence or absence of test peptide, the specificity of the test peptide is supported. The control CadC-fusion polypeptide is as described below.

It is noted that while the above-described embodiment identifies a ligand involved in a protein-protein interaction in which each of the peptide partners is known, ligands can be identified which are involved in protein-protein interactions wherein only some or none of the peptide partners are known. Specifically, the methods described above for identifying peptide partners (either homotypic or heterotypic) can be utilized in CadC-based cell systems as described for these methods, but further comprising a candidate ligand test peptide construct as described herein. The methods can then be performed as described above, except that the CadC-fusion polypeptide is expressed at a low level and is coexpressed with the candidate ligand test peptide. cadBA reporter construct assays, as well as specificity assays are as above. Utilizing these methods, peptide partners as well as ligands can be identified simultaneously.

5.5. METHODS FOR IDENTIFICATION OF COMPOUNDS THAT MODULATE PROTEIN-PROTEIN INTERACTIONS

The methods of the invention include methods for the identification of compounds which modulate specific protein-protein interactions. Such compounds can act as agonists or antagonists of the specific protein-protein interactions of interest. In general, the CadC-fusion polypeptides and CadC-based systems of the invention are utilized to identify compounds which bring about differential expression of cadBA reporter constructs relative to such expression in the absence of the compounds. A compound's specificity is tested by measuring whether the compound exhibits an effect on a control CadC-fusion polypeptide's activation of cadBA reporter construct expression. Once a compound has been identified via such methods, the compound can further be assayed in native, e.g., mammalian, systems to test the compound's effects on the protein-protein interaction of interest within the interaction's usual biological context.

Compounds that can be tested and identified as modulating protein-protein interactions utilizing the methods described herein can, in general, include any compounds which, upon exogenous addition to the cells of the invention, can enter the cells' periplasmic space or region. In general, such compounds are of a molecular weight up to about 800 to about 1000 daltons. Test compounds can include, but are not limited to, compounds obtained from any commercial source, including Aldrich (1001 West St. Paul Ave., Milwaukee, Wis. 53233), Sigma Chemical (P.O. Box 14508, St. Louis, Mo. 63178), Fluka Chemie AG (Industriestrasse 25, CH-9471 Buchs, Switzerland (Fluka Chemical Corp. 980 South 2nd Street, Ronkonkoma, N.Y. 11779)), Eastman Chemical Company, Fine Chemicals (P.O Box 431, Kingsport, Tenn. 37662), Boehringer Mannheim GmbH (Sandhofer Strasse 116, D-68298 Mannheim), Takasago (4 Volvo Drive, Rockleigh, N.J. 07647), SST Corporation (635 Brighton Road, Clifton, N.J. 07012), Ferro (111 West Irene Road, Zachary, La. 70791), Riedel-deHaen Aktiengesellschaft (P.O. Box D-30918, Seelze, Germany), PPG Industries Inc., Fine Chemicals (One PPG Place, 34th Floor, Pittsburgh, Pa. 15272). Further any kind of natural products may be screened using the methods of the invention, including microbial, fungal or plant extracts.

Furthermore, diversity libraries of test compounds, including small molecule test compounds, may be commercially obtained from Specs and BioSpecs B. V. (Rijswijk, The Netherlands), Chembridge Corporation (San Diego, Calif.), Contract Service Company (Dolgoprudny, Moscow Region, Russia), Comgenex USA Inc. (Princeton, N.J.), Maybridge Chemicals Ltd. (Cornwall PL34 OHW, United Kingdom), and Asinex (Moscow, Russia). Combinatorial libraries of test compounds, including small molecule test compounds, can be may be generated as disclosed in Eichler & Houghten, 1995, *Mol. Med. Today* 1:174–180; Dolle, 1997, Mol. Divers. 2:223–236; Lam, 1997, *Anticancer Drug Des.* 12:145–167. These references are incorporated hereby by reference in their entirety. It is to be noted that such references also teach additional screening methods which may be employed for the further testing of compounds identified via the methods of the invention and which can aid in identifying and isolating compounds which can represent leads and therapeutic compounds having a desired effect on the physiological activity and/or function on the protein-protein interaction of interest.

The CadC-based systems of the invention are uniquely suited for the discovery of molecules that interact protein-protein interaction domains (e.g. with the extracellular domain of a receptor). A molecule, such as a ligand or ligand mimetic, that preferentially binds to the the interactive (e.g., dimeric) state will pull the equilibrium in the direction of the interactive (e.g., dimerized) form by an increment that is proportional to the free energy of that binding preference. Such a moiety will perform a molecular function strictly analogous to that of an agonist, without necessarily bearing any structural similarity to the natural agonsist. Further, there is also no requirement that such a molecule bind to a natural ligand-binding site or other binding site along the protein-protein interaction domain.

The parallel is true for antagonists. A compound (e.g., a small molecule) that preferentially binds to the monomeric form of a protein involved in a protein-protein interaction will pull the equilibrium in the direction of the monomer by an increment that is proportional to the free energy of that binding preference. The formal possibility of a fortuitous allosteric effector increases the numbers and types of molecules that may be considered as candidates for both agonist and antagonist functions.

Figure 4A:
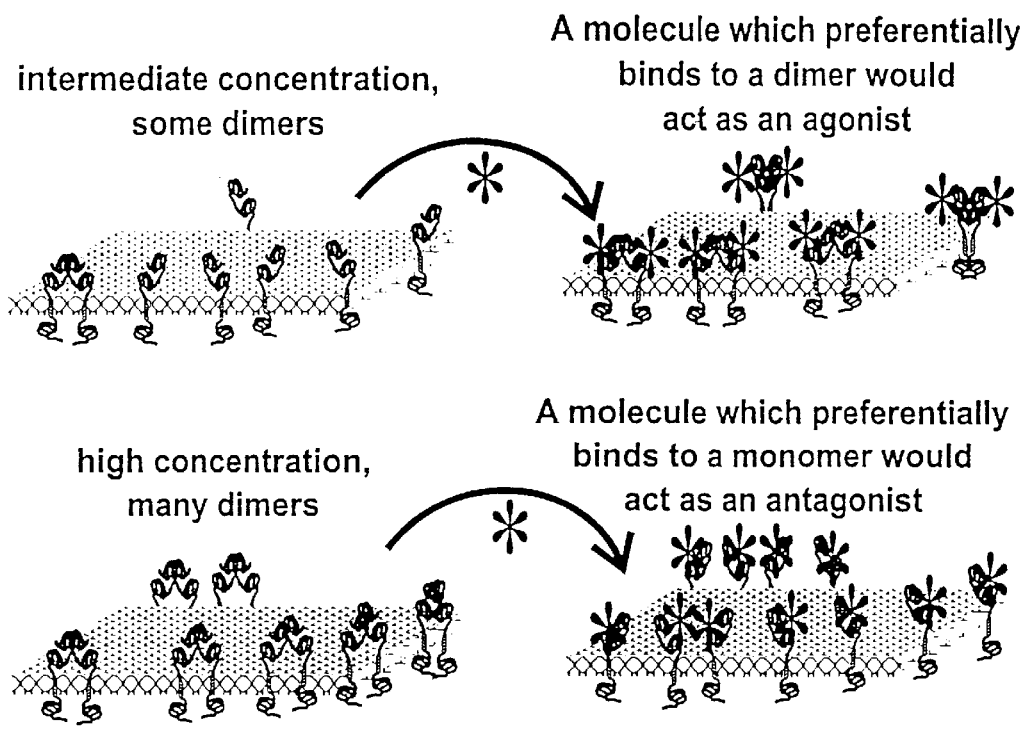
Figure 4B:
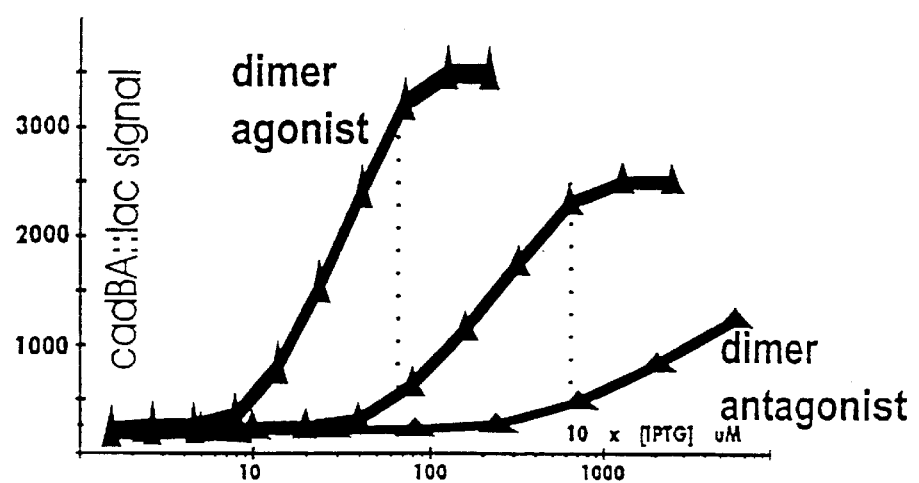

In the CadC-based systems of the invention, the ability to carefully adjust the level of CadC-fusion polypeptide expression allows for poising the system to be optimally sensitive to the detection of such molecules (e.g., agonists and antagonists). FIGS. 4A–4B present diagrammatic representations of the effects an agonist-type and antagonist-type compound have on CadC-fusion polypeptide levels and cadBA reporter gene expression. The Examples presented in Sections 9.2, 10, 11, and 12 demonsrate construction and expression of CadC-fusion polypeptides and their use in methods as described herein.

As discussed above, such methods utilize the CadC-based cell systems of the invention to identify compounds which modulate protein-protein interactions of interest. Modulation is measured via a differential level of cadBA reporter construct expression in the presence of a compound relative to the expression level in its absence. "Modulation" may refer to an increase or a decrease in such cadBA reporter construct expression. In instances wherein the compound causes a specific increase in expression, the compound is considered an agonist, and in instances wherein the compound causes a specific decrease in expression, the compound is considered an antagonist.

Compounds that agonize or antagonize a protein-protein interaction can have a variety of uses depending upon the protein-protein interaction of interest. For example, both EPO and insulin are administered as therapeutic agents. Among the compounds the methods of the invention can identify are small molecule compounds, such as orally acceptable small molecule compounds, representing functional agonists of either EPO receptor or insulin receptor, depending upon the particular Cadc-based cell system utilized for screening. In another example, processes mediated by TNFα cytokine lead to inflammation. In such an example, therefore, an antagonist of the TNFα receptor would be useful. Among the compounds the methods of the invention can identify are small molecule compounds, such as orally acceptable small molecule compounds, representing antagonists of the TNFα receptor.

In general, in CadC-based screens for compounds which act as agonists, the CadC-based cell systems of the invention are incubated under conditions which produce CadC-fusion polypeptide expression levels that are particularly sensitive to revealing increased CadC-fusion polypeptide interaction (e.g., dimerization), as measured via cadBA reporter gene expression. For such agonist screens, CadC-fusion polypeptide expression should be adjusted to levels which, in the absence of test compounds, bring about low, but detectable, levels of cadBA reporter gene expression levels (that is, preferably less than about 50% of maximal expression and most preferably less than about 10% of maximal expression).

In general, in CadC-based screens for compounds which act as antagonists, the CadC-based cell systems of the invention are incubated under conditions which produce CadC-fusion polypeptide expression levels that are particularly sensitive to revealing a decrease in CadC-fusion polypeptide interaction (e.g., dimerization), as measured via cadBA reporter gene expression. For such antagonist screens, CadC-fusion polypeptide expression should be adjusted to levels which, in the absence of test compounds, bring about high, but submaximal, levels of cadBA reporter gene expression levels (that is, no greater than about 60% to about 90% of maximal expression, and preferably about 80% to about 90% of maximal expression).

In one embodiment of a screen for agonist compounds, such methods utilize a CadC-based cell system of the invention comprising a nucleic acid molecule encoding a CadC-fusion polypeptide which comprises a protein-protein interaction domain that contains the peptide that undergoes the protein-protein interaction of interest. The CadC-fusion polypeptide coding sequence is expressed in a manner which results in a low, but detectable, level of cadBA report construct expression as measured by reporter gene sequence expression/activity. For example, in instances wherein the expression of the CadC-fusion polypeptide is under inducible regulation, induction conditions can routinely be determined which will result in the desired level of cadBA reporter construct expression. Successful examples of routine determination of conditions under which desired induction levels can be attained are demonstrated in the Examples presented, below, in Sections 10, 11 and 12.

Such methods comprise incubating the cell under conditions whereby the CadC-fusion polypeptide is expressed at a low level, as discussed above, in the presence and absence of a test compound for a time sufficient to allow interaction between CadC-fusion polypeptides, and measuring cadBA reporter expression. If, for a given low level of CadC-fusion polypeptide expresion, a higher level of cadBA reporter gene expression is measured in the presence of the test compound relative to that measured in its absence, a candidate agonist compound is identified.

In one embodiment of a screen for antagonist compounds, such methods utilize a CadC-based cell system of the invention comprising a nucleic acid molecule encoding a CadC-fusion polypeptide which comprises a protein-protein interaction domain that contains the peptide that undergoes the protein-protein interaction of interest. The CadC-fusion polypeptide coding sequence is expressed in a manner which results in a high, yet submaximal, level of cadBA report construct expression as measured by reporter gene sequence expression/activity. For example, in instances wherein the expression of the CadC-fusion polypeptide is under inducible regulation, induction conditions can routinely be determined which will result in the desired level of cadBA reporter construct expression. Successful examples of routine determination of conditions under which desired induction levels can be attained are demonstrated in the Examples presented, below, in Sections 10, 11, and 12.

Such methods comprise incubating the cell under conditions whereby the CadC-fusion polypeptide is expressed at a high level, as discussed above, in the presence and absence of a test compound for a time sufficient to allow interaction between CadC-fusion polypeptides, and measuring cadBA reporter expression. If, for a given high level of CadC-fusion polypeptide expresion, a lower level of cadBA reporter gene expression is measured in the presence of the test compound relative to its absence, a candidate antagonist compound is identified.

In order to substantiate the specificity of the candidate agonist's or antagonist's effect on cadBA reporter gene expression, the test compound can be incubated in the presence of a second CadC-based cell system, wherein the second cell expresses a control CadC-fusion polypeptide, for a time sufficient to allow interaction between CadC-fusion polypeptides, and cadBA reporter expression can then be assayed. In instances wherein the level of reporter expression is not altered in a statistically significant manner in the presence or absence of test compound, the specificity of the test compound is supported.

A "control CadC-fusion polypeptide," as used herein, refers to a CadC-fusion polypeptide comprising a periplasmic domain containing a protein-protein interaction domain that is not related to the sequences comprising the periplasmic domain of the first CadC-fusion polypeptide. That is, e.g., the periplasmic domain of the CadC-fusion polypeptide is not involved in the same protein-protein interaction as that of the first CadC-fusion polypeptide, and is, in general, neither structurally nor functionally related to the that of the first CadC-fusion polypeptide. For example, a CadC-fusion polypeptide comprising a GCN4 leucine zipper protein-protein domain can be utilized as a control CadC-fusion polypeptide in instances in which the protein-protein interaction of interest does not involve such a GCN4 leucine zipper protein-protein interaction domain, or a homolog thereof.

In instances wherein the protein-protein interaction of interest is normally dependent upon or enhanced by another peptide, e.g., a ligand, methods for identifying either agonist or antagonist compounds can be performed in the presence of such a peptide. Such methods can, for example, utilize CadC-based cell systems as described above, further comprising a nucleic acid molecule encoding the peptide ligand in such a manner as to target the expressed ligand to the cell's periplasmic space. Thus, such methods can be utilized with an autologous ligand system. Details for the construction and preferable characteristics of an autologous ligand system are described, above, in Section 5.4.

With respect to methods for identifying compounds that act as antagonists, the high level of cadBA reporter expression beneficial to the sensitivity of such methods is obtained via ligand-mediated or ligand-dependent CadC-fusion polypeptide interaction, rather than solely by high level-driven ligand independent CadC-fusion polypeptide interaction. Such ligand-mediated CadC-fusion polypeptide interaction can, for example, by obtained by varying either the level of CadC-fusion polypeptide or the level of ligand present in the cell (via, e.g., inducible expression of the CadC-fusion polypeptide or the ligand). Alternatively, such interaction can be obtained by systematically varying both such levels in the cell.

The methods of the invention can routinely be performed in a high throughput fashion for rapidly screening multiple test compounds. In particular, the CadC-based cell systems used in such methods can be expressed and assayed in any multiple copy format known to those of skill in the art, including, but not limited to microtiter plates, spotting on agar plates, agar wells, spotting on chips and the like. Likewise, standard multiple manipulation techniques including but not limited to robotic handling techniques, can be utilized for multiple deposition of cells and/or test compounds.

Once a test compound that exhibits an ability to modulate (either agonize or antagonize) CadC-fusion polypeptide interaction (e.g., dimerization) is identified via the methods of the invention, the test compound can be further analyzed within the appropriate endogenous, native system, eg., an appropriate mammalian system.

Taking a test compound that modulates EPO-R dimerization as an example, such a test compound could be further analyzed in mammalian systems. For example, such a test compound could be analyzed using mammalian cell-based functional assays designed whether the test compound affects functional changes which take place due to erythropoietin binding to EPO-R on the cell surface. Such secondary function-based assays can include, for example, an assay for enhanced synthesis of hemoglobin (Hb), cellular proliferation and/or enhanced synthesis of Glycophorin A.

Regarding assays for Hb production, such assays can include an assay (e.g. fluorometric assay involving, for example phenyl green or calcein) to measure changes in iron amounts pre- and post-stimulation of EPO-R. In addition, for example, Hb pseudoperoxidase activity can be measured, preferably by fluorometric means.

Regarding cell proliferation changes elicited in response to EPO-R stimulation, any standard, well known cell proliferation assay can be utilized. Such assays include, for example, $^3$H-thymidine incorporation and measurements of specific fluorophore binding to DNA.

Regarding Glycophorin A, increased levels are normally observed upon EPO-R stimulation. Levels can be assayed, for example, by utilizing anti-Glycophorin A antibodies.

6. EXAMPLE

Construction of a Cadba-lacz Reporter Construct

Construction of the cadB'-lacZ$^+$ reporter strain was as follows. Primers cadB5(+) 5'TCCCCCCGGGTATAATAT-GTTGCGGC 3' (SEQ ID NO:7), and cadB5(−) 5' CGG-GATCCAGAACTCATGCTCTTC 3' (SEQ ID NO:8) were used to PCR amplify the 5' end of cadB upstream sequences from the chromosome (cadB5). Primers Lac1 (+) 5' CGCG-GATCCACACAGGAAACAGCTATGAC 3' (SEQ ID NO:9) and Lac2(−) 5' CCGCTCGAGACATGGCCTGC-CCGG 3' (SEQ ID NO:10) were used to amplify the lac gene from plasmid pMLB1109 (Turnbough et al., 1983, Proc. Natl. Acad. Sci. USA, 80: 368–72). Primers cadB3' (+) 5' CCGCTCGAGATCGGGCTATTTGCCTG3' (SEQ ID NO:11), and cadB3' (−) 5' GTACGCGTCGACAGCGG-TAATACCAATCGC 3' (SEQ ID NO:12) were used to PCR amplify the 3' end of cadB from the chromosome (cadB3). Subsequent digestion of the PCR products, cadB5 and lacZ, with BamHI and ligation with DNA ligase produced a fusion DNA, cadB5'+lacZ. This product together with PCR product cadB3' was digested with XhoI and re-ligated to produce the final fusion DNA, cadB5'+lacZ+cadB3'. This DNA can be transformed into a recBCD Δlac strain, and the transformants selected on minimal+lactose plate. Transformants containing the cadB'-lacZ$^+$ fusion on chromosome can be verified by PCR amplification and phenotypic assay (as described, e.g., in Section 9.2, below). A XmaI site and SalI site was engineered at the 5' end and 3' end of the fusion DNA, cadB5'+lacZ+cadB3', respectively. This fusion DNA was cloned into the plasmid pRS415 containing these restriction sites.

The cadBA regulatory sequence was also used in constructing the following cadB'-cat$^+$ reporter strain. Primers cat1(+) 5' CCGGGATCCAGGAGCTAAG-GAAGCTAAAATG 3' (SEQ ID NO:13), and cat2(−) 5' CAGGCGTAGCACTCGAGGCGTTTAAG 3' (SEQ ID NO:14) were used to PCR amplify the catGenBlock from the plasmid pCaMVCN (Pharmacia; Uppsala, Sweden). This PCR product was used to replace the lacZ PCR product in the procedure described for the strain above, to form the cadB5'-cat-cadB3' DNA fusion product. This fusion was also cloned into a plasmid as described above.

The cadBA regulatory sequence was used to construct the following cadA'-lacZ$^+$ and cadA'-cat$^+$ reporter strains. Primers cadB5(+) (described above) and CadA(−) 5' CAGTTTGTGAGTCGACTGGGTTTC 3' (SEQ ID NO:15; with a SalI at the 3' end) were used to PCR amplify the DNA fragment containing cadB and part of cadA from the chromosome. This fragment was digested by XhoI and blunt-ended by filling-in with Klenow. The PCR product of lacZ and cat was also digested by appropriate enzymes and Klenow-filled in. Fusion DNA, cadBA'+lacZ+'cadA or cadBA'+cat+'cadA was generated through DNA ligation. The subsequent steps were similar to those described for constructing the cadB fusions.

7. EXAMPLE

Construction of a cadC$^−$ Construct

Described herein is the generation of a cadC$^−$ construct for use in construction of a cadC::kan E. coli strain using fusion PCR techniques to produce a cadC$^−$ strain. Compared with traditional methods utilizing gene replacement via "suicide vectors," either of the two techniques described below were relatively simpler for such strain construction.

Primers cadC5(+) 5'CCCAAGCTTCATTCCCTTTTC-GAATG3' (SEQ ID NO:16), and cadC5(−) 5'CAGGTTTC-CCTCTAGAGTCACGACGCTTTGGTACAGTAGCG3' (SEQ ID NO:17) were used to PCR amplify 316 bases from the 5' end of the cadC gene from the E. coli chromosome (referred to herein as "cadC5'") using standard PCR amplification techniques. The cadC5(−) primer was designed such that it added a 24-base tag at the 3' end of cadC5.

Primers cadC3(+) 5'TCCTGAGTGTCGACAAATTGC-CGCGCGGCTATAAATTAATGGTG3' (SEQ ID NO:18) and cadC3(−) 5'TGCTCTAGATTGAGCAAAATACGCG3' (SEQ ID NO:19) were used to PCR amplify 299 bases from the 3' end of cadC from the E. coli chromosome (referred to herein as "cadC3'") using standard PCR amplification techniques. Primer cadC3(+) was designed such that it added a 24-base tag2 at the 5' end of cadC3'.

Primers kan(+) 5'GTCGTGACTCTAGAGGGAAAC-CTGGAAAGCCACGTTGTGTCTC3' (SEQ ID NO:20) and kan(−) 5' CGGGCAATTTGTCGACACTCAGGAGC-CGCCGTCCCGTCAAGTC3' (SEQ ID NO:21) were used to PCR amplify the kanamycin resistance sequence from the plasmid pUC4K (kanBlock; L. A. Taylor & R. E Rose, 1988, Nucleic Acid Res. 16:358) using standard PCR amplification techniques. The amplified kanBlock sequence was flanked by tag1 and tag2 at its 5' and 3' ends, respectively.

Next, primers cadC5(+) and kan(−) were used to PCR amplify a fusion DNA of cadC5' plus kanBlock (cadC5'+kanBlock), using cadC5' and kanBlock as templates and following standard PCR amplification techniques.

Third, primers cadC5(+) and cadC3(−) were used to PCR amplify a fusion DNA of cadC5' plus kanBlock plus cadC3' (cadC5'+kanBlock+cadC3'), from the templates cadC5'+kanBlock and cadC3', using standard PCR amplification techniques.

This cadC5'+kanBlock+cadC3' PCR product can then be transformed into a recBCD E. coli strain using standard techniques. The transformants are selected on LB+Kan (25 mg/ml) plates to contain the cadC::kan insertion on the chromosome.

The cadC5'+kanBlock+cadC3' fusion DNA was also made by connecting the three pieces of DNA, i.e., cadC5', kanBlock and cadC3' directly by DNA ligation. To achieve this, a XbaI site and a SalI site were engineered into the tag1 and tag2 sequences, respectively. The PCR products cadC5' and kanBlock were cut by XbaI and ligated together using standard DNA ligase techniques to form the fusion DNA, cad5'+kanBlock. This fusion DNA, together with cadC3, was cut by SalI and re-ligated to form the final three-piece fusion product which can be used for transformation.

8. EXAMPLE

Construction of a CadB'-lacZ$^+$ Reporter Strain

An E. coli cadB'-lacZ+ strain containing a cadBA reporter construct comprising a lacZ reporter gene sequence was constructed as described herein.

Primers cadB5(+) 5'TCCCCCCGGGTATAATATGT-TGCGGC3' (SEQ ID NO:22) and cadB5(−) 5' CGGGATC-CAGAACTCATGCTCTTC3' (SEQ ID NO:23) were used to PCR amplify the 5' end of *E. coli* cadB upstream sequences from the chromosome using standard PCR amplification techniques. The amplified fragment is referred to herein as "cadB5'".

Primers Lac1 (+)5'CGCGGATCCACACAGGAAACAGCTATGAC3' (SEQ ID NO:24) and Lac2(−) 5'CCGCTCGAGACATGGC-CTGCCCGG3' (SEQ ID NO:25) were used to amplify the lac gene from plasmid PMLB1109 (Turnbough et al., 1983, Proc. Natl. Acad. Sci. USA 80:368–372) using standard PCR amplification techniques. The amplified sequence is referred to herein as "lacZ".

Primers cadB3'(+)5' CCGCTCGAGATCGGGC-TATTTGCCTG3' (SEQ ID NO:26) and cadB3'(−) 5'GTACGCGTCGACAGCGGTAATACCAATCGC3' (SEQ ID NO:27) were used to PCR amplify the 3' end of cadb from the *E. coli* chromosome using standard PCR amplification techniques. The amplified sequence is referred to herein as "cadB3'".

Subsequent digestion of the PCR products cadB5 and amplified lacZ with BamHI and ligation with DNA ligase produced a fusion DNA of cadB5' plus lacZ (cadB5'+lacZ).

cadB5'+lacZ, together with PCR product cadB3', was digested with XhoI and re-ligated to produce a final fusion DNA of cadB5' plus lacZ plus cadB3' (cadB5'+lacZ+cadB3'). A XmaI site and SalI site were engineered at the 5' end and 3' end of the fusion DNA, cadB5'+lacZ+cadB3', respectively, thus allowing the fusion DNA to easily be cloned into sequences with these restriction sites.

This fusion DNA can be transformed into a recBCD Δlac strain, and the transformants were selected on minimal+ lactose plate. The transformants contain the cadB'-lacZ⁺ fusion on the chromosome, as verified by PCR amplification and phenotypic assay (see Section 9.2, below).

9. EXAMPLE

Production and Expression of a CadC-fusion Polypeptide and a CadC-based Cell System Described herein are, first, the successful constructions of CadC-fusion polypeptides comprising a periplasmic domain comprising a leucine zipper protein-protein interaction domain of the yeast transcriptional activator GCN-4 (Agre t al., 1989, Science 246:922–926) and *E. coli* CadC transmembrane and transcriptional regulatory domains. Among the studies presented herein are experiments demonstrating the routine identification of two regions within the CadC sequence that can act as fusion junctions in the construction of CadC-fusion polypeptides (referred to herein as junctions 1 and 2), as well as the routine identification of a CadC region which should generally be avoided as a possible fusion junction (referred to herein as junction 5).

In addition, the successful construction of a CadC-based system in *E. coli* is described, wherein the system comprises a CadC⁻ *E. coli* cell containing the above-described CadC-fusion polypeptides and nucleic acids encoding them, as well as a cadBA reporter construct comprising a lacZ reporter gene sequence.

The data characterizing these CadC-fusion polypeptides and systems represent the first actual demonstration of a relationship between CadC dimerization and transcriptional activation functions for the CadC gene product.

9.1. Construction of CadC-fusion Polypeptide Coding Sequences

The periplasmic domains of the CadC-fusion polypeptides discussed in this Example comprised either a wild type leucine zipper protein-protein interaction domain of the GCN4 protein (wt), or a dimerization-defective GCN4 mutant with a proline substitution at GCN4 leucine zipper amino acid position 19. The CadC-fusion polypeptides were constructed using junctions 1 or 2 or 5, as described below.

As a first step in creating a CadC-fusion polypeptide utilizing junction 1, a cadC gene sequence truncated at junction 1 was generated by PCR amplification of the *E. coli* chromosomal cadC gene using primer 1 (5' CCCCAAGCT-TCATTCCCTTTTCGAATG 3'; SEQ ID NO:28); HindIII at the 5' end) and primer 2 (5' TGCGGTCGAAGACT-TGAAAACGCTACC 3' SEQ ID NO:29; SalI at the 5' end) and standard PCR amplification techniques. As noted in FIG. 2, junction 1 lies within the CadC transmembrane domain.

This PCR amplified fragment was then digested with HindIII and SalI, gel purified and ligated into gel purified HindIII and SalI digested plasmid pCL1921 (Lerner C. G., Inouye M., 1990, Nucleic Acids Res. 18:4631–35) employing standard molecular biology techniques (Sambrook et al., supra), thereby producing an intermediate plasmid in the construction.

In a second step, the leucine zipper of GCN4 was isolated by PCR amplification from the plasmid pJH370 (Hu et al., 1990, Science 250:1400–1403) employing the following primers: 5' ACGCGTCGACACATATGAAAC3' (SEQ ID NO:30), SalI at the 5' end; and 5' GCTTGGATCCT-CAACGTTC 3' (SEQ ID NO:31), a BamHI at the 5' end) and standard PCR amplification techniques.

To produce plasmid pCCZ1-wt (FIG. 5), which contains the coding sequence for the CadC-fusion polypeptide comprising the wild type GCN4 leucine zipper, the GCN4 leucine zipper PCR product was digested with BamHl and SalI, gel purified, and ligated to a BamHl and SalI digestion product of the intermediate plasmid using standard techniques. To confirm the integrity of the product construction, DNA sequence analysis was performed, extending from the lacOP region through end of the CadC-fusion polypeptide coding sequence. This sequence is depicted in FIG. 5, along with schematic diagrams of the relevant portions of the plasmid. Sequence analysis also confirmed the construction of the plasmids described below.

To produce a plasmid (PCCZ1-lp19) containing the coding sequence for the CadC-fusion polypeptide comprising the GCN4 leucine zipper dimerization-defective mutant, the same steps as described above were employed starting with the plasmid pJH524 (Hu et al., supra), which contained a coding sequence for this GCN4 mutation.

A second set of plasmids (pCCZ4-wt and PCCZ4-lp19) were constructed employing CadC junction 2. As noted in FIG. 2, junction 2 lies within the CadC periplasmic domain. PCCZ4-wt encodes a CadC-fusion polypeptide comprising the wild type GCN4 leucine zipper sequence, while PCCZ4-lp19 encodes a CadC-fusion polypeptide comprising the GCN4 mutant dimerization-defective sequence.

The coding sequences for these CadC-fusion polypeptides were produced in a manner similar to the steps described above, except the truncated cadC sequence was amplified using primer 1 and a primer 2 appropriate to the producing a cadC sequence ending at junction 2. In particular, this primer 2 was as follows: 5' TGCGGTCGACAATTTTATC-GACATAAAG 3' (SEQ ID NO:32), SalI at the 5' end.

A CadC-fusion polypeptide set was also generated utilizing junction 5, as noted in FIG. 2. The same construction steps were utilized as above, with appropriate modifications made to primer 2 such that the desired truncated CadC coding sequences were generated. Junction 5 was chosen and tested based on ToxR truncations generated and reported to be successful in the system employed by Menzel & Taylor (U.S. Pat. Nos. 5,521,006 and 5,744,341, collectively, "Menzel & Taylor") to study dimerization using Vibrio cholerae ToxR in the heterologous system of *E. coli*. As discussed below, in Section 9.2, however, junction 5 did not support CadC-fusion polypeptides that could self-interact and drive interaction-dependent transcription from cadBA regulatory sequences. It is also noted that in the heterologous Vibrio system in *E. coli*, Menzel & Taylor reported that a chimera made utilizing a Vibrio junction at a Vibrio position corresponding to junction 4 depicted in FIG. 2 resulted in a chimera which dimerized in a ligand independent manner. In view of this undesirable Vibrio result, therefore, the successful use of junction 2 in CadC, which results in a substantially shorter CadC protein than would a truncation at junction 2, is a very surprising one.

9.2. Construction of a CadC-based Cell System and Characterization of CadC-fusion Polypeptide-dependent Activation of cadBA Reporter Construct Transcription Plasmids from the sets (i.e., pCCZ1-wt and lp19, and pCCZ4-wt and lp19) described above in Section 9.1, were each, independently, transformed into the CadC⁻ *E. coli* host strain E2088 (see Section 5.3, above), thereby generating a CadC-based cell system comprising an *E. coli* CadC⁻ cell containing a cadBA reporter construct, and a CadC-fusion polypeptide and nucleic acid molecules encoding the CadC-fusion polypeptide.

Multiple transformation products from each plasmid were then singly assayed for β-galactosidase activity. In particular, individual transformants were picked to individual wells of a microtiter plate and grown in 200 µl Luria Broth plus 25 µg/ml spectinomycin without shaking at 37° C. for 8 hours. At the end of the growth period, cell turbidity was measured at 600 nm, the cells were made permeable by chloroform treatment, and aliquots were assayed for β-galactosidase activity using the substrate chlorophenol red β-D-galactoside (CPRG; Eustice et al., 1991, Biotechniques 11:739–742), essentially as described by Menzel (Menzel R., 1990, Anal. Biochem 181:40–50).

Figure 6:
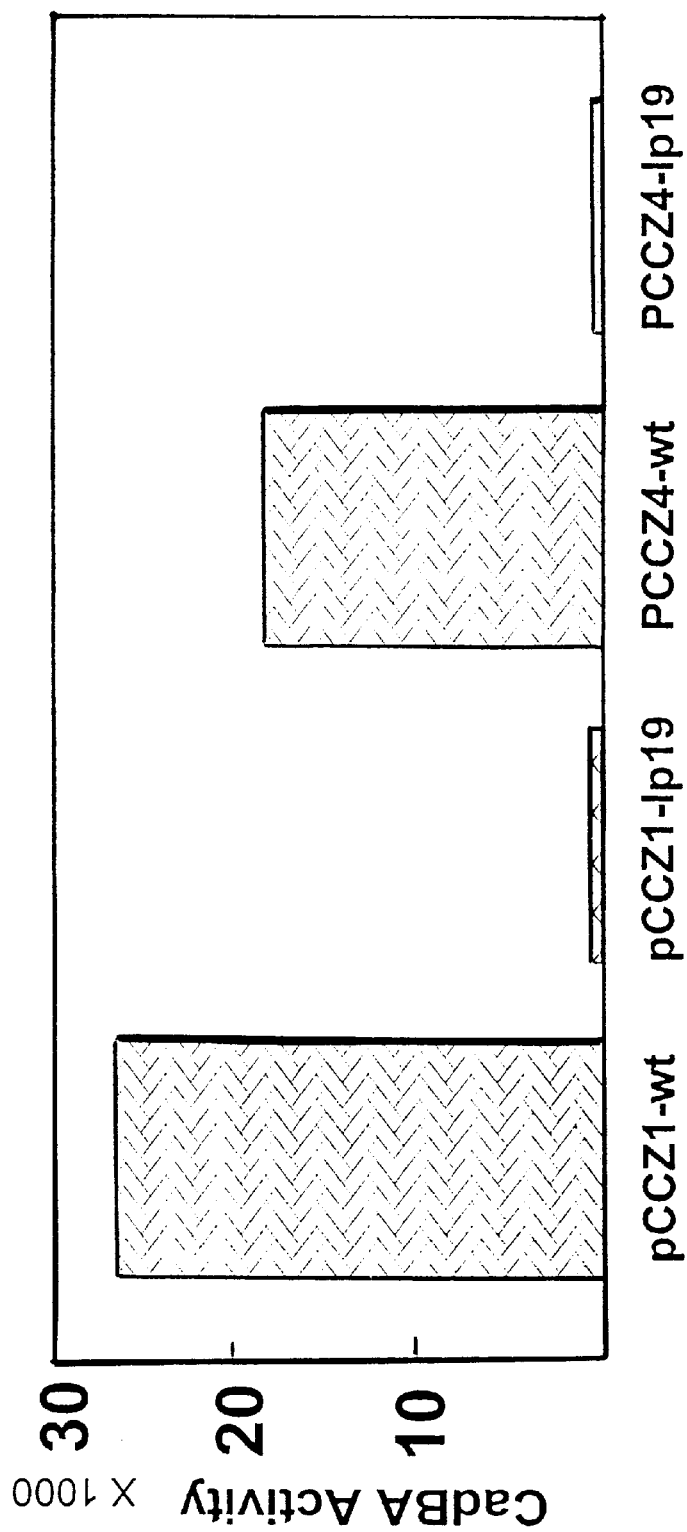

The data presented in FIG. 6 summarize the results obtained from these experiments was an average (values +/−10%) for 4 independent colonies. These results show that robust cadBA reporter construct transcriptional activity, as measured by expression of the lac reporter gene sequence, was generated by CadC-fusion polypeptides produced using either junctions 1 or 2. In addition, these results show that the cadBA activation was dependent upon protein-protein interaction between CadC-fusion polypeptides in that cadBA expression was not observed in the presence of the dimerization-incompetent CadC fusion polypeptides (i.e., those encoded by pCCZ1-lp19 and pCCZ4-lp19 sequences). These experiments mark the first demonstration of a relationship between dimerization and transcriptional activation functions for the CadC gene.

The above assays were also employed to test transformants expressing a CadC-fusion polypeptide generated using junction 5. Such a CadC-fusion polypeptide, however, failed to result in CadC-fusion polypeptide interaction-dependent activation of transcription from cadBA regulatory sequences.

10. EXAMPLE

Construction and Characterization of a EpoR CadC-Fusion Polypeptide and CadC-Based Cell System The Example presented herein describes the successful construction and characterization of a EpoR CadC-fusion polypeptide and CadC-based cell system. Such CadC-fusion polypeptides and CadC-based cell systems form the basis for screens to identify compounds (e.g., Epo functional mimetics) that modulate Epo and EpoR activity. For example, EPO is administered as a therapeutic agent to stimulate receptor signalling. The CadC-based cell system described here can, e.g., be utilized as part of methods to identify compounds, such as orally acceptable small molecule compounds, which act as functional agonists that can be administered in place of EPO. The CadC-based cell system described here was successfully utilized to identify candidate agonists of the EPO/EPOR protein-protein interaction.

The CadC-fusion polypeptides constructed here comprised periplasmic domains containing an extracellular erythropoietin receptor (EpoR) domain linked to *E. coli* CadC coding sequence at junction 1. The steps followed for the construction are described below.

To obtain the EpoR sequences, the following PCR primers

5' CTGTATCATGGACCACCTCGGGGCG 3' (SEQ ID NO:33) and

5' TGCAGCCTGGTGTCCTAAGAGCAAGC 3' (SEQ ID NO:34)

were used to amplify EpoR from a human placenta Marathon-ready cDNA library (Clontech) using the Advantage-HF PCR kit (Clontech) according to the vendor's recommendations. The resulting PCR fragments were cloned into the PGEM-T vector and transformed into the host strain JM109 (Promega). Fidelity of the product was verified by DNA sequence analysis according the standard procedures. The extracellular domain of the Epo receptor was PCR amplified from the resulting pGEM-T clone using the following primers:

5' ACGCGTCGACCCACCTGTACCCCGGAGAGGT 3' (SEQ ID NO:35), SalI 5' end; and

5' CGCGGATCCTACGCATCCTGCCCATCGAACTC 3' (SEQ ID NO:36), BamHI 5' end using standard PCR amplification techniques.

Figure 7B:
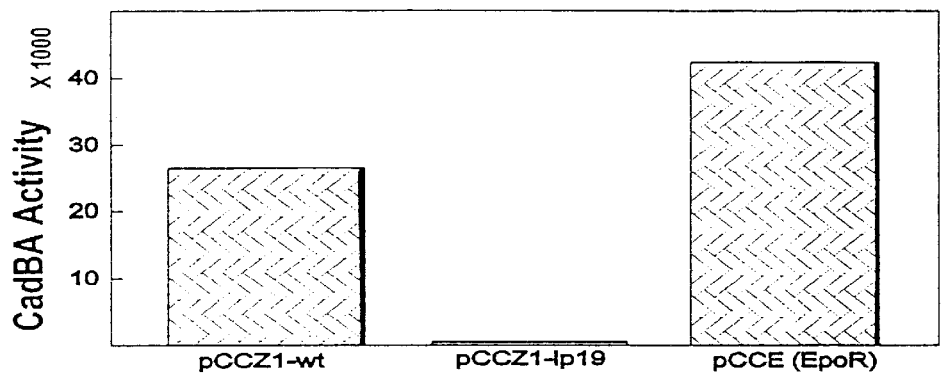

The defective LP19 GCN4 leucine zipper domain was excised from the plasmid pCCZ1-lp19 (see Section 9.1, above) by digestion with SalI and BamHI, and replaced with the SalI and BamHI piece produced by digesting the PCR fragment of the EpoR extracellular domain employing standard molecular biology techniques (Sambrook et al., supra). The DNA sequence of the chimera in the resulting plasmid (pCCE, FIG. 7A) was determined to confirm integrity of the construction.

The plasmid PCCE was transformed into E2088 and 4 independent isolates were assayed (together with clones derived from control plasmids pCCZ1-wt and pCCZ1-lp19) according to the procedures described in Section 9.2, above. The results shown in FIG. 7B demonstrate that the CadC-fusion polypeptide comprising an EpoR protein-protein interaction domain supported robust CadC-fusion polypeptide interaction-dependent activation of transcription from cadBA regulatory sequences. In fact, such activation was even more pronounced than that seen with the CadC-fusion polypeptide comprising a GCN4 leucine zipper domain.

In order to produce a sequence encoding a CadC-fusion polypeptide whose expression is tightly regulated, the coding and associated regulatory region of the CadC-fusion polypeptide described above were recloned from the plasmid pCCE into the plasmid pMS421, a plasmid containing the lacI$^Q$ gene (Maloy et al., 1989, Genetic Analysis of Pathogenic Bacteria. Cold Spring Harbor Laboratory, Cold Spring Harbor, N.Y.). The plasmid pMS421 is based on the parental plasmid pSC101 (a low and stable copy number plasmid) and has the repressor gene, lacI$^Q$, which can be utilized to control and elicit inducible expression of the CadC-fusion polypeptide (which is here transcribed from the wild type lac promoter).

Figure 7C:
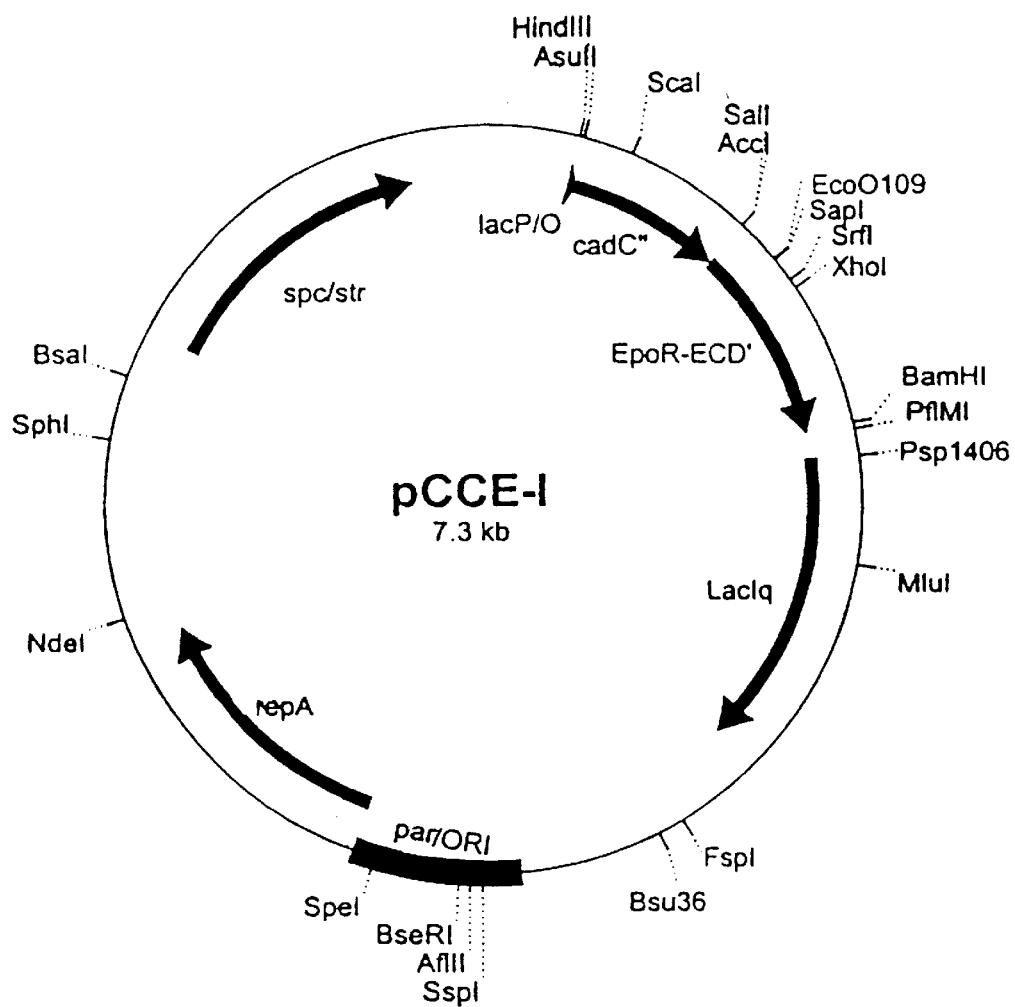

To accomplish this recloning, pCCE was digested with HindIII and BspHl, and the appropriate CadC-EpoR containing fragment purified following gel electrophoresis. This piece was then ligated into BamHl- and HindIII- digested pMS421. After an initial ligation to rejoin the cohesive HindIII ends, the ligation mixture was treated to blunt the remaining BspH1 and BamH1 termini employing a standard Klenow fragment nucleotide "filling in" procedure. The two blunt ends were then rejoined by a subsequent ligation step to produce the required plasmid PCCE-I (FIG. 7C).

pCCE-I was then transformed into strain SMT0001 (a cadBA-lac reporter and cadC: :Tn10 derivative of strain RFM443; see below) and two isolated colonies were purified and inoculated into the well of a microtiter plate containing 200 µl of Luria Broth with 25 µl/ml spectinomycin. Growth was continued at 37° C. without shaking until all the wells became turbid (about 3 hours).

Figure 7D:
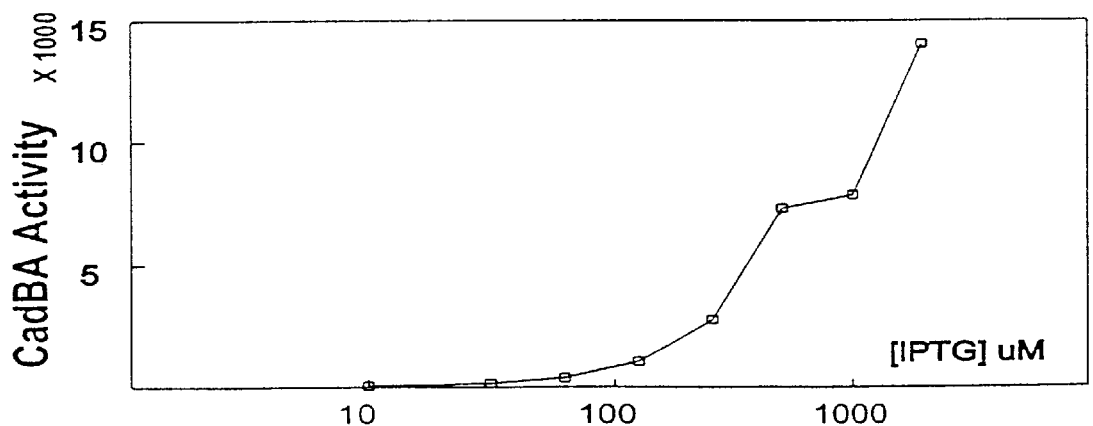

For induction of CadC-fusion polypeptide expression, 15 µl of the above cells were inoculated into 200 µl of Luria Broth with 25 µl/ml spectinomycin and various concentrations of IPTG (in separate wells) at the concentration values indicated in FIG. 7D. The microtiter plate was then incubated for 5 hours at 37° C. and β-galactosidase assays were performed as described in Section 9.2, above. The results depicted in FIG. 7D show the averages of the results obtained with two isolated colonies plotted against the IPTG concentration employed during the second growth interval. Increasing the IPTG concentration, and therefore the level of the EpoR CadC-fusion polypeptide produced, yielded increasing levels of cadBA transcription (monitored by the Lac reporter gene). This ability to control levels of CadC-fusion polypeptides is beneficial to performance of the methods of the invention.

To obtain an even greater fold induction by IPTG, a variety of different E. coli strains were examined as potential hosts. All candidate strains were engineered to comprise a cadBA-lac reporter construct and cadC::Tn10 CadC-allele. This was accomplished using standard P1 phage-mediated transductional crosses to move the cadBA-lac reporter and the cadC::Tn10 from E2088 into the various strains, employing standard genetic techniques (Silhavy et al., Experiments with Gene Fusions, 1984, Cold Spring Harbor Laboratory, New York) and using a double drug selection (tetracycline at 25 µg/ml and kanamycin at 35 µg/ml) to require inheritance of the desired markers. Of the strains examined, RFM443 (Drolet et al., 1995, Proc. Natl. Acad. Sci USA 92:3526–3530) and JM109 (Promega; Madison, Wis.) derivatives yielded the largest induction values. For example, strain SMT0001, described above, represents an RFM443 derivative containing a cadBA reporter and CadC::Tn10 insertion, and strain SMT0002 represents a JM109 derivative carrying such a cadBA reporter and cadC:TN10 insertion.

Figure 7E:
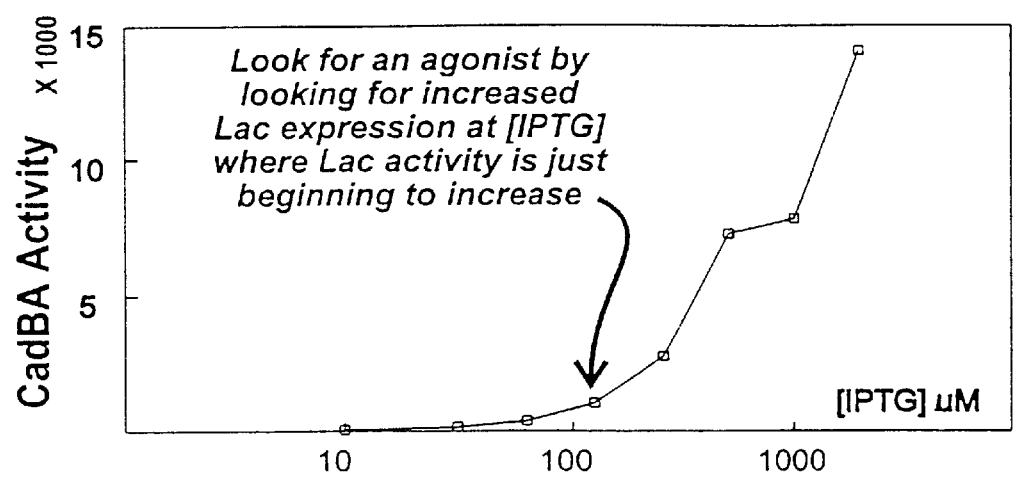

As shown in FIG. 7D, in the CadC-based cell system containing pCCE-I, expression of cadBA lac reporter expression could be titrated with increasing levels of the induce IPTG. FIG. 7E depicts the strategy utilized for choosing an appropriate IPTG concentration for performing an agonist screen, e.g., a screen for identifying functional mimetics of the EPO growth factor. By choosing an appropriate level of IPTG to perform a sensitive agonist screen, it was possible to use the strain to detect compounds that enhanced expression of cadBA-lac.

11. EXAMPLE

Construction and Characterization of an Insulin Receptor CadC-Fusion Polypeptide and CadC-Based Cell System The Example presented herein describes the successful construction and characterization of an insulin receptor (InsR) CadC-fusion polypeptide and CadC-based cell system. Such CadC-fusion polypeptides and CadC-based cell systems form the basis for screens to identify compounds (e.g., insulin functional mimetics) that modulate insulin and insulin receptor activity. For example, insulin is administered as a therapeutic agent to stimulate receptor signalling. The CadC-based cell system described here can, e.g., be utilized as part of methods to identify compounds, such as orally acceptable small molecule compounds, which act as functional agonists that can be administered in place of insulin. The CadC-based cell system described here was successfully utilized to identify candidate agonists of the insulin/InsR protein-protein interaction.

The insulin receptor is more complex than the Epo receptor. It consists of two subunits processed from a single precursor and joined by interchain disulfide linkages (Boni-Schnetzler et al., 1986, J. Biol. Chem. 261:15281–15287). The amino-proximal α subunit contains the insulin binding domain (Mynarcik et al., 1997, J. Biol. Chem. 272::18650–18655) and two α subunits have been shown to be crosslinked to one another by a carboxyl proximal disulfide (Sparrow et al., 1997, J. Biol. Chem. 272:29460–29467). All amino acid sequences involved in insulin binding are amino proximal to the inter-α subunit disulfide linkage.

To create the InsR-containing CadC-fusion polypeptide depicted herein, therefore, a protein-protein interaction domain comprising an insulin receptor α subunit extracellular domain (αECD) sequence was utilized. In particular, the CadC-fusion polypeptides constructed here comprised periplasmic domains containing an extracellular insulin receptor α subunit domain linked to E. coli CadC coding sequence junction 1.

To obtain InsR sequences, the following PCR primers,

5' GCCTGATCCGAGGAGACCCCGCG 3' (SEQ ID NO:37) and

5' GTAGGCACTGTTAGGAAGGATTGGACCGA 3' (SEQ ID NO:38), were used to amplify InsR from a human placenta Marathon-ready cDNA library (Clontech) using the Advantage-HF PCR kit (Clontech) according to the vendor's recommendations. The resulting PCR fragments were cloned into the pGEM-T vector and transformed into the host strain JM109 (Promega). Fidelity of the product was verified by DNA sequence analysis according to standard procedures.

To construct the CadC-fusion polypeptide coding sequence, the inter-α subunit disulfide linkage distal segment of the Insulin receptor was PCR amplified (from the above pGEM-T clone) using the following PCR primers:

5' ACGCGTCGACCCACCTGTACCCCGGAGAGGT 3' (SEQ ID NO:39); SalI site 5' end) and

5' CGCGGATCCTACGCATCCTGCCCATCGAACTC 3' (SEQ ID NO:40); BamHI 5' end) and standard PCR amplification techniques.

The defective LP19 GCN4 leucine zipper domain was excised from plasmid pCCZ1-lp19 (see Section 9.1, above) by digestion with SalI and BamHI, and replaced with the SalI and BamHI piece produced by digesting the PCR fragment of the InsR domain employing standard molecular biology techniques (Sambrook et al., supra). The DNA sequence of the InsR-containing CadC-fusion polypeptide coding region in the resulting plasmid (pCCI, FIG. 8A) was determined to confirm integrity of the construction.

The plasmid pCCT was transformed into E2088 and 4 independent isolates were assayed (together with clones derived from control plasmids pCCZ1-wt and pCCZ-lp19) according to the procedures described in Section 9.2, above. The results shown in FIG. 8B demonstrate that the CadC-fusion polypeptide comprising a IndR receptor protein-protein interaction domain supported robust CadC-fusion polypeptide interaction-dependent activation of transcription from cadBA regulatory sequences.

Figure 8A:
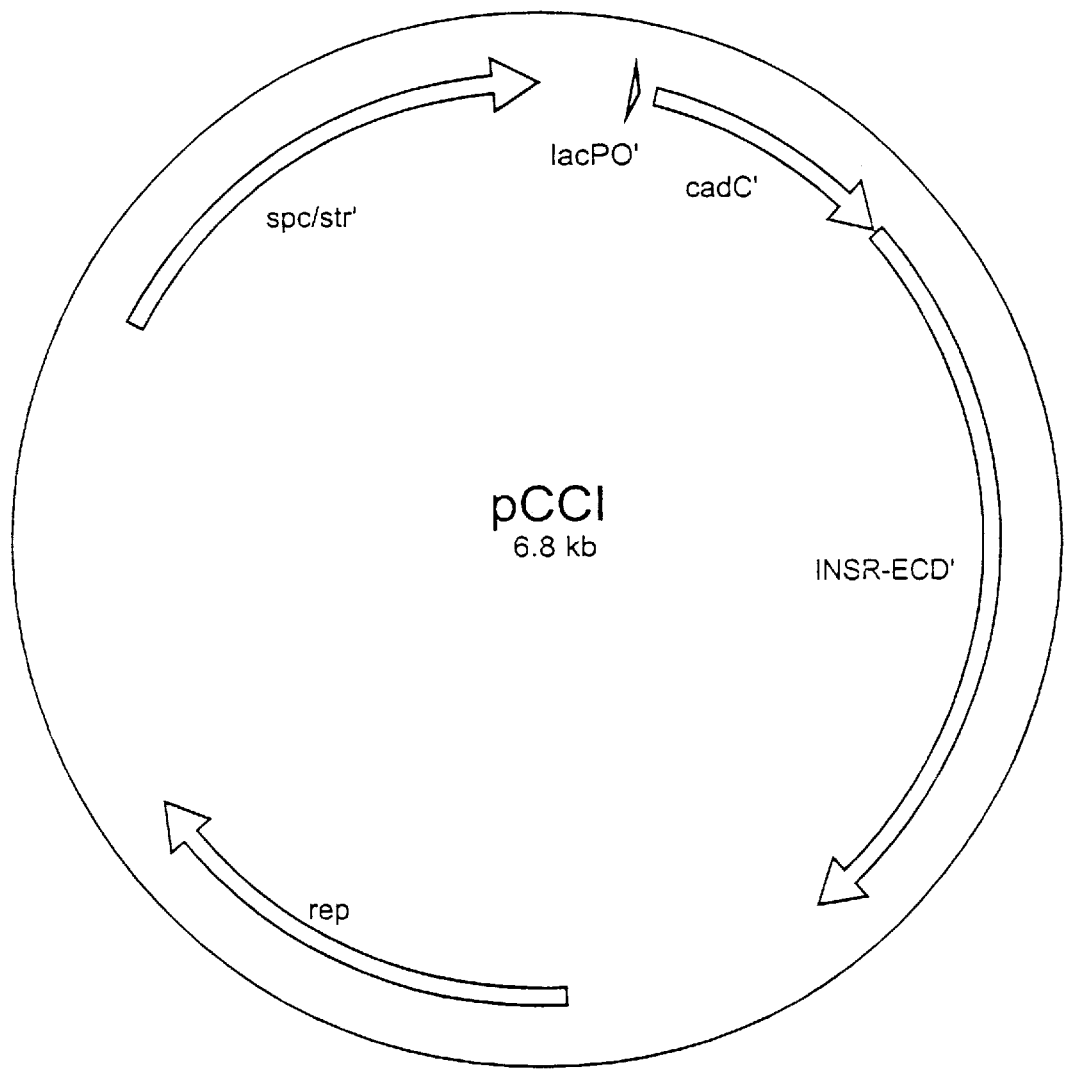
Figure 8B:
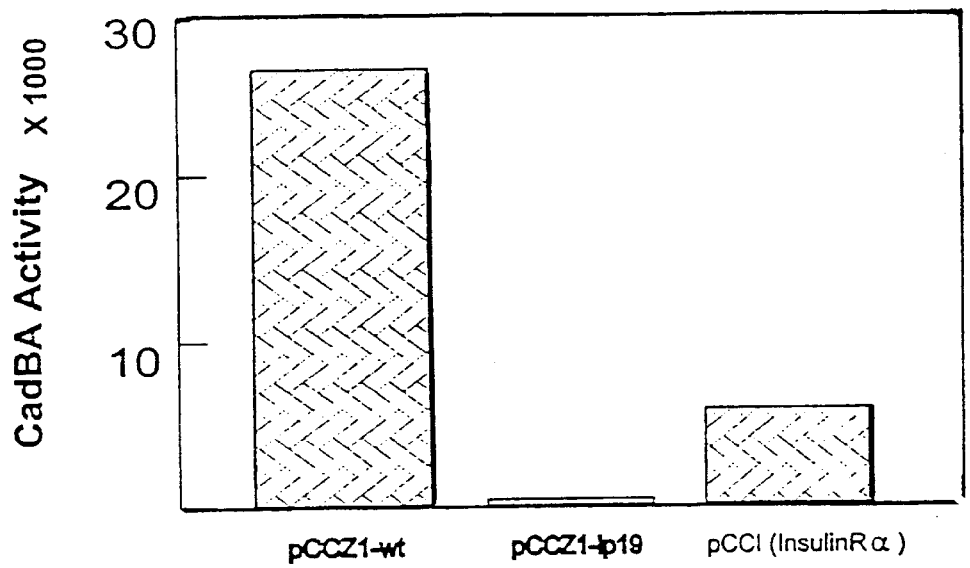
Figure 8C:
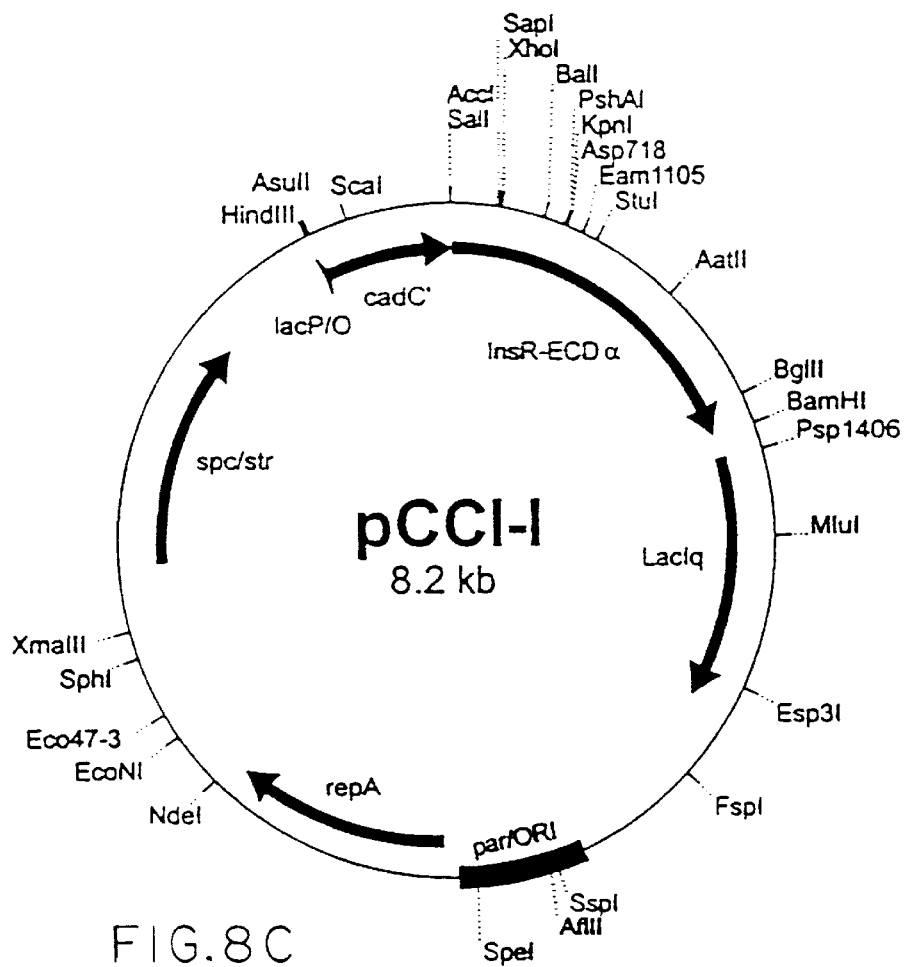

In order to produce a sequence encoding a CadC-fusion polypeptide whose expression is tightly regulated, the coding and associated control region of the CadC-fusion polypeptide described above were recloned from the plasmid pCCI into the plasmid pMS421 as described for pCCE-I above in Section 10. A map of the resulting plasmid, PCCI-I, is shown in FIG. 8C.

The plasmid pCCI-I was transformed into SMT0001 (see Section 10, above) and two isolated colonies were purified and inoculated into the well of a microtiter plate containing 200 µl of Luria Broth with 25µl/ml spectinomycin.

Growth was continued at 37° C. without shaking until all the wells became turbid (about 3 hours).

Figure 8D:
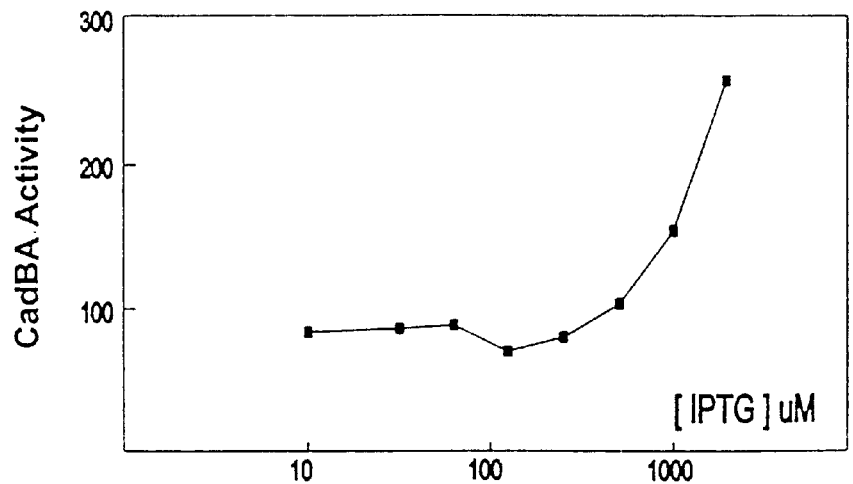

For induction of CadC-fusion polypeptide expression, 15 µl of the above cells were inoculated into 200 µl of Luria Broth with 25 µl/ml spectinomycin and various concentrations of IPTG (in separate wells) at the concentration values indicated in FIG. 8D. The microtiter plate was then incubated for 5 hours at 37° C. and β-galactosidase assays were performed as described in Section 9.2, above. The results in FIG. 8D show the averages of the results obtained with two isolated colonies plotted against the IPTG concentration employed during the second growth interval. Increasing the IPTG concentration, and therefore the level of the InsR CadC-fusion polypeptide produced, yielded increasing levels of cadBA transcription (monitored by the Lac reporter gene).

Figure 8E:
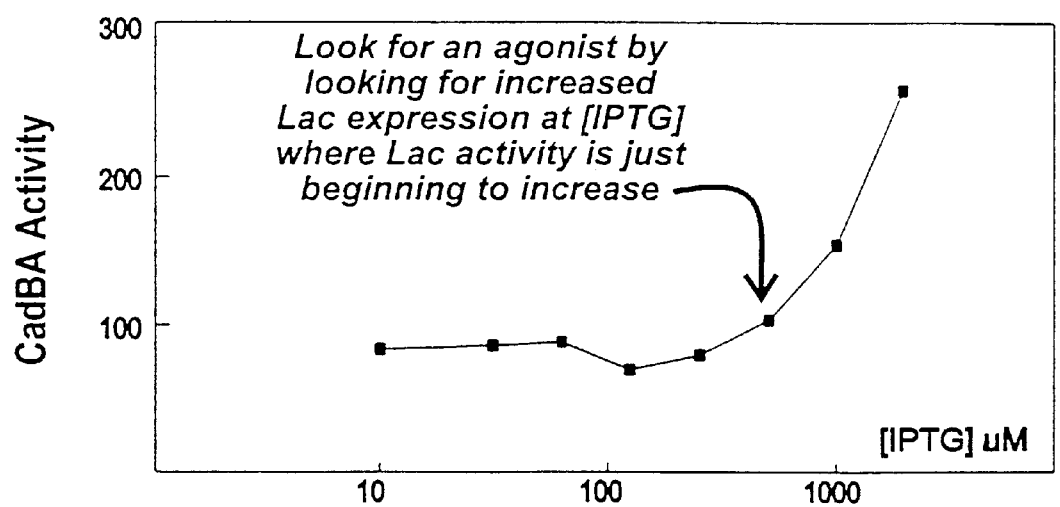

This ability to control levels of CadC-fusion polypeptides is beneficial to performance of the methods of the invention. FIG. 8E depicts the strategy utilized for choosing an appropriate IPTG concentration for performing an agonist screen, e.g., a screen for identifying functional mimetics of the insulin. By choosing an appropriate level of IPTG to perform a sensitive agonist screen, it was possible to use the strain to detect compounds that enhanced expression of cadBA-lac.

12. EXAMPLE

Construction and Characterization of a TNFα Receptor CadC-Fusion Polypeptide and CadC-Based Cell System The Example presented herein describes the successful construction and characterization of a TNFα receptor (TNFαR) CadC-fusion polypeptide and CadC-based cell system. Such CadC-fusion polypeptides and CadC-based cell systems form the basis for screens to identify compounds (e.g., TNFα antagonists, which could be utilized as inflammation inhibitors) that modulate TNFα and TNFα receptor activity. For example, the CadC-based cell system described here can, e.g., be utilized as part of methods to identify compounds, such as orally acceptable small molecule compounds, which act as functional antagonists that can be administered as inhibitors of TNFα. The CadC-based cell system described here was successfully utilized to identify candidate antagonists of the TNFα/TNFαR protein-protein interaction.

In particular, the CadC-fusion polypeptides constructed here comprised periplasmic domains containing an extracellular TNFα domain linked to E. coli CadC coding sequence junction 1.

To obtain the TNFα receptor sequences, the following PCR primers

5' TGTCTGGCATGGGCCTCTCCACCGT 3' (SEQ ID NO:41) and

5' GGAAGGCGATCTCCGAGGACGGTCC 3' (SEQ ID NO:42)

were used to amplify TNFα from a human placenta Marathon-ready cDNA library (Clontech) using the Advantage-HF PCR kit (Clontech) according to the vendor's recommendations. The resulting PCR fragments were cloned into the pGEM-T vector and transformed into the host strain JM109 (Promega.) Fidelity of the product was verified by DNA sequence analysis according standard procedures and is identical to the published TNFα receptor sequence (Gray et al., 1990, PNAS 87:7380–7384).

The extracellular domain of the TNFαR was PCR amplified from the rresulting PGEM-T clone using the following primers:

5' GGGCGTCGACAGATAGTGTGTGTCCCCAAGG 3' (SEQ ID NO:43; SalI site 5' end) and

5' CGCGGATCCTCATGTGGTGCCTGAGTCCTCAG 3' (SEQ ID NO:44; BamHI 5' end) and standard PCR amplification techniques.

The defective LP19 GCN4 leucine zipper domain was excised from plasmid pCCZ1-lp19 (see Section 9.1, above) by digestion with SalI and BamHI, and replaced with the SalI and BamHI piece produced by digesting the PCR fragment of the TNFαR domain employing standard molecular biology techniques (Sambrook et al., supra). The DNA sequence of the TNFαR-containing CadC-fusion polypeptide coding region in the resulting plasmid (pCCT, FIG. 9A) was determined to confirm integrity of the construction.

The plasmid pCCT was transformed into E2088 (see Section 5.3) and 4 independent isolates were assayed (together with clones derived from control plasmids pCCZ1-wt and pCCZ-lp19) according to the procedures described in Section 9.2, above. The results shown in FIG. 9B demonstrate that the CadC-fusion polypeptide comprising a TNFα receptor protein-protein interaction domain supported robust CadC-fusion polypeptide interaction-dependent activation of transcription from cadBA regulatory sequences.

Figure 9B:
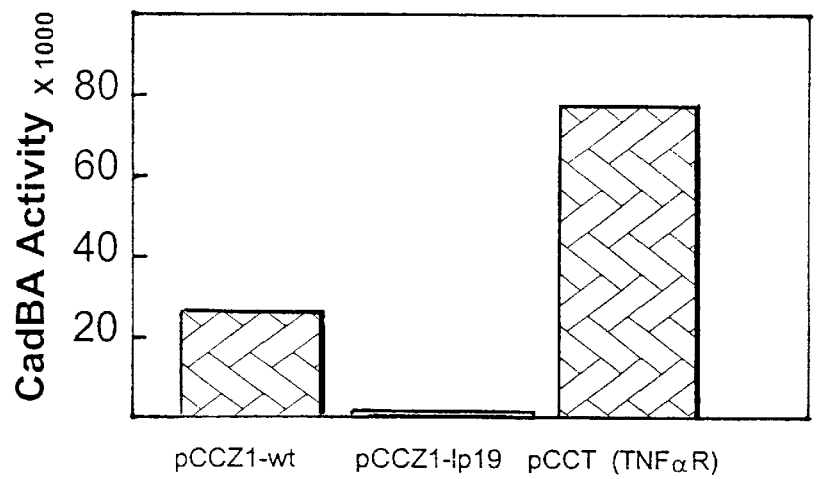
Figure 9C:
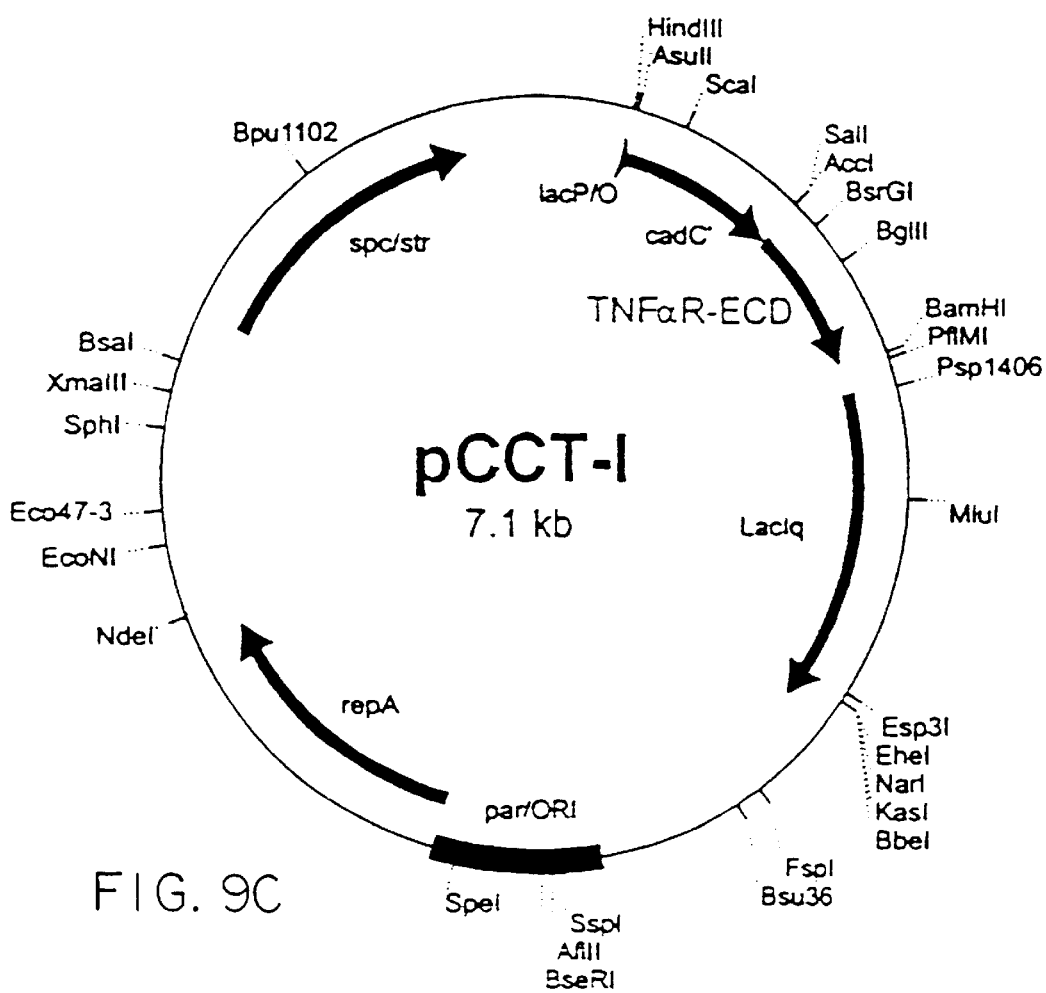

In order to produce a sequence encoding a CadC-fusion polypeptide whose expression is tightly regulated, the coding and associated control region of the CadC-fusion polypeptide described above were recloned from the plasmid PCCT into the plasmid pMS421 as described for pCCE-I above in Section 10. A map of the resulting plasmid, pCCT-I, is shown in FIG. 9C.

The plasmid pCCT-I was transformed into SMT0001 (see Section 10, above) and two isolated colonies were purified and inoculated into the well of a microtiter plate containing 200 µl of Luria Broth with 25 µl/ml spectinomycin. Growth was continued at 37° C. without shaking until all the wells became turbid (about 3 hours).

Figure 9D:
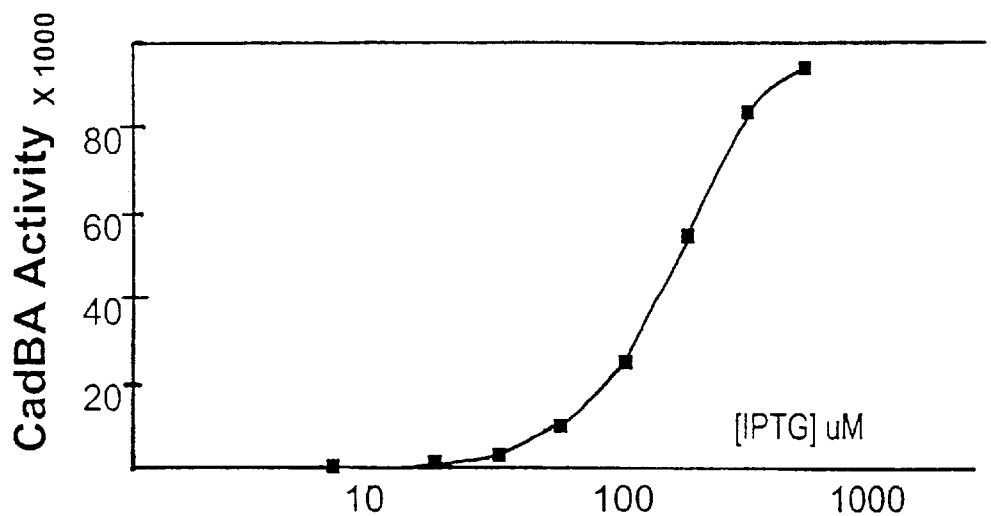
Figure 9E:
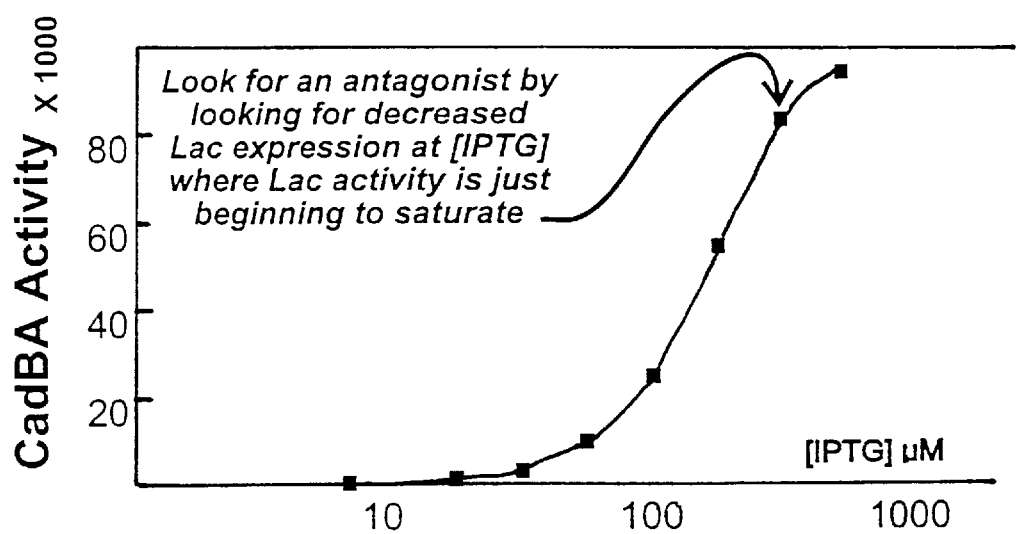

For induction of CadC-fusion polypeptide expression, 15 µl of the above cells were inoculated into 200 µl of Luria Broth with 25 µl/ml spectinomycin and various concentrations of IPTG (in separate wells) at the concentration values indicated in FIG. 9D. The microtiter plate was then incubated for 5 hours at 37° C. and β-galactosidase assays were performed as described in Section 9.2. The results in FIG. 9D show the averages of the results obtained with two isolated colonies plotted against the IPTG concentration employed during the second growth interval. Increasing the IPTG concentration, and therefore the level of the TNFαR CadC-fusion polypeptide produced, yielded increasing levels of cadBA transcription (monitored by the Lac reporter gene). This ability to control levels of CadC-fusion polypeptides is beneficial to performance of the methods of the invention. FIG. 9E depicts the strategy utilized for choosing an appropriate IPTG concentration for performing an antagonist screen. By choosing an appropriate level of IPTG to perform a sensitive antagonist screen, it was possible to use the strain to detect compounds that specifically decreased expression of cadBA-lac.

13. EXAMPLE

The Autocrine CadC-based Systems: Co-Expressing Ligands with CadC-Fusion Polypeptides The Example presented herein describes the successful construction and characterization of an autocrine CadC-based cell system. Such an autocrine system or autocrine ligand system comprises a CadC-based cell system wherein the CadC-fusion polypeptide is co-expressed together with modulators, e.g., ligands, or potential modulators of CadC-fusion polypeptide activity. The strategy developed herein thereby allows one to, for exmple, select for agonists and/or antagonists and/or utilize modulators of CadC-fusion polypeptide activity.

Access to the periplasmic space of $E. coli$ is restricted by the presence of the $E. coli$ outer membrane, which excludes most molecules larger that 1000 daltons (Todt et al., 1992, Biochemistry 31:10471–10478). This outer membrane may prevent externally applied molecular ligands from ever reaching the extra-cellular domain of a CadC-fusion polypeptide. Therefore, it was desirable to develop a strategy to express such molecules autologously from within a CadC-based cell system. This Example describes the construction of such autocrine ligand systems and specifically tests them using three known receptor/ligand pairs: the insulin receptor/insulin, the TNFα-receptor/TNFα, and the erythropoietin receptor/Epo. As described herein, each of these autologously expressed ligands was able to specifically activate its own cognate CadC-receptor fusion polypeptide.

13.1 Construction of a CadC-based Autocrine Ligand System

A primary consideration in designing such autocrine systems was the compatibility of the ligand-expression plasmid with the CadC-fusion polypeptide expression plasmid, since the two plasmids must reside in the same cell. As constructed herein, the CadC-fusion polypeptides were expressed under the control of LacZ on a plasmid with a pSC101 origin of replication and a spectinomycin-selectable marker, while the ligand-expression plasmid was designed to express ligands under the control of AraC on a plasmid with a colE1 origin and an ampicillin-selectable marker.

Construction of the ligand-expression plasmid began with a plasmid construct called pBAD18 (Guzman, L.-M. et al, 1995, J. Bacteriol. 177:4121–4130). The pBAD18 plasmid was designed to allow arabinose-inducible expression of proteins in $E. coli$.

The plasmid was then modified into the cloning vehicle pBADa, which was designed to direct the localization of ligands or potential ligands to the membrane compartment. Secreted proteins require leader "signal" sequences to target them to the periplasm (MacIntyre et al., 1990, Mol. Gen. Genet. 221:466–474), with a preferred leader sequence being one derived from the OmpA protein (Hobom et al., 1995, Dev. Biol. Stand. 84:255–262).

The cloning vehicle pBADa (FIG. 10A) was constructed as follows: The OmpA signal sequence was PCR amplified from pASK75 (Skerra A., 1994, Gene 151:131–135) using the following primers:

5' CGGAATTCAGATAACGAGGGCAAAAAATG 3'(SEQ ID NO:45; EcoRI site at 5' end), and

5' GCTCTAGAGGCCTGCGCTACGGTAGCG 3' (SEQ ID NO:46; XbaI site at 5' end) and standard PCR amplification techniques.

This PCR product and the plasmid PBAD18 were digested with EcoRI and XbaI, fragments gel purified and ligated, and correct pBADa clones were verified using standard molecular biology procedures (Sambrook et al., supra; Ausubel et al., supra). The resulting pBADa can be used to express any desired peptide sequence in a manner which targets the expresed peptide to the cell's periplasmic space. Use of the pBADa plasmid to successfully produce three different examples of such targeted sequences (EPO, insulin and TNFα) is described below.

The periplasmic Epo expression vector, pASE (FIG. 10A), was constructed in two steps. First, to obtain the Epo sequences, appropriate PCR primers, 5' CGCGGAGATGGGGGTGCACGAAT 3' (SEQ ID NO:47) and 5' GCTGAGCTGAGAGCCCCTCGACGG 3' (SEQ ID NO:48), and standard PCR amplification techniques were used to amplify Epo from a human placenta Marathon-ready cDNA library (Clontech) using the Advantage-HF PCR kit (Clontech) according to the vendor's recommendations. These PCR fragments were cloned into the pGEM-T vector and transformed into the host strain JM109 (Promega). The product was verified by DNA sequence analysis according standard procedures and proved to be identical with published sequence (Lin et al. 1985, PNAS 82:7580–7584).

Next, the Epo sequences were PCR amplified from the above pGEM-T clone using the following PCR primers:

5' GCTCTAGACTTCTCCTGTCCCTGCTGTC 3' (SEQ ID NO:49; XbaI site at 5' end), and

5' GCCCAAGCTTGCCCAGGTGGACACACCTG 3' (SEQ ID NO:50; HindIII site at 5' end) and standard PCR amplification techniques.

This PCR product and plasmid pBADa were digested with XbaI and HindIII, fragments were gel purified and ligated to generate pASE according to standard procedures (Sambrook et al., supra).

To obtain the insulin sequences, appropriate PCR primers,

5' CCTTTGTGAACCAACACCTGTGCGGC 3' (SEQ ID NO:51) and 5' GGCTGCCTGCAGGCTGCGTCTAGT 3' (SEQ ID NO:52), were used to amplify insulin from a human placenta Marathon-ready cNDA library (Clontech) using the Advantage-HF PCR kit (Clontech) according to the vendor's recommendations. The PCR fragments were cloned into the pGEM-T vector and transformed into the host strain JM109 (Promega). The product was verified by DNA sequence analysis according standard procedures and was identical with published sequence (Bell et al., 1980, Nature 284:26–32).

To create the periplasmic insulin expression clone, pASI (FIG. 10A) the insulin sequences were PCR amplified (from the above pGEM-T clone) using the following PCR primers:

5' GCTCTAGATTTGTGAACCAACACCTGTCGGC 3' (SEQ ID NO:53; XbaI site at 5' end), and

5' GCCCAAGCTTGCTGCCTGCAGGCTGCGTCTAG 3' (SEQ ID NO:54; HindIII site at 5' end) and standard PCR amplification techniques.

This PCR product and plasmid pBADa were digested with XbaI and HindIII, fragments were gel purified and ligated to generate pASI according to standard procedures (Sambrook et al., supra; Ausubel et al., supra).

To obtain the TNFα sequences, appropriate PCR primers,

5' TCTCCCCTGGAAAGGACACCATGAGC 3' (SEQ ID NO:55) and

5' GGCGTTTGGGAAGGTTGGATGTTCG 3' (SEQ ID NO:56), and standard PCR amplification techniques were used to amplify TNFα from a human placenta Marathon-ready cDNA library (Clontech) using the Advantage-HF PCR kit (Clontech) according to the vendor's recommendations. The PCR fragments were cloned into the pGEM-T vector and transformed into the host strain JM109 (Promega). The product was verified by DNA sequence analysis according standard procedures and was identical with published sequence (Marmenout et al., 1985, Eur. J. Biochem. 152:515–522).

To create the periplasmic TNFα expression clone, pAST (FIG. 10A) the TNFα sequences were PCR amplified (from the above clone) using the following PCR primers:

5' GCTCTAGAGAAGAGTTCCCCACGGAC-CTCTCTC 3' (SEQ ID NO:57; XbaI site at 5' end), and 5' CGTTTGGGAAGCTTGGATGTTCG 3' (SEQ ID NO:1); HindIII site at 5' end) and standard PCR amplification techniques.

This PCR product and the plasmid pBADa were digested with XbaI and HindIII, fragments were gel purified and ligated to generate pAST according to standard procedures (Sambrook et al., supra).

Figure 10B:
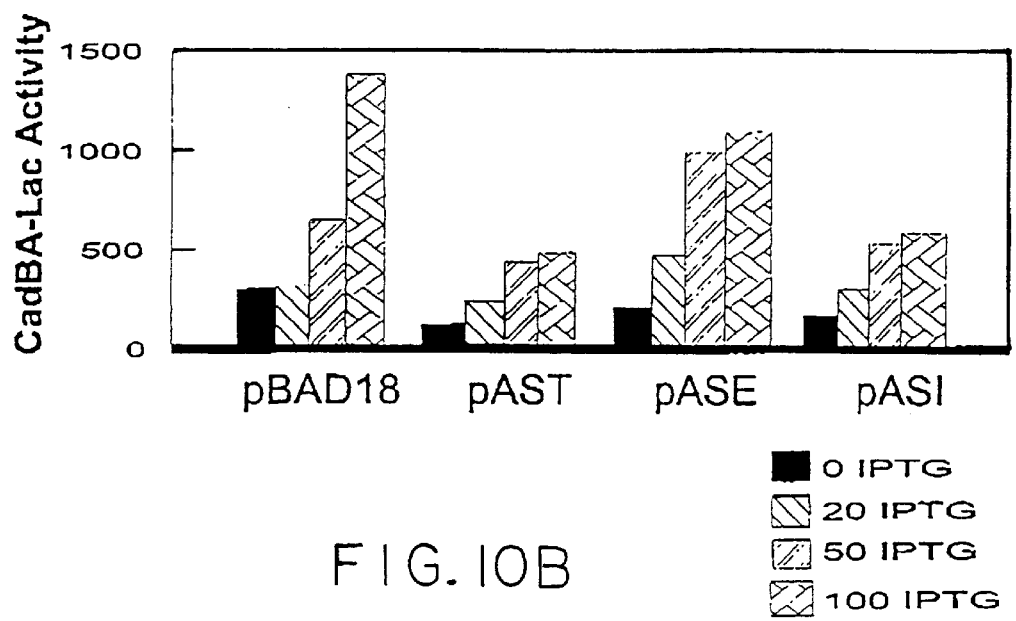
FIG. 10B shows the expression of the CadBA-Lac fusion by CadC-EpoR and various co-expressed ligands. Epo is shown to specifically induce expression via the CadC-EpoR fusion polypeptide.

13.2 Ligand-induced specific modulation of CadC-Fusion Polypeptide Activity in CadC-based Autocrine System To examine the specificity and co-expression of CadC-EpoR(ECD) and Epo, the plasmids pBAD18, pASE, pASI, and pAST were each introduced by transformation into the strain E2088 (see Section 5.3), together with the inducible CadC-EpoR(ECD) (pCCE-I, FIG. 7C), and selection on ampicillin (100 μg/ml) and spectinomycin (25 μg/ml) Luria Broth agar plates. Each of the four resulting strains were grown overnight in liquid Luria Broth (LB) with 100 μg/ml ampicillin and 25 μg/ml spectinomycin, and then diluted 1:40 into the same media supplemented with arabinose (20 μM) and various IPTG concentrations (0, 20, 50 100 μM). Growth was continued at 37° C. for 7 hours and β-galactosidase activity was measured as described in Section 9.2. Plotted in FIG. 10B are specific activities (normalized to cell number) of the four strains grown with increasing concentrations of IPTG (0, 20, 50 100 μM IPTG), thereby inducing CadC-EpoR(ECD) expression.

Figure 10C:
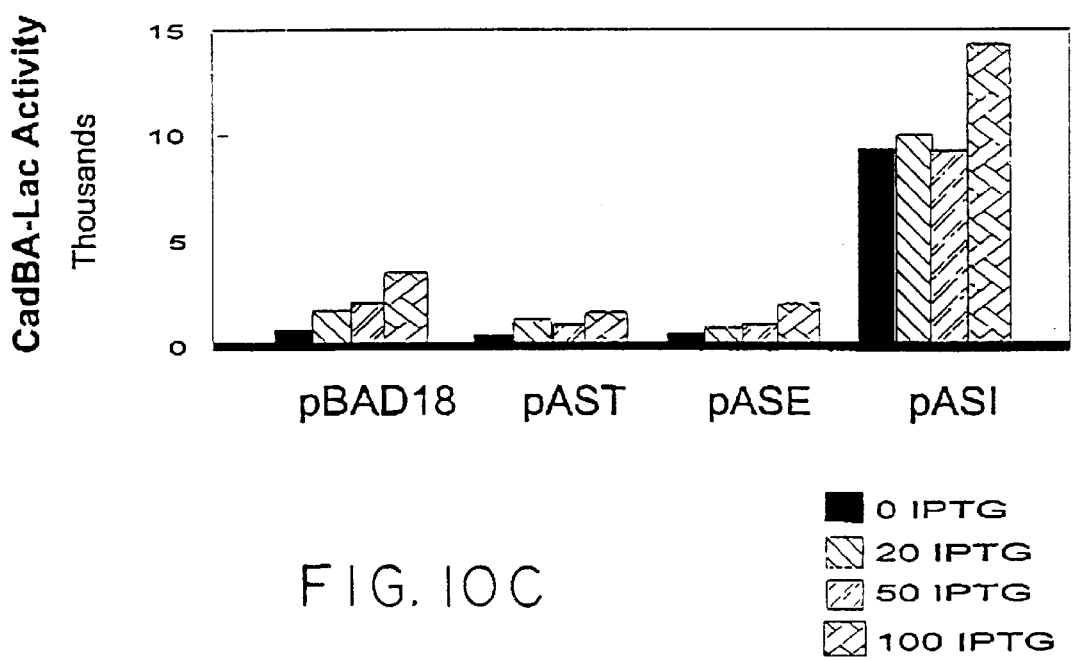
FIG. 10C shows the expression of the CadBA-Lac fusion by CadC-InsulinR and various co-expressed ligands. insulin is shown to specifically induce expression via the CadC-InsR fusion polypeptide.

Co-expression of the EPO cytokine with the CadC-EpoR (ECD) resulted in an approximately 2-fold increase in LacZ activity at all levels of induction, relative to the control cytokines, insulin and TNFα. The control plasmids, pASI and pAST, result in a reduction of LacZ activity, and hence CadC activator function, relative to the base vector pBAD18, which expresses only the CadC-EpoR(ECD) fusion polypeptide. A similar reduction was detected with the CadC-InsulinR(αECD) when non-cognate ligands are expressed (FIG. 9C). Although it is not clear why expression of a second protein reduces LacZ activity, perhaps it reduces the expression level of the original CadC-EpoR(ECD) or otherwise alters the environment of the periplasm. The magnitude of the reduction was similar for both non-cognate ligands relative to the control pBAD18 plasmid in experiments with CadC-EpoR(ECD) and CadC-InsulinR(αECD; FIGS. 10B and 10C, respectively).

To study specificity and the effects of insulin co-expression on CadC-InsulinR(αECD), pCCI-I [inducible CadC-InsulinR (αECD), FIG. 8C] was introduced together with either pBAD18, PASE, pASI, or pAST into the strain E2088 (see Section 5.3) by transformation and selection on ampicillin (100 μg/ml) and spectinomycin (25 μg/ml) LB agar. Individual colonies from the resulting strains were grown overnight in LB with 100 μg/ml ampicillin and 25 μg/ml spectinomycin, and diluted 1:40 into the same media supplemented with arabinose (40 μM) and various IPTG concentrations (see below). Growth was continued at 21° C. for 12 hours and β-galactosidase activity was measured as described in Section 9.2.

Plotted in FIG. 10C are specific activities (normalized to cell number) of the four strains grown with various IPTG concentrations (0, 20, 50 100 μM) to induce CadC-InsulinR (αECD) expression. Co-expression of the insulin cytokine produced an 8 to 20 fold increase in LacZ activity (depending on the level of CadC-InsulinR(αECD) expression) relative to the control cytokines, Epo and TNFα. The control plasmids, PASE and pAST, reduce CadC activator function relative to the base vector pBAD18, which expresses no foreign periplasmic protein, in addition to the CadC-InsulinR(αECD) chimera, similar to the effects noted in FIG. 10B for CadC-EpoR(ECD) with pASI and pAST. As discussed above, conditions of co-expression with non-cognate ligands probably represents the correct control, although the robust insulin stimulation seen in this experiment allowed the clear demonstration of appropriate ligand stimulation regardless of the control chosen.

To examine the effects of TNFα expression on the CadC-TNFα(ECD), the plasmids pBAD18, pASE, pASI, and pAST were each introduced together with pCCT-I [inducible CadC-TFαR(ECD), FIG. 9C] into the strain E2088 (see Section 5.3) by and selection for ampicillin (100 μg/ml) and spectinomycin (25 μg/ml) on LB agar. Preliminary experiments suggested the behavior of the CadC-TNFαR(ECD) was more complex than that of the EpoR and insulinR constructs and that it would be necessary to examine ligand interactions under conditions of both basal (uninduced) and induced expression of the co-expressed ligand. Cultures of these 4 strains were grown from single colonies for 5 hours in liquid Luria Broth with 100 μg/ml ampicillin and 25 μg/ml spectinomycin, and then diluted 1:10 into the same media with four concentrations of IPTG (receptor induction) and arabinose (ligand induction): 0 IPTG, 20 μM ara; 20 μM IPTG, 20 μM ara; 0 IPTG, 0 ara; 20 μM IPTG, 0 ara. Growth was continued at 37° C. for 3.5 hours and β-galactosidase activity was assayed as described in Section 9.2.

Figure 10D:
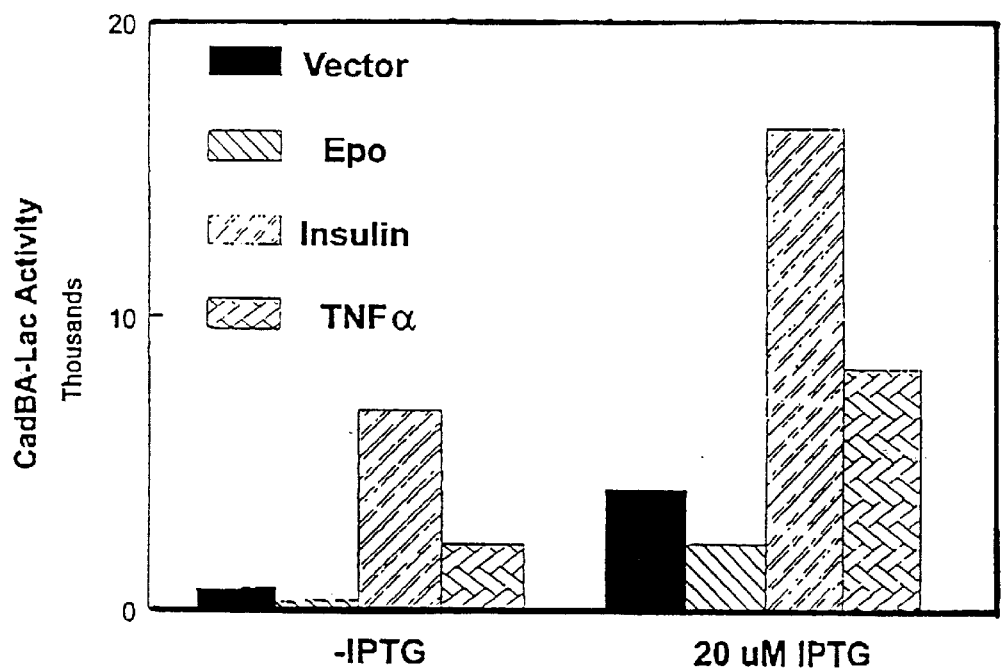
FIGS. 10D–10E shows the expression of the CadBA-Lac fusion by CadC-TNF-aR and various co-expressed ligands.
Figure 10E:
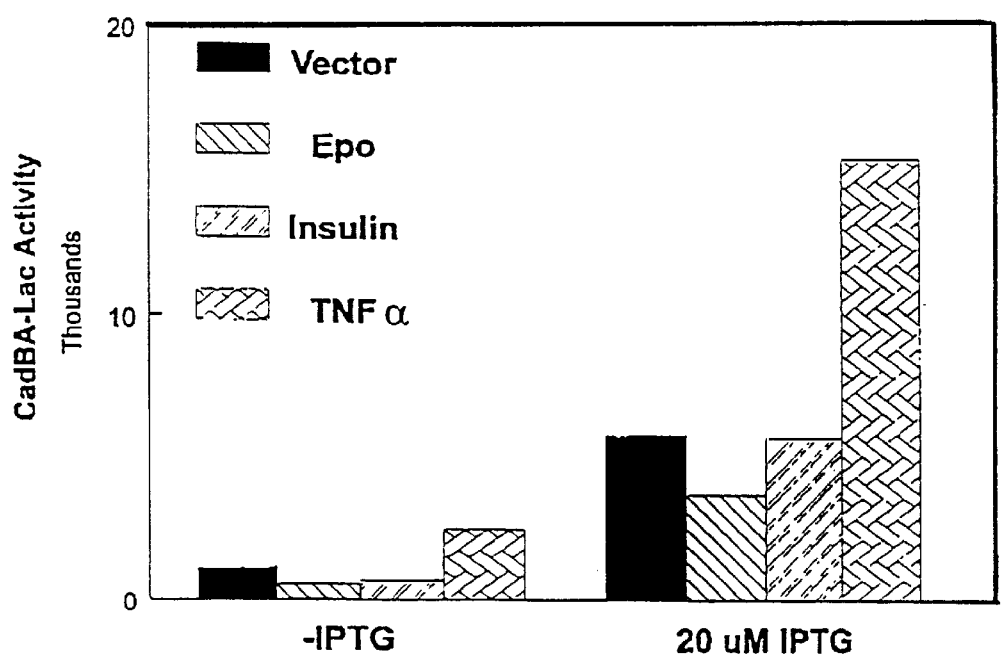

FIGS. 10D–10E shows the specific activities of the four strains grown with the four combinations of inducers normalized to cell number. With the CadC-TNFαR(ECD) receptor, stimulation with both insulin and TNFα is seen, where stimulation with insulin is greater than that detected with the cognate TNFα ligand. The Epo ligand fails to stimulate. When lower levels (basal, uninduced; FIG. 10E) of ligand co-expression are examined, the situation is more clear. Under these conditions, only the cognate ligand (TNFα) stimulates the CadC-TNFαR(ECD) construct.

The Example presented herein clearly demonstrates appropriate receptor stimulation for each of the three ligand-receptor pairs tested. In particular, no case was CadC-EpoR (ECD) stimulated by insulin or TNFα, and other conditions either showed comparable, reduced or no stimulation by Epo. Similarly, under no conditions was CadC-InsulinR (αECD) stimulated by either Epo or TNFα, and insulin stimulation was either comparable, reduced or not seen. For CadC-TNFαR(ECD), other assay conditions either showed TNFα, insulin, or TNFα and insulin stimulation, but in no instance was Epo stimulation noted. The observation of unique TNFα stimulation with low level (uninduced) ligand expression clearly demonstrates specificity for the TNFα/CadC-TNFα(ECD) pair.

The autocrine ligand expression system described herein will have many novel applications. For example, the ability to measure the activation of a receptor by co-expressing its cognate ligand can be applied to the field of qenomic analysis. With the human genome sequencing effort many laboratories are rapidly accumulating collections of cDNA clones, some members of which are believed to be secreted or membrane associated proteins. Among such collections will be receptors and their ligands. An important step in the assignment of function to cDNAs and their genes will be the assignment of ligands to their receptors. CadC-fusion polypeptides can be co-transformed together with a collection of candidate secreted proteins in the autocrine ligand expression system of the invention. Appropriate ligand-receptor-pairs can be identified by the ability of the ligand to stimulate cadBA reporter expression.

Experimental results presented herein verify the usefulness the CadC-based autologous cell systems of the invention exhibit for performing such analyses. In particular, CadC-TNFαR(ECD) plasmids were cotransformed together with a mixed collection of ligand constructs (insulin, Epo, TNFα, and vector alone; see FIG. 10A) according to the following general scheme. Cells were transformed with spectinomycin-resistant plasmids that expressed the CadC-fusion polypeptides together with ampicillin-resistant "ligand mixture"-expressing plasmids. Transformed cells were plated on LB agar containing ampicillin and spectinomycin. Colonies that grew in the presence of both drugs were purified and tested under a variety of conditions (+/−IPTG; +/−Ara).

A total of 96 transformants were assayed under (−IPTG, −Ara conditions. Seven of these transformants stood out as having clearly elevated levels of LacZ activity. Analysis of the resident plasmids in these strains showed that these isolates all contained the TNFα—expressing construct.

In a second similar reconstruction experiment it was possible to demonstrate successful selection of an insulin ligand-expressing plasmid from the same insulin, Epo, TNFα, and vector alone mixture. Thus, it is possible to successfully use the autocrine system described herein to select the correct ligand from such a mixture. Large scale receptor-ligand matching experiments are feasible with automation and scale-up of these experiments for genomic research.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A CadC-fusion polypeptide comprising: a periplasmic domain, a transmembrane domain and an *E. coli* CadC transcriptional regulatory domain.

2. The CadC-fusion polypeptide of claim 1, wherein the periplasmic domain is a protein-protein interaction domain.

3. The CadC-fusion polypeptide of claim 2, wherein the protein-protein interaction domain comprises an erythropoietin receptor dimerization domain, an insulin receptor dimerization domain or a tumor necrosis factor α receptor interaction domain.

4. The CadC-fusion polypeptide of claim 3, wherein the erythropoietin receptor dimerization domain is as depicted in FIG. 7A (SEQ ID NO:4), the insulin receptor dimerization domain is as depicted in FIG. 8A (SEQ ID NO:5) or the tumor necrosis factor a receptor interaction domain is as depicted in FIG. 9A (SEQ ID NO:6).

5. The CadC-fusion polypeptide of claim 2, wherein the protein-protein interaction domain comprises a β3 adrenergic receptor.

6. The CadC-fusion polypeptide of claim 2, wherein the protein-protein interaction domain comprises a KIT stem cell factor receptor, granulocyte-colony stimulating factor receptor, nerve growth factor receptor, insulin-like growth factor receptor, somatotropin receptor, IL1 receptor, glial-derived neurotrophic factor receptor, gp39 receptor, a Her2 receptor or a β3 adrenergic receptor.

7. The CadC-fusion polypeptide of claim 1, wherein the CadC transcriptional regulatory domain comprises the CadC cytoplasmic domain depicted in FIG. 2 (SEQ ID NO:1).

8. The CadC-fusion polypeptide of claim 1, wherein the transmembrane domain is a CadC transmembrane domain.

9. The CadC-fusion polypeptide of claim 8, wherein the CadC transmembrane domain is the CadC transmembrane domain depicted in FIG. 2 (SEQ ID NO:1).

10. The CadC-fusion polypeptide of claim 1, wherein the periplasmic domain is a test domain.

11. An isolated nucleic acid encoding a CadC-fusion polypeptide, said CadC-fusion polypeptide comprising a periplasmic domain, a transmembrane domain and an *E. coli* CadC transcriptional regulatory domain.

12. The isolated nucleic acid of claim 11 wherein the periplasmic domain comprises an erythropoietin receptor dimerization domain, an insulin receptor dimerization domain or a tumor necrosis factor α receptor interaction domain.

13. The nucleic acid of claim 11, further comprising an inducible nucleotide regulatory sequence which controls inducible expression of the nucleic acid in a host cell.

14. A CadC-fusion polypeptide library comprising a plurality of nucleic acids encoding CadC-fusion polypeptides, said CadC-fusion polypeptide comprising a periplasmic domain, a transmembrane domain and an *E. coli* CadC transcriptional regulatory domain, wherein at least two of the nucleic acids encode CadC-fusion polypeptides comprising different periplasmic domains.

15. A CadC-based cell system comprising an Enterobacteriaceae cell comprising: (a) a nucleic acid encoding a CadC-fusion polypeptide, wherein the CadC-fusion polypeptide comprises a periplasmic domain, a transmembrane domain and an *E. coli* CadC transcriptional regulatory domain, and (b) a cadBA reporter construct nucleic acid, wherein the cadBA reporter construct nucleic acid comprises a cadBA regulatory nucleotide sequence operatively linked to a reporter nucleotide sequence encoding a detectable gene product, and wherein the cell lacks a functional endogenous cadC gene.

16. The cell system of claim 15, wherein the cell is an *E. coli* cell or an *S. typhimurium* cell.

17. The cell system of claim 15 genetically engineered to further comprise a nucleic acid which encodes a peptide such that the expressed peptide is targeted to the periplasmic space of the cell system.

18. A CadC-fusion polypeptide library comprising a plurality of Enterobacteriaceae cells lacking a functional endogenous cadC gene, said cells comprising:
   a) a nucleic acid encoding a CadC-fusion polypeptide that comprises a periplasmic domain, a transmembrane domain and an *E. coli* CadC transcriptional regulatory domain, and
   b) a cadBA reporter construct nucleic acid comprising a cadBA regulatory nucleotide sequence operatively linked to a reporter nucleotide sequence encoding a detectable gene product,
wherein at least two of the cells encode CadC-fusion polypeptides comprising different periplasmic domains.

19. A method for identifying a candidate protein-protein interaction domain, comprising:
   a) culturing a cell system comprising an Enterobacteriaceae cell lacking a functional endogenous cadC gene, said cell comprising:
      (i) a nucleic acid encoding a CadC-fusion polypeptide that comprises a periplasmic test domain, a transmembrane domain and an *E. coli* CadC transcriptional regulatory domain, and
      (ii) a cadBA reporter construct nucleic acid comprising a cadBA regulatory nucleotide sequence operatively linked to a reporter nucleotide sequence encoding a detectable gene product,
      under conditions whereby the CadC-fusion polypeptide is expressed, and
   b) assaying for reporter nucleotide sequence expression, such that if a level of reporter nucleotide sequence expression above background is detected, a candidate protein-protein interaction domain is identified.

20. The method of claim 19, wherein the Enterobacteriaceae cell is an *E. coli* cell or an *S. typhimurium* cell.

21. A method for identifying a candidate polypeptide partner, comprising:
   a) culturing a cell system comprising an Enterobacteriaceae cell lacking a functional endogenous cadC gene, said cell comprising:
      (i) a nucleic acid encoding a first CadC-fusion polypeptide which comprises a periplasmic domain comprising a protein-protein interaction domain which does not self-dimerize, a transmembrane domain and an *E. coli* CadC transcriptional regulatory domain,
      (ii) a cadBA reporter construct nucleic acid comprising a cadBA regulatory nucleotide sequence operatively linked to a reporter nucleotide sequence encoding a detectable gene product, and
      (iii) a second nucleic acid encoding a CadC-fusion polypeptide the periplasmic domain of which is a test domain,
      under conditions whereby the CadC-fusion polypeptides are coexpressed; and
   b) assaying for reporter nucleotide sequence expression, such that if a level of reporter nucleotide sequence expression above background is detected, a candidate polypeptide partner is identified.

22. The method of claim 21, further comprising expressing the second CadC fusion polypeptide in a CadC-based cell system comprising a nucleic acid encoding a control CadC-fusion polypeptide under conditions whereby the control and the second CadC-fusion polypeptides are coexpressed, and assaying for cadBA reporter nucleotide sequence expression, such that if the level of reporter nucleotide sequence expression assayed in the presence of the second CadC-fusion polypeptide is no greater than in its presence, the specificity of the candidate polypeptide partner is supported.

23. The method of claim 22, wherein the Enterobacteriaceae cell is an *E. coli* cell or an *S. typhimurium* cell.

24. The method of claim 21, wherein the Enterobacteriaceae cell is an *E. coli* cell or an *S. typhimurium* cell.

25. A method for identifying a candidate ligand, comprising:
   a) culturing a cell system comprising an Enterobacteriaceae cell lacking a functional endogenous cadC gene, said cell comprising:
      (i) a first nucleic acid encoding a peptide such that the expressed peptide is targeted to the periplasmic space of the cell system;
      (ii) a second nucleic acid encoding a CadC-fusion polypeptide that comprises a periplasmic domain which comprises a protein-protein interaction domain for which a ligand is sought, and wherein the peptide is a candidate ligand, a transmembrane domain and an *E. coli* CadC transcriptional regulatory domain, and
      (ii) a cadBA reporter construct nucleic acid comprising a cadBA regulatory nucleotide sequence operatively linked to a reporter nucleotide sequence encoding a detectable gene product,
      under conditions whereby the CadC-fusion polypeptide is expressed at a level which allows detection of ligand-enhanced protein-protein domain interaction, and the peptide is coexpressed; and
   b) assaying for reporter nucleotide sequence expression, such that if a higher level of reporter nucleotide sequence expression is detected in the presence of the peptide than in its absence, a candidate ligand is identified.

26. The method of claim 25, further comprising coexpressing the peptide in a CadC-based cell system with a control CadC-fusion polypeptide under conditions whereby ligand-enhanced interaction of the protein-protein interaction domain can be detected, and assaying for cadBA reporter nucleotide sequence expression, such that if the level of reporter nucleotide sequence expression assayed in the absence of peptide is no greater than in its presence, the specificity of the candidate ligand is supported.

27. The method of claim 26, wherein the Enterobacteriaceae cell is an *E. coli* cell or an *S. typhimurium* cell.

28. The method of claim 25, wherein the Enterobacteriaceae cell is an *E. coli* cell or an *S. typhimurium* cell.

29. A method for identifying a compound which modulates a specific protein-protein interaction, comprising:
   a) contacting a first cell system with a test substance, said first cell system comprising a first Enterobacteriaceae cell lacking a functional endogenous cadC gene, said first cell comprising:
      (i) a nucleic acid encoding a CadC-fusion polypeptide that comprises a periplasmic domain which comprises a protein-protein interaction domain involved in the specific protein-protein interaction, a transmembrane domain and an *E. coli* CadC transcriptional regulatory domain, and (ii) a cadBA reporter construct nucleic acid comprising a cadBA regulatory nucleotide sequence operatively linked to a reporter nucleotide sequence encoding a detectable gene product;

b) contacting a second cell system with the test substance, said second cell system comprising a second Enterobacteriaceae cell lacking a functional endogenous cadC gene, said second cell comprising:
(iii) a nucleic acid encoding a control CadC-fusion polypeptide, a transmembrane domain and a CadC transcriptional regulatory domain, and
(iv) a cadBA reporter construct nucleic acid comprising a cadBA regulatory nucleotide sequence operatively linked to a reporter nucleotide sequence encoding a detectable gene product, c) assaying for reporter nucleotide sequence expression, such that, if, in (a) a differential level of reporter nucleotide sequence expression is assayed in the presence and absence of the test substance, and this differential is larger than any differential assayed in (b) in the presence and absence of the test compound, a compound which modulates a specific protein-protein interaction is identified.

30. The method of claim 29, wherein a higher level of reporter nucleotide sequence expression is assayed in (a) in the presence of test compound than in its absence, such that the test compound identified is a candidate agonist of the specific protein-protein interaction.

31. The method of claim 29, wherein a lower level of reporter nucleotide sequence expression is assayed in (a) in the presence of test compound than in its absence, such that the test compound identified is a candidate antagonist of the specific protein-protein interaction.

32. The method of claim 29, wherein the Enterobacteriaceae cell is an *E. coli* cell or an *S. typhimurium* cell.

33. A method for identifying a compound which modulates a specific protein-protein interaction, comprising:
a) contacting a first cell system with a test substance, said first cell system comprising a first Enterobacteriaceae cell lacking a functional endogenous cadC gene, said first cell comprising:
(i) a first nucleic acid encoding a peptide such that the expressed peptide is targeted to the periplasmic space of the first cell system;
(ii) a second nucleic acid encoding a CadC-fusion polypeptide that comprises a periplasmic domain comprising a protein-protein interaction domain involved in the specific protein-protein interaction, a transmembrane domain and an *E. coli* CadC transcriptional regulatory domain, and
(ii) a cadBA reporter construct nucleic acid comprising a cadBA regulatory nucleotide sequence operatively linked to a reporter nucleotide sequence encoding a detectable gene product;

b) contacting a second cell system with the test substance, said second cell system comprising an Enterobacteriaceae cell lacking a functional endogenous cadC gene, said cell comprising:
(iv) a first nucleic acid encoding a peptide such that the expressed peptide is targeted to the periplasmic space of the cell system;
(vi) a second nucleic acid encoding a control CadC-fusion polypeptide, a transmembrane domain and an *E. coli* CadC transcriptional regulatory domain, and
(viii) a cadBA reporter construct nucleic acid comprising a cadBA regulatory nucleotide sequence operatively linked to a reporter nucleotide sequence encoding a detectable gene product; and c) assaying for reporter nucleotide sequence expression, such that, if, in (a) a differential level of reporter nucleotide sequence expression is assayed in the presence and absence of the test substance, and this differential is larger than any differential assayed in (b) in the presence and absence of the test compound, a compound which modulates a specific protein-protein interaction is identified.

34. The method of claim 33, wherein a higher level of reporter nucleotide sequence expression is assayed in (a) in the presence of test compound than in its absence, such that the test compound identified is a candidate agonist of the specific protein-protein interaction.

35. The method of claim 33, wherein a lower level of reporter nucleotide sequence expression is assayed in (a) in the presence of test compound than in its absence, such that the test compound identified is a candidate antagonist of the specific protein-protein interaction.

36. The method of claim 33, wherein the Enterobacteriaceae cell is an *E. coli* cell or an *S. typhimurium* cell.

37. A CadC-fusion polypeptide comprising: a periplasmic domain, a transmembrane domain and a *S. typhimurium* CadC transcriptional regulatory domain.

38. The CadC-fusion polypeptide of claim 37, wherein the periplasmic domain is a protein-protein interaction domain.

39. The CadC-fusion polypeptide of claim 38, wherein the protein-protein interaction domain comprises an erythropoietin receptor dimerization domain, an insulin receptor dimerization domain or a tumor necrosis factor α receptor interaction domain.

40. The CadC-fusion polypeptide of claim 39, wherein the erythropoietin receptor dimerization domain is as depicted in FIG. 7A (SEQ ID NO:4), the insulin receptor dimerization domain is as depicted in FIG. 8A (SEQ ID NO:5) or the tumor necrosis factor α receptor interaction domain is as depicted in FIG. 9A (SEQ ID NO:6).

41. The CadC-fusion polypeptide of claim 37, wherein the transmembrane domain is a CadC transmembrane domain.

42. The CadC-fusion polypeptide of claim 37, wherein the periplasmic domain is a test domain.

43. An isolated nucleic acid encoding a CadC-fusion polypeptide, said CadC-fusion polypeptide comprising a periplasmic domain, a transmembrane domain and a *S. typhimurium* CadC transcriptional regulatory domain.

44. A CadC-fusion polypeptide library comprising a plurality of nucleic acids encoding CadC-fusion polypeptides, said CadC-fusion polypeptide comprising a periplasmic domain, a transmembrane domain and a *S. typhimurium* CadC transcriptional regulatory domain, wherein at least two of the nucleic acids encode CadC-fusion polypeptides comprising different periplasmic domains.

45. A CadC-based cell system comprising an Enterobacteriaceae cell comprising:
(a) a nucleic acid encoding a CadC-fusion polypeptide, wherein the CadC-fusion polypeptide comprises a periplasmic domain, a transmembrane domain and a *S. typhimurium* CadC transcriptional regulatory domain, and (b) a cadBA reporter construct nucleic acid, wherein the cadBA reporter construct nucleic acid comprises a cadBA regulatory nucleotide sequence operatively linked to a reporter nucleotide sequence encoding a detectable gene product, and wherein the cell lacks a functional endogenous cadC gene.

46. A CadC-fusion polypeptide library comprising a plurality of Enterobacteriaceae cells lacking a functional endogenous cadC gene, said cells comprising:
a) a nucleic acid encoding a CadC-fusion polypeptide that comprises a periplasmic domain, a transmembrane domain and *S. typhimurium* CadC transcriptional regulatory domain, and b) a cadBA reporter construct nucleic acid comprising a cadBA regulatory nucleotide sequence operatively linked to a reporter nucleotide sequence encoding a detectable gene product, wherein at least two of the cells encode CadC-fusion polypeptides comprising different periplasmic domains.

47. A method for identifying a candidate protein-protein interaction domain, comprising:
   a) culturing a cell system comprising an Enterobacteriaceae cell lacking a functional endogenous cadC gene, said cell comprising:
      (i) a nucleic acid encoding a CadC-fusion polypeptide that comprises a periplasmic test domain, a transmembrane domain and *S. typhimurium* CadC transcriptional regulatory domain, and
      (ii) a cadBA reporter construct nucleic acid comprising a cadBA regulatory nucleotide sequence operatively linked to a reporter nucleotide sequence encoding a detectable gene product, under conditions whereby the CadC-fusion polypeptide is expressed, and
   b) assaying for reporter nucleotide sequence expression, such that if a level of reporter nucleotide sequence expression above background is detected, a candidate protein-protein interaction domain is identified.

48. A method for identifying a candidate polypeptide partner, comprising:
   a) culturing a cell system comprising an Enterobacteriaceae cell lacking a functional endogenous cadC gene, said cell comprising:
      (i) a nucleic acid encoding a first CadC-fusion polypeptide which comprises a periplasmic domain comprising a protein-protein interaction domain which does not self-dimerize, a transmembrane domain and *S. typhimurium* CadC transcriptional regulatory domain,
      (ii) a cadBA reporter construct nucleic acid comprising a cadBA regulatory nucleotide sequence operatively linked to a reporter nucleotide sequence encoding a detectable gene product, and
      (iii) a second nucleic acid encoding a CadC-fusion polypeptide the periplasmic domain of which is a test domain,
      under conditions whereby the CadC-fusion polypeptides are coexpressed; and
   b) assaying for reporter nucleotide sequence expression, such that if a level of reporter nucleotide sequence expression above background is detected, a candidate polypeptide partner is identified.

49. A method for identifying a candidate ligand, comprising:
   a) culturing a cell system comprising an Enterobacteriaceae cell lacking a functional endogenous cadC gene, said cell comprising:
      (i) a first nucleic acid encoding a peptide such that the expressed peptide is targeted to the periplasmic space of the cell system;
      (ii) a second nucleic acid encoding a CadC-fusion polypeptide that comprises a periplasmic domain which comprises a protein-protein interaction domain for which a ligand is sought, and wherein the peptide is a candidate ligand, a transmembrane domain and a *S. typhimurium* CadC transcriptional regulatory domain, and
      (ii) a cadBA reporter construct nucleic acid comprising a cadBA regulatory nucleotide sequence operatively linked to a reporter nucleotide sequence encoding a detectable gene product,
      under conditions whereby the CadC-fusion polypeptide is expressed at a level which allows detection of ligand-enhanced protein-protein domain interaction, and the peptide is coexpressed; and
   b) assaying for reporter nucleotide sequence expression, such that if a higher level of reporter nucleotide sequence expression is detected in the presence of the peptide than in its absence, a candidate ligand is identified.

50. A method for identifying a compound which modulates a specific protein-protein interaction, comprising:
   a) contacting a first cell system with a test substance, said first cell system comprising a first Enterobacteriaceae cell lacking a functional endogenous cadC gene, said first cell comprising:
      (i) a nucleic acid encoding a CadC-fusion polypeptide that comprises a periplasmic domain which comprises a protein-protein interaction domain involved in the specific protein-protein interaction, a transmembrane domain and a *S. typhimurium* CadC transcriptional regulatory domain, and
      (ii) a cadBA reporter construct nucleic acid comprising a cadBA regulatory nucleotide sequence operatively linked to a reporter nucleotide sequence encoding a detectable gene product;
   b) contacting a second cell system with the test substance, said second cell system comprising a second Enterobacteriaceae cell lacking a functional endogenous cadC gene, said second cell comprising:
      (iii) a nucleic acid encoding a control CadC-fusion polypeptide, a transmembrane domain and a CadC transcriptional regulatory domain, and
      (iv) a cadBA reporter construct nucleic acid comprising a cadBA regulatory nucleotide sequence operatively linked to a reporter nucleotide sequence encoding a detectable gene product,
   c) assaying for reporter nucleotide sequence expression, such that, if, in (a) a differential level of reporter nucleotide sequence expression is assayed in the presence and absence of the test substance, and this differential is larger than any differential assayed in (b) in the presence and absence of the test compound, a compound which modulates a specific protein-protein interaction is identified.

51. A method for identifying a compound which modulates a specific protein-protein interaction, comprising:
   a) contacting a first cell system with a test substance, said first cell system comprising a first Enterobacteriaceae cell lacking a functional endogenous cadC gene, said first cell comprising:
      (i) a first nucleic acid encoding a peptide such that the expressed peptide is targeted to the periplasmic space of the first cell system;
      (ii) a second nucleic acid encoding a CadC-fusion polypeptide that comprises a periplasmic domain comprising a protein-protein interaction domain involved in the specific protein-protein interaction, a transmembrane domain and a *S. typhimurium* CadC transcriptional regulatory domain, and
      (ii) a cadBA reporter construct nucleic acid comprising a cadBA regulatory nucleotide sequence operatively linked to a reporter nucleotide sequence encoding a detectable gene product;
   b) contacting a second cell system with the test substance, said second cell system comprising an Enterobacteriaceae cell lacking a functional endogenous cadC gene, said cell comprising:

(iv) a first nucleic acid encoding a peptide such that the expressed peptide is targeted to the periplasmic space of the cell system;
(vi) a second nucleic acid encoding a control CadC-fusion polypeptide, a transmembrane domain and a *S. typhimurium* CadC transcriptional regulatory domain, and
(viii) a cadBA reporter construct nucleic acid comprising a cadBA regulatory nucleotide sequence operatively linked to a reporter nucleotide sequence encoding a detectable gene product; and c) assaying for reporter nucleotide sequence expression, such that, if, in (a) a differential level of reporter nucleotide sequence expression is assayed in the presence and absence of the test substance, and this differential is larger than any differential assayed in (b) in the presence and absence of the test compound, a compound which modulates a specific protein-protein interaction is identified.

* * * * *

UNITED STATES PATENT AND TRADEMARK OFFICE
CERTIFICATE OF CORRECTION

PATENT NO. : 6,265,174 B1
DATED : July 24, 2001
INVENTOR(S) : Menzel et al.

It is certified that error appears in the above-identified patent and that said Letters Patent is hereby corrected as shown below:

Title page,
Item [54], title please delete "[54] METHODS AND COMPOSITIONS FOR IDENTIFYING AND MODULATING CTIONPROTEIN-INTERACTIONS" and insert -- [54] METHODS AND COMPOSITIONS FOR IDENTIFYING AND MODULATING PROTEIN-PROTEIN INTERACTIONS--.

Signed and Sealed this

Tenth Day of December, 2002

JAMES E. ROGAN
*Director of the United States Patent and Trademark Office*

SEQUENCE LISTING

<160> NUMBER OF SEQ ID NOS: 57

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 1
cgtttgggaa gcttggatgt tcg        23

<210> SEQ ID NO 2
<211> LENGTH: 512
<212> TYPE: PRT
<213> ORGANISM: Escherichia coli

<400> SEQUENCE: 2

Met Gln Gln Pro Val Val Arg Val Gly Glu Trp Leu Val Thr Pro Ser
 1               5                  10                  15

Ile Asn Gln Ile Ser Arg Asn Gly Arg Gln Leu Thr Leu Glu Pro Arg
            20                  25                  30

Leu Ile Asp Leu Leu Val Phe Phe Ala Gln His Ser Gly Glu Val Leu
        35                  40                  45

Ser Arg Asp Glu Leu Ile Asp Asn Val Trp Lys Arg Ser Ile Val Thr
    50                  55                  60

Asn His Val Val Thr Gln Ser Ile Ser Glu Leu Arg Lys Ser Leu Lys

-continued

```
             65                  70                  75                  80
Asp Asn Asp Glu Asp Ser Pro Val Tyr Ile Ala Thr Val Pro Lys Arg
                    85                  90                  95
Gly Tyr Lys Leu Met Val Pro Val Ile Trp Tyr Ser Glu Glu Gly
                100                 105                 110
Glu Glu Ile Met Leu Ser Ser Pro Pro Ile Pro Glu Ala Val Pro
                115                 120                 125
Ala Thr Asp Ser Pro Ser His Ser Leu Asn Ile Gln Asn Thr Ala Thr
            130                 135                 140
Pro Pro Glu Gln Ser Pro Val Lys Ser Lys Arg Phe Thr Thr Phe Trp
145                 150                 155                 160
Val Trp Phe Phe Phe Leu Leu Ser Leu Gly Ile Cys Val Ala Leu Val
                165                 170                 175
Ala Phe Ser Ser Leu Asp Thr Arg Leu Pro Met Ser Lys Ser Arg Ile
                180                 185                 190
Leu Leu Asn Pro Arg Asp Ile Asp Ile Asn Met Val Asn Lys Ser Cys
            195                 200                 205
Asn Ser Trp Ser Ser Pro Tyr Gln Leu Ser Tyr Ala Ile Gly Val Gly
    210                 215                 220
Asp Leu Val Ala Thr Ser Leu Asn Thr Phe Ser Thr Phe Met Val His
225                 230                 235                 240
Asp Lys Ile Asn Tyr Asn Ile Asp Glu Pro Ser Ser Gly Lys Thr
                245                 250                 255
Leu Ser Ile Ala Phe Val Asn Gln Arg Gln Tyr Arg Ala Gln Gln Cys
                260                 265                 270
Phe Met Ser Ile Lys Leu Val Asp Asn Ala Asp Gly Ser Thr Met Leu
                275                 280                 285
Asp Lys Arg Tyr Val Ile Thr Asn Gly Asn Gln Leu Ala Ile Gln Asn
            290                 295                 300
Asp Leu Leu Glu Ser Leu Ser Lys Ala Leu Asn Gln Pro Trp Pro Gln
305                 310                 315                 320
Arg Met Gln Glu Thr Leu Gln Lys Ile Leu Pro His Arg Gly Ala Leu
                325                 330                 335
Leu Thr Asn Phe Tyr Gln Ala His Asp Tyr Leu Leu His Gly Asp Asp
                340                 345                 350
Lys Ser Leu Asn Arg Ala Ser Glu Leu Leu Gly Glu Ile Val Gln Ser
            355                 360                 365
Ser Pro Glu Phe Thr Tyr Ala Arg Ala Glu Lys Ala Leu Val Asp Ile
370                 375                 380
Val Arg His Ser Gln His Pro Leu Asp Glu Lys Gln Leu Ala Ala Leu
385                 390                 395                 400
Asn Thr Glu Ile Asp Asn Ile Val Thr Leu Pro Glu Leu Asn Asn Leu
                405                 410                 415
Ser Ile Ile Tyr Gln Ile Lys Ala Val Ser Ala Leu Val Lys Gly Lys
            420                 425                 430
Thr Asp Glu Ser Tyr Gln Ala Ile Asn Thr Gly Ile Asp Leu Glu Met
                435                 440                 445
Ser Trp Leu Asn Tyr Val Leu Leu Gly Lys Val Tyr Glu Met Lys Gly
            450                 455                 460
Met Asn Arg Glu Ala Ala Asp Ala Tyr Leu Thr Ala Phe Asn Leu Arg
465                 470                 475                 480
Pro Gly Ala Asn Thr Leu Tyr Trp Ile Glu Asn Gly Ile Phe Gln Thr
                485                 490                 495
```

Ser Val Pro Tyr Val Pro Tyr Leu Asp Lys Phe Leu Ala Ser Glu
        500                 505                 510

<210> SEQ ID NO 3
<211> LENGTH: 1064
<212> TYPE: DNA
<213> ORGANISM: Escherichia coli
<220> FEATURE:
<221> NAME/KEY: modified_base
<222> LOCATION: 58
<223> OTHER INFORMATION: n=a, c, g, or t
<220> FEATURE:
<221> NAME/KEY: modified_base
<222> LOCATION: 105
<223> OTHER INFORMATION: n=a, c, g, or t

<400> SEQUENCE: 3

| | | | | | |
|---|---|---|---|---|---|
| gtcaagtctg | ctttaattat | ttttaagcgt | gcataataag | ccctacacaa | attgggagna | 60 |
| tatatcatga | aaggctggct | ttttcttgtt | atcgcaatag | ttggngaagt | aatcgcaaca | 120 |
| tccgcattaa | aatctagcga | gggctttact | aagctcgcgt | tggccgattc | attaatgcag | 180 |
| ctggcacgac | aggtttcccg | actggaaagc | gggcagtgag | cgcaacgcaa | ttaatgtgag | 240 |
| ttagctcact | cattaggcac | cccaggcttt | acactttatg | cttccggctc | gtatgttgtg | 300 |
| tggaattgtg | agcggataac | aatttcacac | aggaaacagc | tatgaccatg | attacgccaa | 360 |
| gcttcattcc | cttttcgaat | gagtttctat | tatgcaacaa | cctgtagttc | gcgttggcga | 420 |
| atggcttgtt | actccgtcca | taaaccaaat | tagccgcaat | gggcgtcaac | ttacccttga | 480 |
| gccgagatta | atcgatcttc | tggttttctt | tgctcaacac | agtggcgaag | tacttagcag | 540 |
| ggatgaactt | atcgataatg | tctggaagag | aagtattgtc | accaatcacg | ttgtgacgca | 600 |
| gagtatctca | gaactacgta | agtcattaaa | agataatgat | gaagatagtc | ctgtctatat | 660 |
| cgctactgta | ccaaagcgcg | gctataaatt | aatggtgccg | gttatctggt | acagcgaaga | 720 |
| agagggagag | gaaataatgc | tatcttcgcc | tcccctata | ccagaggcgg | ttcctgccac | 780 |
| agattctccc | tccacagtc | ttaacattca | aaacaccgca | acgccacctg | aacaatcccc | 840 |
| agttaaaagc | aaacgattca | ctaccttttg | ggtatggttt | ttttttcctgt | tgtcgttagg | 900 |
| tatctgtgta | gcactggtag | cgttttcaag | tctgtcgaca | catatgaaac | agctggaaga | 960 |
| caaagttgaa | gagcccctgt | ctaaaaacta | ccaccccgag | aacgaagttg | cgcgcctgaa | 1020 |
| aaaactagtt | ggtgaacgtt | gaggatcccc | gggtaccgag | ctcg | | 1064 |

<210> SEQ ID NO 4
<211> LENGTH: 1666
<212> TYPE: DNA
<213> ORGANISM: Escherichia coli
<220> FEATURE:
<221> NAME/KEY: modified_base
<222> LOCATION: 58
<223> OTHER INFORMATION: n=a, c, g, or t
<220> FEATURE:
<221> NAME/KEY: modified_base
<222> LOCATION: 105
<223> OTHER INFORMATION: n=a, c, g, or t

<400> SEQUENCE: 4

| | | | | | |
|---|---|---|---|---|---|
| gtcaagtctg | ctttaattat | ttttaagcgt | gcataataag | ccctacacaa | attgggagna | 60 |
| tatatcatga | aaggctggct | ttttcttgtt | atcgcaatag | ttggngaagt | aatcgcaaca | 120 |
| tccgcattaa | aatctagcga | gggctttact | aagctcgcgt | tggccgattc | attaatgcag | 180 |
| ctggcacgac | aggtttcccg | actggaaagc | gggcagtgag | cgcaacgcaa | ttaatgtgag | 240 |

-continued

```
ttagctcact cattaggcac cccaggcttt acactttatg cttccggctc gtatgttgtg    300
tggaattgtg agcggataac aatttcacac aggaaacagc tatgaccatg attacgccaa    360
gcttcattcc cttttcgaat gagtttctat tatgcaacaa cctgtagttc gcgttggcga    420
atggcttgtt actccgtcca taaaccaaat tagccgcaat gggcgtcaac ttacccttga    480
gccgagatta atcgatcttc tggttttctt tgctcaaac agtggcgaag tacttagcag     540
ggatgaactt atcgataatg tctggaagag aagtattgtc accaatcacg ttgtgacgca    600
gagtatctca gaactacgta agtcattaaa agataatgat gaagatagtc ctgtctatat    660
cgctactgta ccaaagcgcg gctataaatt aatggtgccg gttatctggt acagcgaaga    720
agagggagag gaaataatgc tatcttcgcc tcccctata ccagaggcgg ttcctgccac      780
agattctccc tcccacagtc ttaacattca aacaccgca acgccacctg aacaatcccc      840
agttaaaagc aaacgattca ctacctttg ggtatggttt tttttcctgt tgtcgttagg      900
tatctgtgta gcactggtag cgttttcaag tctgtcgacc atggaccacc tcggggcgtc    960
cctctggccc caggtcggct ccctttgtct cctgctcgct ggggccgcct gggcgccccc   1020
gcctaacctc ccggacccca agttcgagag caaagcggcc ttgctggcgg cccggggggcc   1080 cgaagagctt ctgtgcttca ccgagcggtt ggaggacttg gtgtgtttct gggaggaagc   1140
ggcgagcgct ggggtgggcc cgggcaacta cagcttctcc taccagctcg aggatgagcc   1200
atggaagctg tgtcgcctgc accaggctcc cacggctcgt ggtgcggtgc gcttctggtg   1260
ttcgctgcct acagccgaca cgtcgagctt cgtgccccta gagttgcgcg tcacagcagc   1320
ctccggcgct ccgcgatatc accgtgtcat ccacatcaat gaagtagtgc tcctagacgc   1380
ccccgtgggg ctggtggcgc ggttggctga cgagagcggc cacgtagtgt tgcgctggct   1440
cccgccgcct gagacaccca tgacgtctca catccgctac gaggtggacg tctcggccgg   1500
caacggcgca gggagcgtac agagggtgga gatcctggag ggccgcaccg agtgtgtgct   1560
gagcaacctg cggggccgga cgcgctacac cttcgccgtc cgcgcgcgta tggctgagcc   1620
gagcttcggc ggcttctgga gctaggatcc ccgggtaccg agctcg                   1666
```

<210> SEQ ID NO 5
<211> LENGTH: 2533
<212> TYPE: DNA
<213> ORGANISM: Escherichia coli
<220> FEATURE:
<221> NAME/KEY: modified_base
<222> LOCATION: 58
<223> OTHER INFORMATION: n=a, c, g, or t
<220> FEATURE:
<221> NAME/KEY: modified_base
<222> LOCATION: 105
<223> OTHER INFORMATION: n=a, c, g, or t

<400> SEQUENCE: 5

```
gtcaagtctg ctttaattat ttttaagcgt gcataataag ccctacacaa attgggnanga    60 tatatcatga aaggctggct ttttcttgtt atcgcaatag ttggngaagt aatcgcaaca   120
tccgcattaa aatctagcga gggctttact aagctcgcgt tggccgattc attaatgcag   180
ctggcacgac aggtttcccg actggaaagc gggcagtgag cgcaacgcaa ttaatgtgag   240
ttagctcact cattaggcac cccaggcttt acactttatg cttccggctc gtatgttgtg    300
tggaattgtg agcggataac aatttcacac aggaaacagc tatgaccatg attacgccaa    360
gcttcattcc cttttcgaat gagtttctat tatgcaacaa cctgtagttc gcgttggcga    420
```

```
atggcttgtt actccgtcca taaaccaaat tagccgcaat gggcgtcaac ttacccttga    480
gccgagatta atcgatcttc tggttttctt tgctcaacac agtggcgaag tacttagcag    540
ggatgaactt atcgataatg tctggaagag aagtattgtc accaatcacg ttgtgacgca    600
gagtatctca gaactacgta agtcattaaa agataatgat gaagatagtc ctgtctatat    660
cgctactgta ccaaagcgcg gctataaatt aatggtgccg gttatctggt acagcgaaga    720
agagggagag gaaataatgc tatcttcgcc tcccctata ccagaggcgg ttcctgccac     780
agattctccc tcccacagtc ttaacattca aaacaccgca acgccacctg aacaatcccc    840
agttaaaagc aaacgattca ctaccttttg ggtatggttt tttttcctgt tgtcgttagg    900
tatctgtgta gcactggtag cgttttcaag tctgtcgacc cacctgtacc ccggagaggt    960
gtgtcccggc atggatatcc ggaacaacct cactaggttg catgagctgg agaattgctc   1020
tgtcatcgaa ggacacttgc agatactctt gatgttcaaa acgaggcccg aagatttccg   1080
agacctcagt ttccccaaac tcatcatgat cactgattac ttgctgctct ccgggtcta   1140
tgggctcgag agcctgaagg acctgttccc caacctcacg gtcatccggg gatcacgact   1200
gttctttaac tacgcgctgg tcatcttcga gatggttcac ctcaaggaac tcggcctcta   1260
caacctgatg aacatcaccc ggggttctgt ccgcatcgag aagaacaatg agctctgtta   1320
cttggccact atcgactggt cccgtatcct ggattccgtg gaggataatc acatcgtgtt   1380
gaacaaagat gacaacgagg agtgtggaga catctgtccg ggtaccgcga agggcaagac   1440
caactgcccc gccaccgtca tcaacgggca gtttgtcgaa cgatgttgga ctcatagtca   1500
ctgccagaaa gtttgcccga ccatctgtaa gtcacacggc tgcaccgccg aaggcctctg   1560
ttgccacagc gagtgcctgg gcaactgttc tcagcccgac gaccccacca gtgcgtggc   1620
ctgccgcaac ttctacctgg acggcaggtg tgtggagacc tgcccgcccc cgtactacca   1680
cttccaggac tggcgctgtg tgaacttcag cttctgccag gacctgcacc acaaatgcaa   1740
gaactcgcgg aggcagggct gccaccaata cgtcattcac aacaacaagt gcatccctga   1800
gtgtccctcc gggtacacga tgaattccag caacttgctg tgcaccccat gcctgggtcc   1860
ctgtcccaag gtgtgccacc tcctagaagg cgagaagacc atcgactcgg tgacgtctgc   1920
ccaggagctc cgaggatgca ccgtcatcaa cgggagtctg atcatcaaca ttcgaggagg   1980
caacaatctg gcagctgagc tagaagccaa cctcggcctc attgaagaaa tttcagggta   2040
tctaaaaatc cgccgatcct acgctctggt gtcactttcc ttcttccgga agttacgtct   2100
gattcgagga gagaccttgg aaattgggaa ctactccttc tatgccttgg acaaccagaa   2160
cctaaggcag ctctgggact ggagcaaaca caacctcacc accactcagg ggaaactctt   2220
cttccactat aaccccaaac tctgcttgtc agaaatccac aagatggaag aagtttcagg   2280
aaccaagggg cgccaggaga gaaacgacat tgccctgaag accatggggg acaaggcatc   2340
ctgtgaaaat gagttactta aattttctta cattcggaca tcttttgaca agatcttgct   2400
gagatgggag ccgtactggc cccccgactt ccgagacctc ttgggggttca tgctgttcta   2460
caaagaggcc ccttatcaga atgtgacgga gttcgatggg caggatgcgt aggatccccg   2520
ggtaccgagc tcg                                                       2533
```

<210> SEQ ID NO 6
<211> LENGTH: 1478
<212> TYPE: DNA
<213> ORGANISM: Escherichia coli
<220> FEATURE:
<221> NAME/KEY: modified_base
<222> LOCATION: 58
<223> OTHER INFORMATION: n=a, c, g, or t
<220> FEATURE:
<221> NAME/KEY: modified_base
<222> LOCATION: 105
<223> OTHER INFORMATION: n=a, c, g, or t

<400> SEQUENCE: 6

```
gtcaagtctg ctttaattat ttttaagcgt gcataataag ccctacacaa attgggganga      60
tatatcatga aaggctggct ttttcttgtt atcgcaatag ttggngaagt aatcgcaaca     120
tccgcattaa aatctagcga gggctttact aagctcgcgt tggccgattc attaatgcag     180
ctggcacgac aggtttcccg actggaaagc gggcagtgag cgcaacgcaa ttaatgtgag     240
ttagctcact cattaggcac cccaggcttt acactttatg cttccggctc gtatgttgtg     300
tggaattgtg agcggataac aatttcacac aggaaacagc tatgaccatg attacgccaa     360
gcttcattcc ctttttcgaat gagtttctat tatgcaacaa cctgtagttc gcgttggcga     420
atggcttgtt actccgtcca taaaccaaat tagccgcaat gggcgtcaac ttaccctga     480
gccgagatta atcgatcttc tggttttctt tgctcaacac agtggcgaag acttagcag     540
ggatgaactt atcgataatg tctggaagag aagtattgtc accaatcacg ttgtgacgca     600
gagtatctca gaactacgta agtcattaaa agataatgat gaagatagtc ctgtctatat     660
cgctactgta ccaaagcgcg gctataaatt aatggtgccg gttatctggt acagcgaaga     720
agagggagag gaaataatgc tatcttcgcc tcccccctata ccagaggcgg ttcctgccac     780
agattctccc tcccacagtc ttaacattca aaacaccgca acgccacctg aacaatcccc     840
agttaaaagc aaacgattca ctaccttttg ggtatggttt tttttcctgt tgtcgttagg     900
tatctgtgta gcactggtag cgttttcaag tctgtcgaca gatagtgtgt gtccccaagg     960
aaaatatatc caccctcaaa ataattcgat ttgctgtacc aagtgccaca aaggaaccta    1020
cttgtacaat gactgtccag gcccggggca ggatacggac tgcagggagt gtgagagcgg    1080
ctccttcacc gcttcagaaa accacctcag acactgcctc agctgctcca aatgccgaaa    1140
ggaaatgggt caggtggaga tctcttcttg cacagtggac cgggacaccg tgtgtggctg    1200
caggaagaac cagtaccggc attattggag tgaaaacctt ttccagtgct tcaattgcag    1260
cctctgcctc aatgggaccg tgcacctctc ctgccaggag aaacagaaca ccgtgtgcac    1320
ctgccatgca ggtttctttc taagagaaaa cgagtgtgtc tcctgtagta actgtaagaa    1380
aagcctggag tgcacgaagt tgtgcctacc ccagattgag aatgttaagg gcactgagga    1440
ctcaggcacc acatgaggat ccccgggtac cgagctcg                            1478
```

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 7

```
tcccccgggg tataatatgt tgcggc                                           26
```

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 8
cgggatccag aactcatgct cttc                                          24

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 9
cgcggatcca cacaggaaac agctatgac                                     29

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 10
ccgctcgaga catggcctgc ccgg                                          24

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 11
ccgctcgaga tcgggctatt tgcctg                                        26

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 12
gtacgcgtcg acagcggtaa taccaatcgc                                    30

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 13
ccgggatcca ggagctaagg aagctaaaat g                                  31

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 14
caggcgtagc actcgaggcg tttaag                                        26

<210> SEQ ID NO 15
<211> LENGTH: 24

```
<212> TYPE: DNA
<213> ORGANISM: Artificial Sequence
<220> FEATURE:
<223> OTHER INFORMATION: Description of Artificial Sequence: Primer

<400> SEQUENCE: 15
cagtttgtga gtcgactggg tttc                                           24

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 16
cccaagcttc attccctttt cgaatg                                         26

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 17
caggtttccc tctagagtca cgacgctttg gtacagtagc g                        41

<210> SEQ ID NO 18
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 18
tcctgagtgt cgacaaattg ccgcgcggct ataaattaat ggtg                     44

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 19
tgctctagat tgagcaaaat acgcg                                          25

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 20
gtcgtgactc tagagggaaa cctggaaagc cacgttgtgt ctc                      43

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 21
```

```
cgggcaattt gtcgacactc aggagccgcc gtcccgtcaa gtc                    43
```

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 22

```
tccccccggg tataatatgt tgcggc                                      26
```

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 23

```
cgggatccag aactcatgct cttc                                        24
```

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 24

```
cgcggatcca cacaggaaac agctatgac                                   29
```

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 25

```
ccgctcgaga catggcctgc ccgg                                        24
```

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 26

```
ccgctcgaga tcgggctatt tgcctg                                      26
```

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 27

```
gtacgcgtcg acagcggtaa taccaatcgc                                  30
```

<210> SEQ ID NO 28
<211> LENGTH: 27
<212> TYPE: DNA
<213> ORGANISM: Artificial Sequence

```
<220> FEATURE:
<223> OTHER INFORMATION: Description of Artificial Sequence: Primer

<400> SEQUENCE: 28
ccccaagctt cattcccttt tcgaatg                                          27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 29
tgcggtcgaa gacttgaaaa cgctacc                                          27

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 30
acgcgtcgac acatatgaaa c                                                21

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 31
gcttggatcc tcaacgttc                                                   19

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 32
tgcggtcgac aattttatcg acataaag                                         28

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 33
ctgtatcatg gaccacctcg gggcg                                            25

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 34
tgcagcctgg tgtcctaaga gcaagc                                           26
```

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 35
acgcgtcgac ccacctgtac cccggagagg t                                    31

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 36
cgcggatcct acgcatcctg cccatcgaac tc                                   32

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 37
gcctgatccg aggagacccc gcg                                             23

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 38
gtaggcactg ttaggaagga ttggaccga                                       29

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 39
acgcgtcgac ccacctgtac cccggagagg t                                    31

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 40
cgcggatcct acgcatcctg cccatcgaac tc                                   32

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 41
tgtctggcat gggcctctcc accgt                                    25

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 42
ggaaggcgat ctccgaggac ggtcc                                    25

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 43
gggcgtcgac agatagtgtg tgtccccaag g                             31

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 44
cgcggatcct catgtggtgc ctgagtcctc ag                            32

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 45
cggaattcag ataacgaggg caaaaaatg                                29

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 46
gctctagagg cctgcgctac ggtagcg                                  27

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 47
cgcggagatg ggggtgcacg aat                                      23

<210> SEQ ID NO 48

```
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 48
gctgagctga gagcccctcg acgg                                          24

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 49
gctctagact tctcctgtcc ctgctgtc                                      28

<210> SEQ ID NO 50
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 50
gcccaagctt gcccaggtgg acacacctg                                     29

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 51
cctttgtgaa ccaacacctg tgcggc                                        26

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 52
ggctgcctgc aggctgcgtc tagt                                          24

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 53
gctctagatt tgtgaaccaa cacctgtgcg gc                                 32

<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 54
```

-continued

```
gcccaagctt gctgcctgca ggctgcgtct ag                        32

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 55
tctcccctgg aaaggacacc atgagc                               26

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 56
ggcgtttggg aaggttggat gttcg                                25

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 57
gctctagaga agagttcccc acggacctct ctc                       33
```